United States Patent
Py et al.

(10) Patent No.: US 7,290,573 B2
(45) Date of Patent: *Nov. 6, 2007

(54) DISPENSER WITH SEALED CHAMBER, ONE-WAY VALVE AND NEEDLE PENETRABLE AND LASER RESEALABLE STOPPER

(75) Inventors: Daniel Py, Stamford, CT (US); Norbert M. Assion, Shelton, CT (US); Julian V. Chan, Spring Valley, CT (US)

(73) Assignee: Medical Instill Technologies, Inc., New Milford, CT (US)

( * ) Notice: Subject to any disclaimer, the term of this patent is extended or adjusted under 35 U.S.C. 154(b) by 81 days.

This patent is subject to a terminal disclaimer.

(21) Appl. No.: 11/195,520

(22) Filed: Aug. 1, 2005

(65) Prior Publication Data

US 2005/0263543 A1    Dec. 1, 2005

Related U.S. Application Data

(63) Continuation of application No. 10/272,577, filed on Oct. 16, 2002, now Pat. No. 6,957,752.

(60) Provisional application No. 60/403,396, filed on Aug. 13, 2002, provisional application No. 60/403,484, filed on Aug. 13, 2002, provisional application No. 60/329,779, filed on Oct. 16, 2001.

(51) Int. Cl.
   *B65B 1/04*    (2006.01)

(52) U.S. Cl. ............... 141/329; 222/390; 222/386; 222/494

(58) Field of Classification Search .......... 141/2, 141/18, 21, 27, 85, 329; 222/386, 390, 494, 222/563; 604/256, 415

See application file for complete search history.

(56) References Cited

U.S. PATENT DOCUMENTS

| | | | |
|---|---|---|---|
| 2,503,147 A | 4/1950 | Applezweig | |
| 2,626,087 A | 1/1953 | Howard et al. | |
| 2,648,334 A | 8/1953 | Brown et al. | |
| 2,667,986 A | 2/1954 | Perelson | |
| 3,092,278 A | 6/1963 | Järnhäll | |
| 3,136,440 A | 6/1964 | Krug et al. | |
| 3,193,128 A | 7/1965 | Ravn | |
| 3,278,063 A | 10/1966 | Kranzhoff | |

(Continued)

FOREIGN PATENT DOCUMENTS

CA    1123792    5/1982

(Continued)

OTHER PUBLICATIONS

International Search Report of International Application No. PCT/US02/32935.

*Primary Examiner*—Steven O. Douglas
(74) *Attorney, Agent, or Firm*—McCarter & English, LLP

(57) ABSTRACT

A syringe is provided for the delivery of controlled, metered amounts of any of numerous different substances to humans or animals, such as medicaments, pharmaceuticals, cosmetics, and food products, or to deliver materials which may react upon exposure to air, such as glue. The syringes include a body and a plunger. Means are provided in the syringe body and the plunger to effect controlled movement of the plunger into the syringe to permit delivery of a pre-determined amount of the substance contained in the syringe. A one-way valve is provided at the dispensing tip of the syringe to hermetically seal the portion of the syringe containing the substance to be dispensed.

23 Claims, 35 Drawing Sheets

U.S. PATENT DOCUMENTS

| | | | |
|---|---|---|---|
| 3,340,671 A | 9/1967 | Loo | |
| 3,353,718 A | 11/1967 | McLay | |
| 3,358,865 A | 12/1967 | Andersen | |
| 3,392,859 A | 7/1968 | Fischer | |
| 3,424,329 A | 1/1969 | Hersherg et al. | |
| 3,637,102 A | 1/1972 | Shaw | |
| 3,659,749 A | 5/1972 | Schwartz | |
| 3,662,753 A | 5/1972 | Tassell | |
| 3,685,248 A | 8/1972 | Godelaine | |
| 3,699,961 A | 10/1972 | Szpur | |
| 3,811,591 A | 5/1974 | Novitch | |
| 3,838,689 A | 10/1974 | Cohen | |
| 4,048,255 A | 9/1977 | Hillier et al. | |
| 4,050,459 A | 9/1977 | Sanchez | |
| 4,185,628 A | 1/1980 | Kopfer | |
| 4,189,065 A | 2/1980 | Herold | |
| 4,205,754 A | 6/1980 | Nielsen et al. | |
| 4,250,611 A | 2/1981 | Wong | |
| 4,251,003 A | 2/1981 | Bodenmann | |
| 4,265,364 A | 5/1981 | Baba | |
| 4,346,708 A | 8/1982 | LeVeen et al. | |
| 4,366,912 A | 1/1983 | Matukura et al. | |
| 4,367,739 A | 1/1983 | LeVeen et al. | |
| 4,388,011 A | 6/1983 | Smith | |
| 4,390,111 A | 6/1983 | Robbins et al. | |
| 4,444,330 A | 4/1984 | Kasai et al. | |
| 4,456,138 A | 6/1984 | Bereziat | |
| 4,471,879 A | 9/1984 | Connor et al. | |
| 4,475,905 A | 10/1984 | Himmelstrup | |
| 4,479,578 A | 10/1984 | Brignola et al. | |
| 4,499,148 A | 2/1985 | Goodale et al. | |
| D279,651 S | 7/1985 | Freeman | |
| 4,526,294 A | 7/1985 | Hirschmann et al. | |
| 4,635,807 A | 1/1987 | Knapp | |
| 4,643,723 A | 2/1987 | Smit | |
| 4,664,275 A | 5/1987 | Kasai et al. | |
| 4,664,277 A | 5/1987 | Connor | |
| 4,682,703 A | 7/1987 | Kasai et al. | |
| 4,703,781 A | 11/1987 | Meyer et al. | |
| 4,781,701 A * | 11/1988 | Geprags | 604/240 |
| 4,815,619 A | 3/1989 | Turner et al. | |
| 4,834,152 A | 5/1989 | Howson et al. | |
| 4,842,028 A | 6/1989 | Kaufman et al. | |
| 4,865,591 A | 9/1989 | Sams | |
| 4,910,435 A | 3/1990 | Wakalopulos | |
| 4,936,833 A | 6/1990 | Sams | |
| 4,962,868 A | 10/1990 | Borchard | |
| 4,973,318 A | 11/1990 | Holm et al. | |
| 5,009,654 A | 4/1991 | Minshall et al. | |
| 5,031,675 A | 7/1991 | Lindgren | |
| 5,038,839 A | 8/1991 | Morimoto et al. | |
| 5,085,332 A | 2/1992 | Gettig et al. | |
| 5,088,612 A | 2/1992 | Storar et al. | |
| 5,088,995 A | 2/1992 | Packard et al. | |
| 5,129,212 A | 7/1992 | Duffey et al. | |
| 5,226,895 A | 7/1993 | Harris | |
| 5,244,465 A | 9/1993 | Michel | |
| 5,247,015 A | 9/1993 | Bayan | |
| 5,253,785 A | 10/1993 | Haber et al. | |
| 5,290,260 A | 3/1994 | Stines | |
| 5,341,854 A | 8/1994 | Zezulka et al. | |
| 5,344,036 A | 9/1994 | Stanescu et al. | |
| 5,360,145 A | 11/1994 | Gueret | |
| 5,379,908 A | 1/1995 | Rohe | |
| 5,390,469 A | 2/1995 | Shimizu et al. | |
| 5,411,065 A | 5/1995 | Meador et al. | |
| 5,414,267 A | 5/1995 | Wakalopulos | |
| 5,464,111 A | 11/1995 | Vacek et al. | |
| 5,484,566 A | 1/1996 | Gabbard | |
| 5,496,302 A | 3/1996 | Minshall et al. | |
| RE35,203 E | 4/1996 | Wakalopulos | |
| 5,514,339 A | 5/1996 | Leopardi et al. | |
| 5,545,147 A | 8/1996 | Harris | |
| 5,549,141 A | 8/1996 | Meador et al. | |
| 5,582,598 A | 12/1996 | Chanoch | |
| 5,591,136 A | 1/1997 | Gabriel | |
| 5,597,530 A * | 1/1997 | Smith et al. | 422/28 |
| 5,612,588 A | 3/1997 | Wakalopulos | |
| 5,626,566 A | 5/1997 | Petersen et al. | |
| 5,630,800 A | 5/1997 | Blank et al. | |
| 5,636,930 A | 6/1997 | Holloway | |
| 5,641,004 A | 6/1997 | Py | |
| D383,214 S | 9/1997 | Brennan | |
| 5,673,535 A | 10/1997 | Jagger | |
| 5,702,019 A | 12/1997 | Grimard | |
| D389,586 S | 1/1998 | Brennan | |
| 5,718,348 A | 2/1998 | Manera | |
| 5,728,075 A | 3/1998 | Levander | |
| 5,743,889 A | 4/1998 | Sams | |
| 5,744,087 A | 4/1998 | Williams et al. | |
| 5,785,683 A | 7/1998 | Szapiro et al. | |
| 5,816,772 A | 10/1998 | Py | |
| 5,823,373 A | 10/1998 | Sudo et al. | |
| 5,829,901 A | 11/1998 | Brown et al. | |
| 5,842,321 A | 12/1998 | Jones | |
| 5,876,372 A | 3/1999 | Grabenkort et al. | |
| 5,879,336 A | 3/1999 | Brinon | |
| 5,902,298 A | 5/1999 | Niedospial, Jr. et al. | |
| 5,909,032 A | 6/1999 | Wakalopulos | |
| 5,931,828 A | 8/1999 | Durkee | |
| 5,971,181 A | 10/1999 | Niedospial, Jr. et al. | |
| 6,003,736 A | 12/1999 | Ljunggren | |
| 6,004,298 A | 12/1999 | Levander | |
| 6,006,932 A | 12/1999 | Morini | |
| 6,021,824 A | 2/2000 | Larsen et al. | |
| 6,050,435 A | 4/2000 | Bush et al. | |
| 6,053,893 A | 4/2000 | Bucher | |
| 6,068,150 A | 5/2000 | Mitchell et al. | |
| 6,070,748 A | 6/2000 | Storar | |
| 6,083,201 A | 7/2000 | Skinkle | |
| 6,095,355 A | 8/2000 | Jessen et al. | |
| 6,140,657 A | 10/2000 | Wakalopulos et al. | |
| 6,145,688 A | 11/2000 | Smith | |
| 6,168,037 B1 | 1/2001 | Grimard | |
| 6,186,686 B1 | 2/2001 | Neuner et al. | |
| 6,193,698 B1 | 2/2001 | Kirchhofer et al. | |
| D439,345 S | 3/2001 | Herchenbach et al. | |
| 6,199,350 B1 | 3/2001 | Brechel et al. | |
| 6,200,047 B1 | 3/2001 | Holloway | |
| 6,223,918 B1 | 5/2001 | Browne | |
| 6,234,335 B1 | 5/2001 | Gee et al. | |
| 6,234,363 B1 | 5/2001 | Stradella | |
| 6,263,778 B1 | 7/2001 | Brass et al. | |
| 6,280,421 B1 | 8/2001 | Kirchhofer et al. | |
| 6,290,679 B1 | 9/2001 | Hostettler et al. | |
| 6,308,494 B1 | 10/2001 | Yuyama et al. | |
| RE37,471 E | 12/2001 | Jagger | |
| 6,338,442 B1 | 1/2002 | De Laforcade | |
| 6,343,711 B1 | 2/2002 | Coughlin | |
| 6,364,864 B1 | 4/2002 | Mohiuddin et al. | |
| 6,371,129 B1 | 4/2002 | Le Bras-Brown et al. | |
| 6,382,441 B1 | 5/2002 | Carano | |
| 6,383,167 B2 | 5/2002 | Kirchhofer et al. | |
| 6,385,943 B2 | 5/2002 | Yuyama et al. | |
| 6,419,412 B1 | 7/2002 | Ostrowski et al. | |
| 6,485,470 B2 | 11/2002 | Hostettler et al. | |
| 6,568,439 B1 | 5/2003 | Se et al. | |
| 6,604,561 B2 | 8/2003 | Py | |
| 6,663,602 B2 | 12/2003 | Moller | |
| 6,684,916 B2 | 2/2004 | Py | |
| 2001/0009990 A1 | 7/2001 | Hostettler et al. | |
| 2001/0041872 A1 | 11/2001 | Paul, Jr. | |
| 2002/0006353 A1 | 1/2002 | Bilstad et al. | |
| 2002/0010995 A1 | 1/2002 | Thibault et al. | |

| | | | | | | |
|---|---|---|---|---|---|---|
| 2002/0018731 | A1 | 2/2002 | Bilstad et al. | FR | 2509689 | 7/1981 |
| 2002/0023893 | A1 | 2/2002 | Sudo et al. | GB | 500534 | 2/1939 |
| 2002/0029022 | A1 | 3/2002 | Naritomi et al. | GB | 984149 | 2/1965 |
| 2002/0071708 | A1 | 6/2002 | Fontanet et al. | GB | 2091229 | 7/1982 |
| 2002/0131902 | A1 | 9/2002 | Levy | GB | 2364700 | 2/2002 |
| 2002/0172615 | A1 | 11/2002 | Woodworth et al. | WO | WO95/34381 | 12/1995 |
| 2003/0098286 | A1 | 5/2003 | Boom et al. | | | |
| 2003/0156973 | A1 | 8/2003 | Bilstad et al. | | | |

FOREIGN PATENT DOCUMENTS

| | | | | |
|---|---|---|---|---|
| EP | 0 921 151 | 10/2001 | | * cited by examiner |

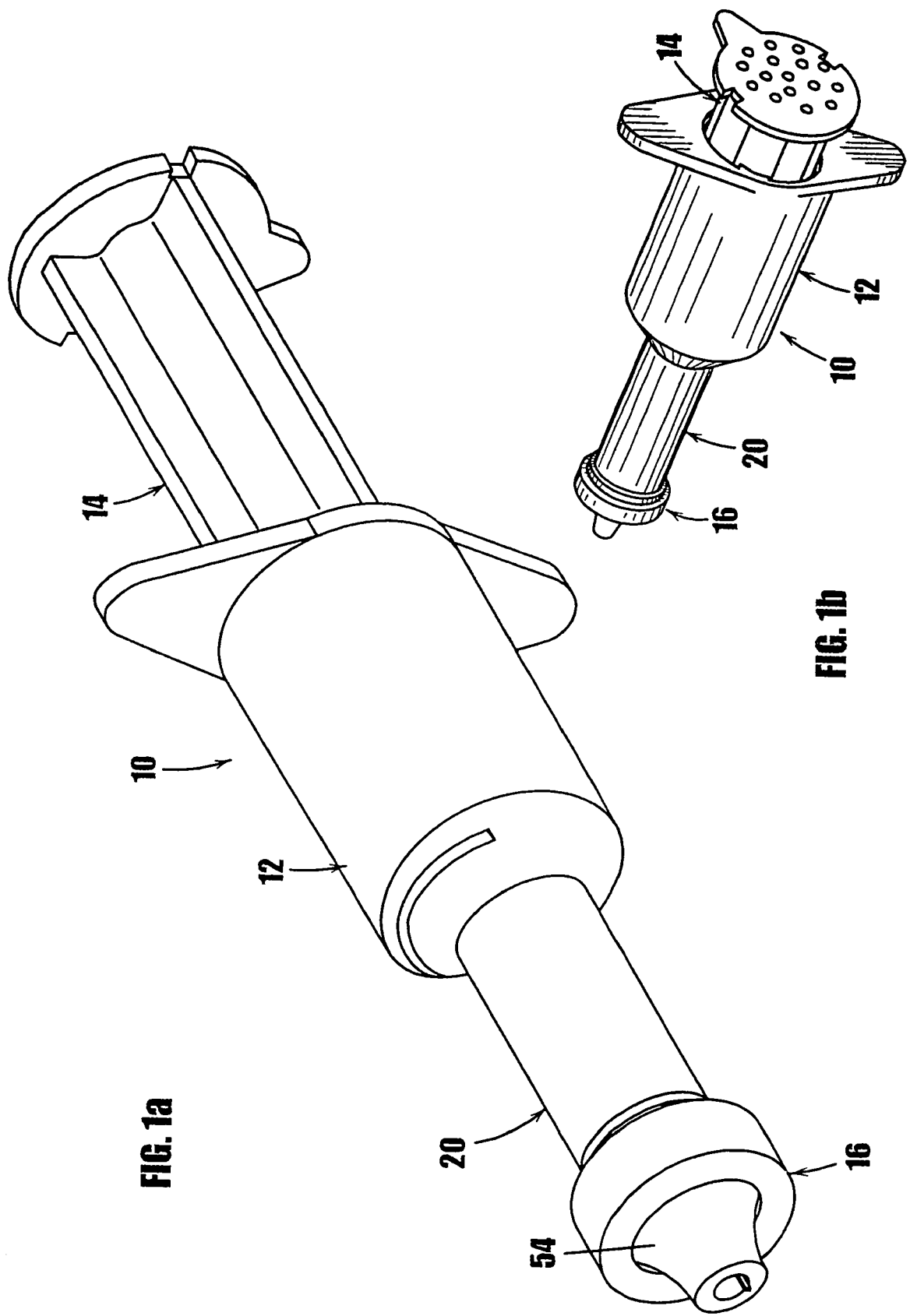

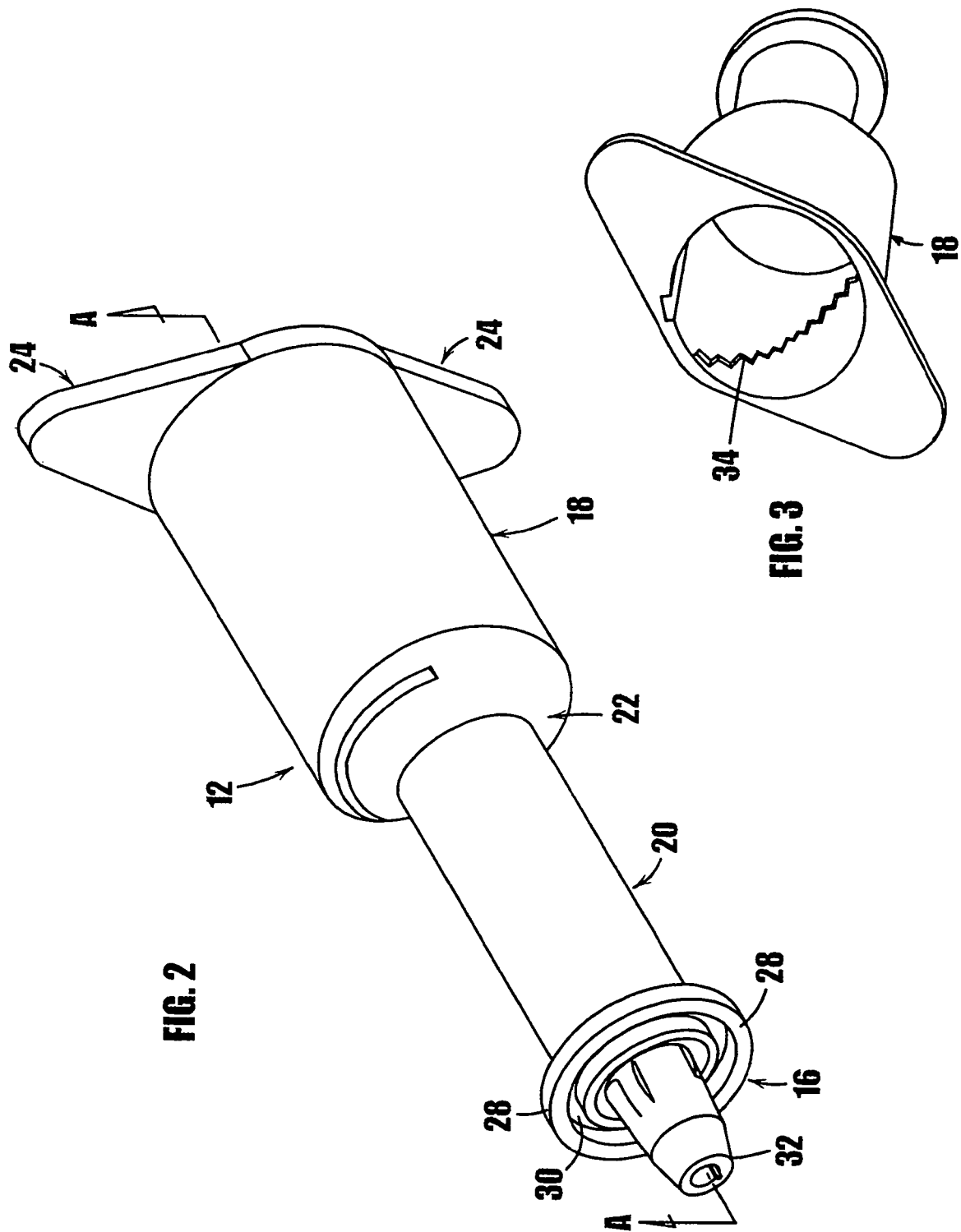

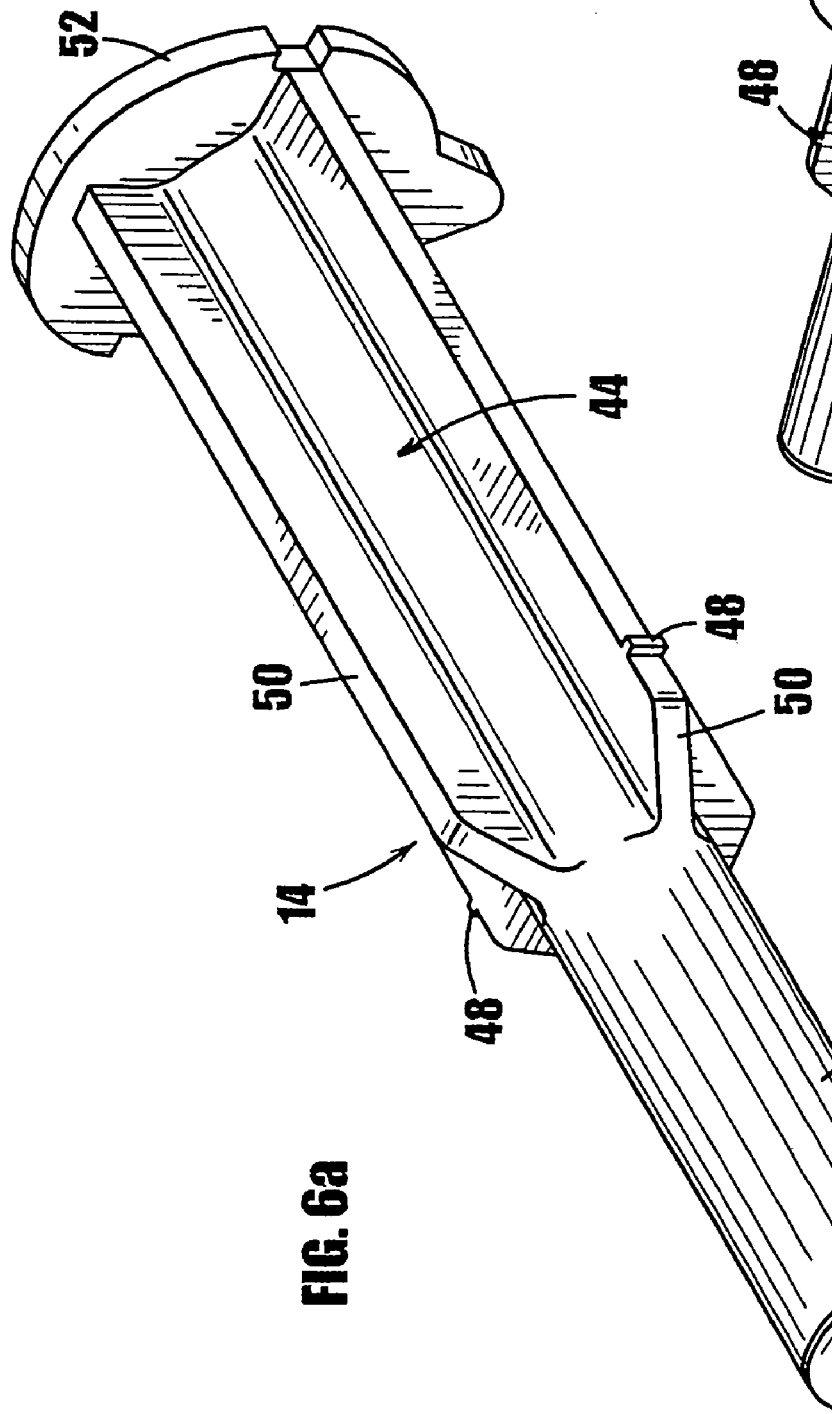
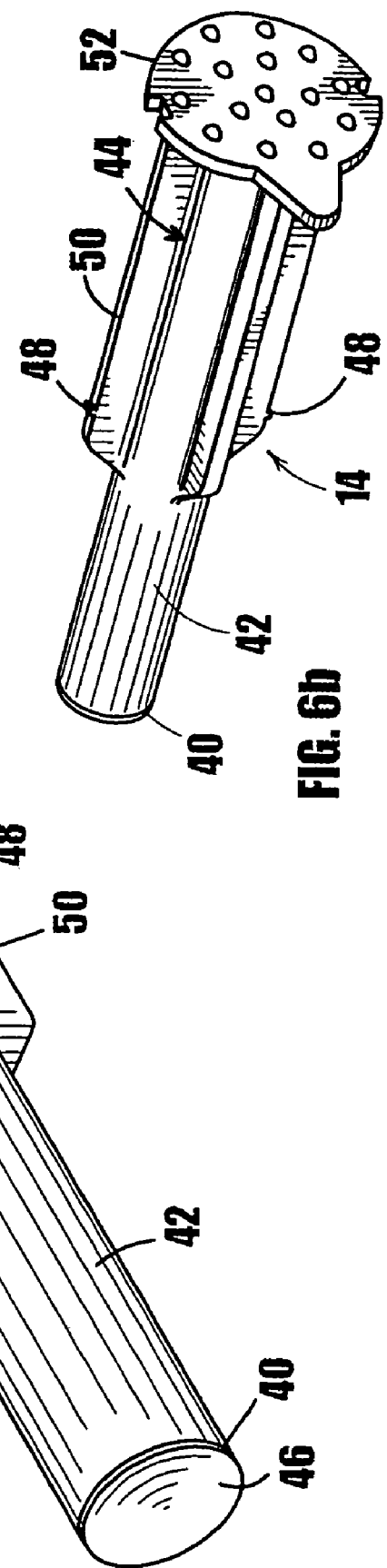
FIG. 6a
FIG. 6b

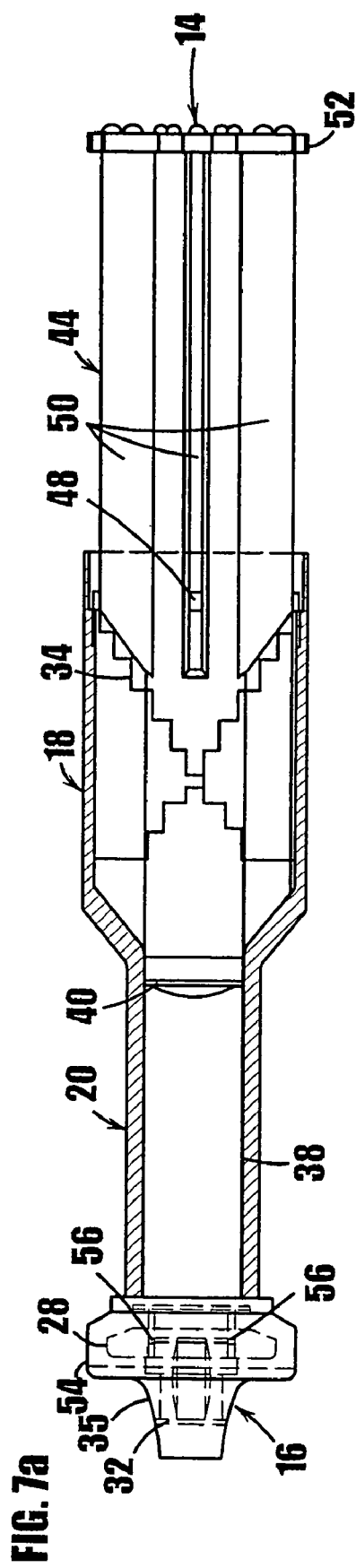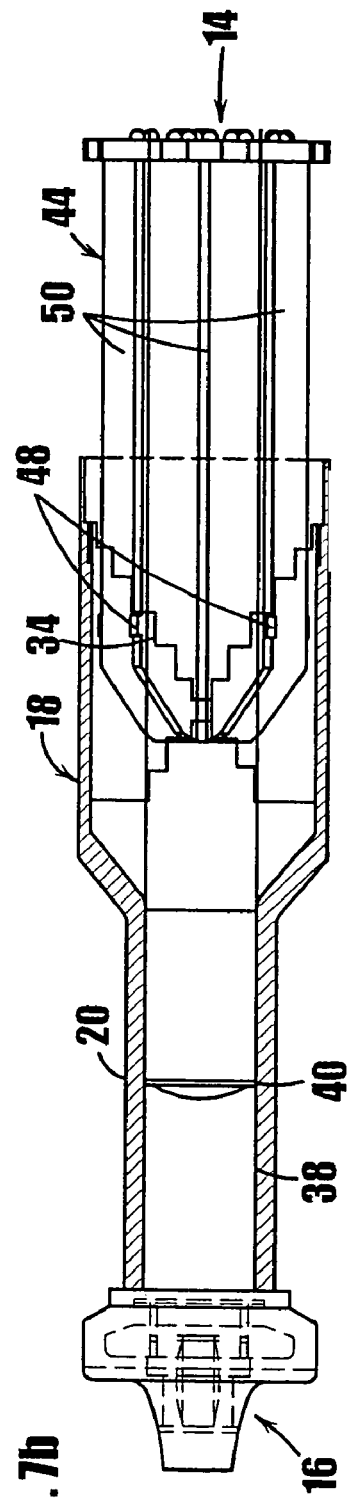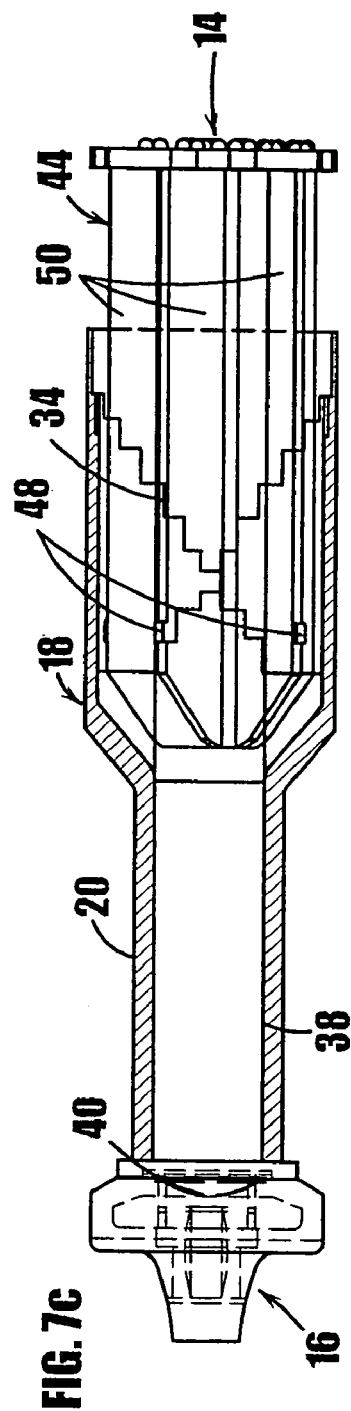

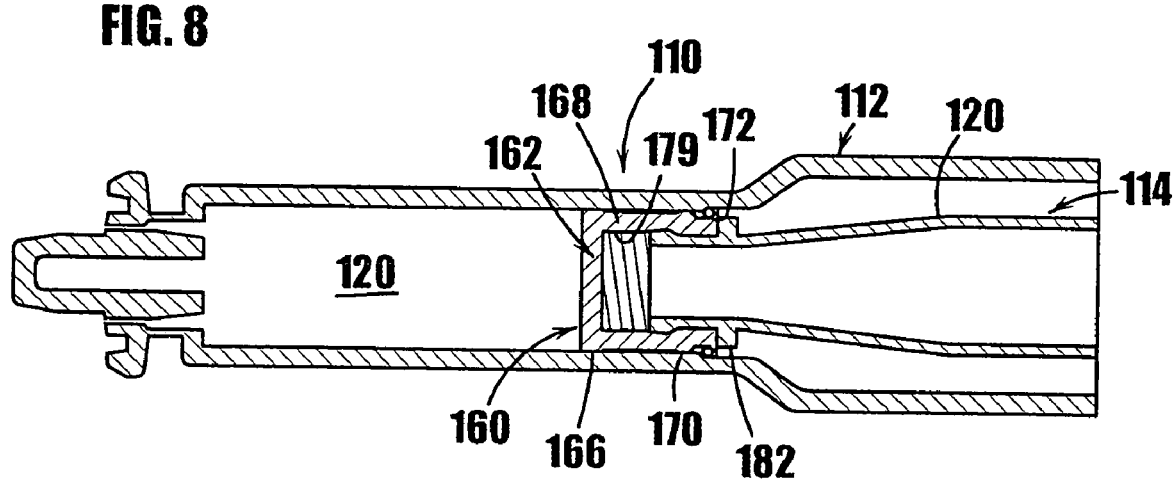

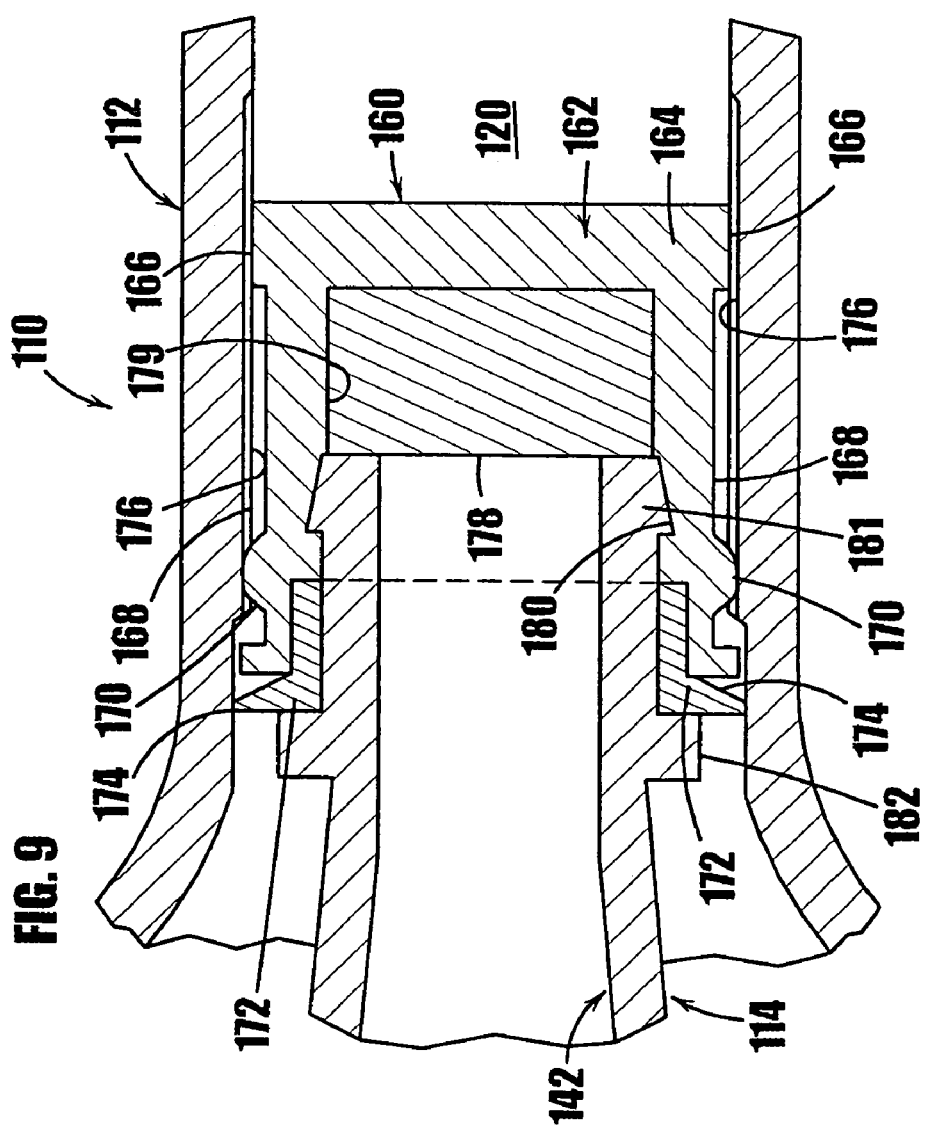
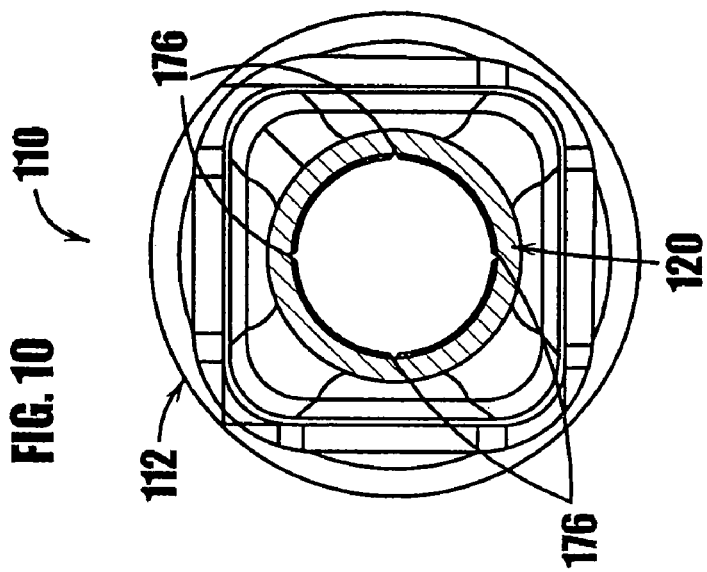
FIG. 9
FIG. 10

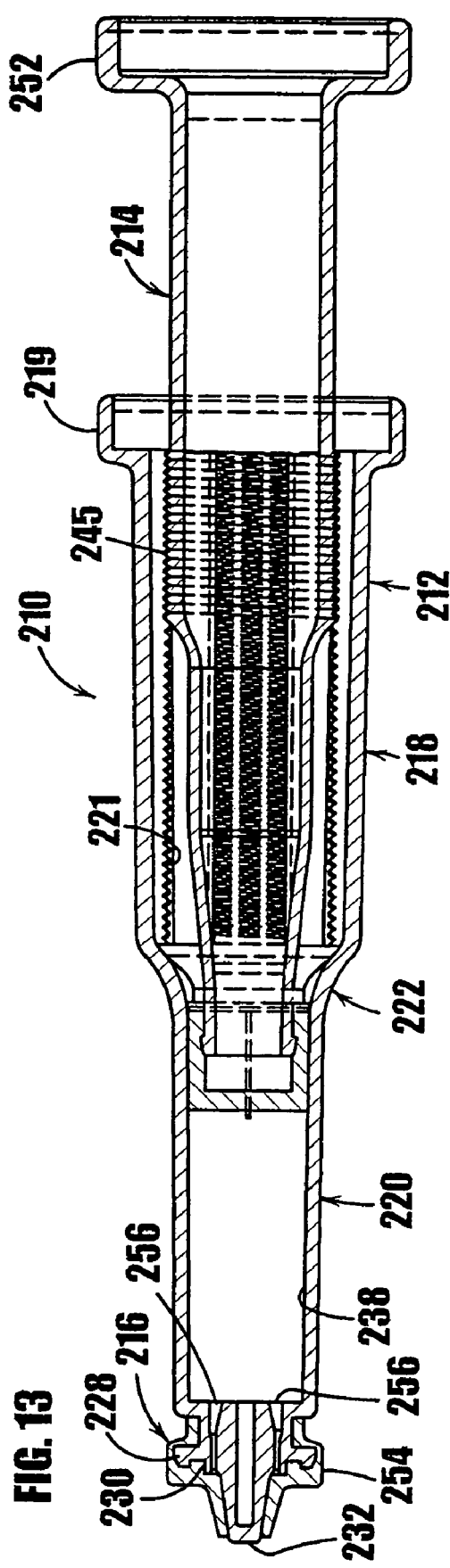
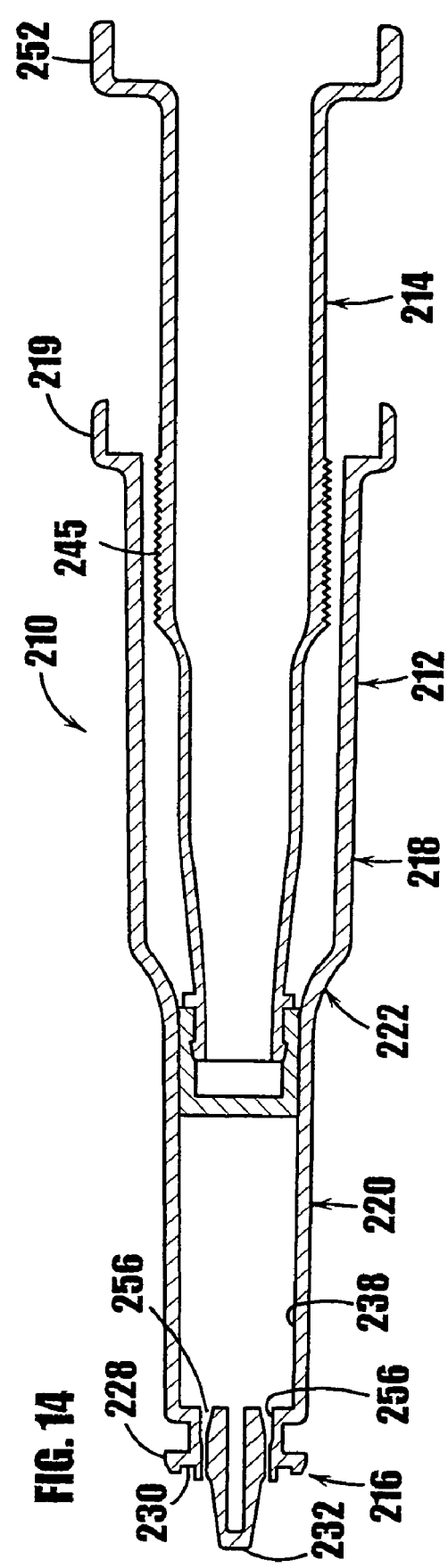
FIG. 13
FIG. 14

DISPENSER WITH SEALED CHAMBER, ONE-WAY VALVE AND NEEDLE PENETRABLE AND LASER RESEALABLE STOPPER

CROSS-REFERENCE TO RELATED APPLICATIONS

This patent application is a continuation of U.S. patent application Ser. No. 10/272,577 filed on Oct. 16, 2002 now U.S. Pat. No. 6,957,752 entitled "Dispenser with Sealed Chamber and One-Way Valve for Providing Metered Amounts of Substances", which in turn claims priority to U.S. Provisional Patent Application Ser. No. 60/329,779, filed Oct. 16, 2001, entitled "Syringe For Providing Metered Amounts Of Substances", and is related to U.S. Provisional Patent Application Ser. No. 60/403,484 filed on Aug. 13, 2002, entitled "Dispensing With Sealed Chamber And One-Way Valve For Providing Material Amounts of Substances," and U.S. Provisional Patent Application Ser. No. 60/403, 396, filed Aug. 13, 2002, entitled "Container For Storing And Dispensing Sterile Substances And Method Of Making And Filling Same", each of which is hereby expressly incorporated by reference as part of the present disclosure.

FIELD OF THE INVENTION

The present invention relates to syringes and like dispensers for delivering any of numerous different substances to humans or animals, such as medicaments, pharmaceuticals, cosmetics, and food products, or to deliver materials which react upon exposure to air, such as glues. The dispensers of the present invention include fusible or other stoppers connected to, or otherwise forming the plungers, for hermetically sealing the interfaces between the plungers and the interiors of the dispensers, and thereby preventing ingress of air or contaminants through the plungers. The dispensers of the present invention also may include a one-way valve forming a dispensing tip, for hermetically sealing the dispensing tip and likewise preventing ingress of air or contaminants through the dispensing tip and into the medicaments or other substances contained within the dispensers. By preventing the ingress of air or contaminants to the substances contained within the dispenser, the use of preservatives in the substances may be reduced or eliminated.

BACKGROUND OF THE INVENTION

Delivery of controlled doses of medicaments is desirable to avoid overmedication. Overmedication can especially occur when the medicament is in the form of a creme or liquid. For example, while it is highly desirable to carefully control the dosage of medicaments given to infants or children, it can be difficult to measure the proper dose using traditional measuring devices such as measuring cups. When the medicament is in the form of a creme or ointment, such as for example cremes applied to the face to control skin acne, the medicaments are often stored in tubes or other containers that do not provide delivery of precise doses of the medicament. Application of excess amounts of the creme can result in skin irritation and drying. Also, application of cremes using fingers can result in contamination of the medicament.

For some medicaments, such as for example the antiseptic Betadyne™, delivery of a controlled dose in a precise location on the skin is desirable to avoid excessive staining of skin or clothing. For certain vaccines, such as the vaccine for gastroenteritis, a hermetically sealed dispenser that can deliver multiple precise doses of the vaccine can reduce waste of both the vaccine and dispensers.

Several devices have been described previously which permit controlled doses of medicaments to be delivered. These devices can be complicated to manufacture, assemble and fill with the medicament. As a result, these devices can be expensive to manufacture and may not be useful for over the counter ("OTC") medicaments. Another disadvantage of such devices is that air can enter the device during storage or as the medicament is delivered. Air entering the device during storage or delivery of the medicament can cause degradation of the medicament, reducing the efficacy of the medicament or causing spoilage which may require that the medicament be discarded.

For some medicaments, preservatives are added to prevent degradation or spoilage of the medicament before use due to ingress of air or other contaminants. The preservatives can react with the medicament, however, reducing its efficacy. Also, some users can have undesirable adverse reactions to the preservatives in the medicaments.

One-way spray tips for dispensing medicaments in aerosol form or for delivery to the eye have been described in U.S. Pat. No. 5,320,845 to Dr. Daniel Py issued on Jun. 14, 1994, U.S. Pat. No. 5,613,957 to Dr. Daniel Py issued on Mar. 25, 1997, U.S. Pat. No. 5,746,728 to Dr. Daniel Py issued on May 5, 1998, U.S. Pat. No. 5,855,322 to Dr. Daniel Py issued on Jan. 5, 1999 and U.S. Pat. No. 6,053,433 to Dr. Daniel Py issued on Apr. 25, 2000, each of which is hereby incorporated by reference as part of the present disclosure.

Cosmetics, such as cremes or liquid make-ups, can also degrade or spoil with exposure to air. Accordingly, it would be desirable to provide a dispenser that could prevent the ingress of air or other contaminants into the medicament, cosmetic or other substance contained within the dispenser, as well as provide improved control of the amount of the substance dispensed therefrom. It also would be desirable to provide a hermetically sealed dispenser that could be used to deliver controlled amounts of other air-sensitive substances, such as for example glues, while preserving unused portions of the substance for later use.

Accordingly, it is an object of the present invention to overcome one or more of the drawbacks and/or disadvantages of the prior art.

SUMMARY OF THE INVENTION

The present is directed to a dispenser adapted to be filled with a substance by an apparatus including a needle for piercing the dispenser and introducing the substance through the needle and into the dispenser, and an energy source, such as a laser, for thermally resealing an aperture in the dispenser after withdrawal of the needle therefrom. The dispenser comprises a body defining a chamber for receiving the substance and a one-way valve mounted on the body. The one-way valve includes an axially-elongated valve seat, and an axially-elongated flexible valve member secured to the valve seat and defining a normally-closed valve opening at the interface of the valve member and valve seat that is connectable in fluid communication with the chamber. A piston or plunger is mounted within the body and movable axially therethrough for varying the volume of the chamber upon dispensing substance from the chamber through the one-way valve. A resealable stopper is in fluid communication with the chamber and is penetrable by the needle for introducing the substance through the stopper and into the chamber. The resealable stopper includes a penetrable region that is fusible in response to the application of thermal energy from the energy source thereto hermetically seal an aperture in the penetrable region after removing the needle therefrom.

In one embodiment of the present invention, the heat-resealable or fusible stopper is included at the base of the plunger. In one such embodiment, the fusible stopper includes a vulcanized rubber base and an insert made of a heat-sealable material. In another such embodiment, the stopper is made of blend of polymeric materials that may be heat resealed by the application of laser energy or like radiation thereto. The chamber for storage of the substance is filled by inserting a needle through the fusible stopper and in fluid communication with the chamber. In one such embodiment, as the storage chamber is filled, the air in the storage chamber is allowed to escape past a flexible flap on the outer periphery of the fusible stopper or through an aperture formed within the needle (e.g., a double lumen needle) or between the needle and stopper. After the storage chamber is filled, the heat sealable material of the stopper is heated to fuse the hole created by the needle, and the flexible flap on the outer periphery of the fusible stopper returns to its normal position to hermetically seal the storage chamber.

In accordance with one embodiment of the present invention, the energy source is a laser that transmits laser radiation at a predetermined wavelength and power. The penetrable region of the resealable stopper is heat resealable to hermetically seal the needle aperture by applying laser radiation from the laser at the predetermined wavelength and power thereto. The stopper comprises a thermoplastic body defining (i) a predetermined wall thickness in an axial direction thereof, (ii) a predetermined color and opacity that substantially absorbs laser radiation at the predetermined wavelength and substantially prevents the passage of radiation through the predetermined wall thickness thereof, and (iii) a predetermined color and opacity that causes the laser radiation at the predetermined wavelength and power to hermetically seal a needle aperture formed in the needle penetration region thereof in a predetermined time period of less than approximately 2 seconds and substantially without burning the needle penetration region. In one such embodiment, the predetermined wavelength of the laser is about 980 nm, the predetermined power of the laser is within the range of about 8 to 10 Watts, the predetermined color of the resealable stopper is gray, and the predetermined opacity of the resealable stopper is defined by a dark gray colorant additive within the range of about 0.3% to about 0.6% by weight Another embodiment of the present invention includes means for preventing residual seepage of substance through the one-way valve. In a currently preferred embodiment, the body defines a plurality of first threads and the plunger defines a plurality of second threads engageable with the first threads for moving at least one of the plunger and body relative to the other. In this embodiment, the means for preventing residual seepage is defined by an axial spacing formed between first and second threads. The axial spacing is sufficient to allow at least one of the plunger and body to move axially relative to the other after dispensing a metered amount of substance through the one-way valve to, in turn, reduce and/or eliminate any pressure differential between the chamber containing the substance and the exterior of the dispenser.

One advantage of the currently preferred embodiments of the present invention is that the dispensers are capable of delivering controlled doses of any of numerous different substances, such as pharmaceutical, vaccine, drug or other medicinal preparations or formulations, cosmetic products, food products, and industrial or other household products, such as glues. The currently preferred embodiments of the present invention are relatively inexpensive to manufacture; thereby allowing the dispensers to be used with a wide variety of substances, including liquids, cremes, ointments, pasty products and other fluids and substances.

Another advantage of the present invention is that the one-way valve at the dispensing tip of the dispenser hermetically seals the tip and prevents the ingress of air or other contaminants into the substance contained in the dispenser, thereby allowing the substance to be stored without preservatives and further allowing multiple doses of such non-preserved substances to be contained in the dispenser.

Other advantages of the syringes and other dispensers of the present invention will become more readily apparent in view of the following detailed description of currently preferred embodiments of the present invention, claims and accompanying drawings.

BRIEF DESCRIPTION OF THE DRAWINGS

So that those having ordinary skill in the art to which the subject invention appertains will more readily understand the subject invention, reference may be had to the drawings, wherein:

FIG. 1a is a frontal perspective view of a syringe-type dispenser embodying the present invention and showing the plunger partially inserted in the syringe body.

FIG. 1b is a rear perspective view of the syringe of FIG. 1a showing the plunger partially inserted in the syringe body.

FIG. 2 is a frontal perspective view of the body of the syringe of FIG. 1a.

FIG. 3 is a rear perspective view of the body of the syringe of FIG. 1a showing the helical steps formed on the inner surface of the upper portion of the body.

FIG. 6a is a frontal perspective view of the plunger of the syringe of FIG. 1a.

FIG. 6b is a rear perspective view of the plunger of the syringe of FIG. 1a.

FIGS. 7a-7c are somewhat schematic, partial cross-sectional views of the syringe of FIG. 1a showing the means for controlling the travel of the plunger within the body, and illustrating the progressive movement of the plunger within the body.

FIG. 8 is a partial, cross-sectional view of the syringe of FIG. 1a including a fusible stopper at the base of the plunger inside the storage chamber of the body.

FIG. 9 is a partial, cross-sectional view of the fusible stopper of the syringe shown in FIG. 8.

FIG. 10 is a cross-sectional view of the fusible stopper and body of FIG. 9.

FIGS. 13 and 14 are cross-sectional views of the syringe of FIG. 11.

DETAILED DESCRIPTION OF THE PREFERRED EMBODIMENTS

Figure 4:
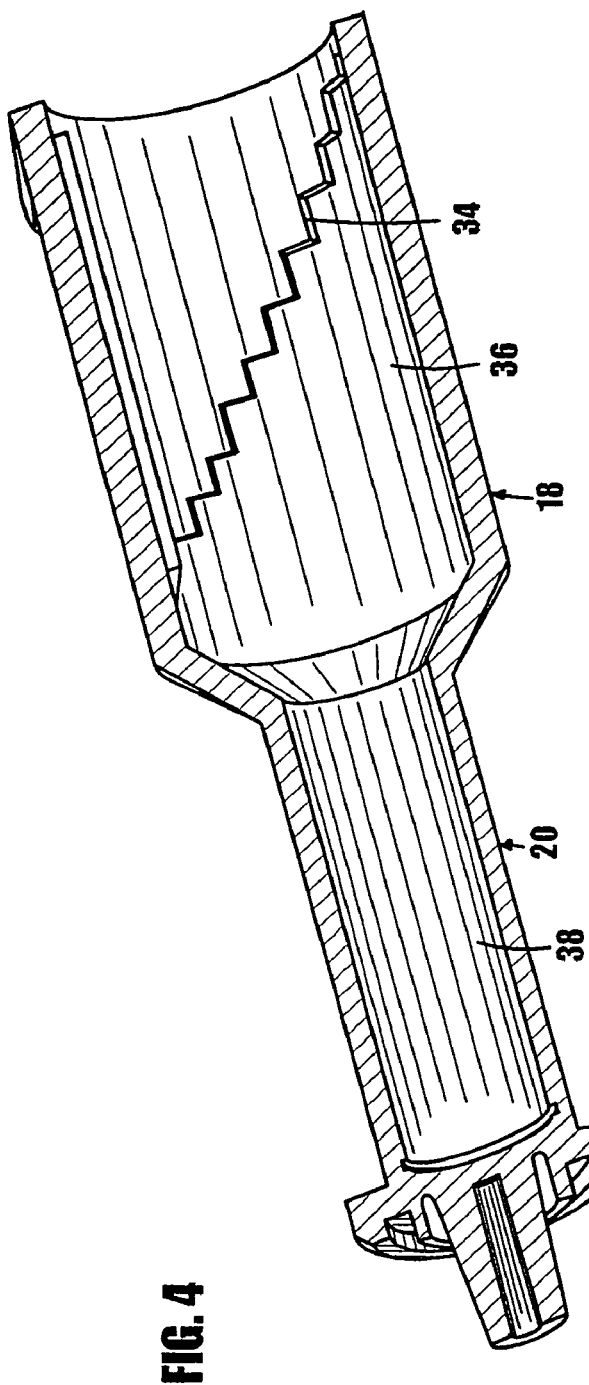
FIG. 4 is a cross-sectional view of a first half of the body taken through section A-A of FIG. 2 and showing the inner walls of the body.

The present invention relates to improved syringes and other dispensers for delivery of substances, such as vaccines, medicaments and other pharmaceutical preparations, cosmetics, food products, glues, or any other substance that can spoil, degrade or react with air. As shown in FIGS. 1a and 1b, the improved syringe-type dispensers include a body 12 and a plunger 14. Means are provided for controlling the travel of the plunger 14 in the syringe body 12 which results in delivery of a precise amount of the substance from the syringe. As shown in FIG. 8, a heat-resealable or other type of stopper is provided at the tip of the plunger to hermetically seal the lower or storage chamber of the syringe and prevent ingress of air or contaminants into the substance in the syringe. In addition, as shown in FIG. 1, the tip of the syringe 16 used for delivery of the substance preferably includes a one-way valve to prevent exposure of the substance to air or other contaminants that otherwise might enter through the tip of the syringe. The preferred embodiments disclosed herein are to be considered exemplary of the principles of the present invention and are not intended to limit the invention to the embodiments described. Various modifications will be apparent to those skilled in the art based on the teachings herein without departing from the spirit or scope of the invention disclosed herein.

As used herein, the term "syringe" or "syringe-type dispenser" means a device having a plunger or like element movable through a chamber containing a substance, such as a liquid, creme, ointment or fluid, in order to inject or deliver the substance into a body, onto the skin, or onto the surface of an object. In addition, the term "plunger" is used herein to mean a device used to exert pressure on the substance contained in the chamber in order to dispense the substance from the device.

Syringe-Type Dispenser With Cam-Like Members for Stepwise Movement

In FIGS. 1a-7c, a first embodiment of a syringe-type dispenser of the present invention is indicated generally by the reference number 10. As shown in FIGS. 1a and 1b, the syringe includes a body 12, a plunger 14 which fits within the syringe body, and a dispensing tip 16 with a one-way valve 54. The body 12 and plunger 14 are preferably made of a moldable plastic, although the invention is not limited in this regard and any appropriate material that is currently or later becomes known to one skilled in the art may be used.

Referring to FIG. 2, the body 12 of the syringe 10 is generally cylindrical. In the embodiment of the invention illustrated in FIG. 2, the syringe body has an upper portion 18 and a lower portion 20, wherein the upper portion has a larger diameter than the lower portion. The upper portion 18 is connected to the lower portion 20 by a tapered portion 22. The invention is not limited in this regard, however, and the upper portion and the lower portion may be any desired dimension or shape. Where the diameters of the upper portion and the lower portion are the same, the tapered portion may be eliminated.

At the outer end of the upper portion 18 opposite the tapered portion 22, means may be provided for gripping the syringe during use. In the embodiment of the invention illustrated in FIG. 2, two opposing flat members 24 protrude perpendicularly from the top of the upper portion of the syringe for gripping the syringe during use. The flat members 24 are preferably approximately triangular in shape, although any desired size or shape may be used.

Figure 5:
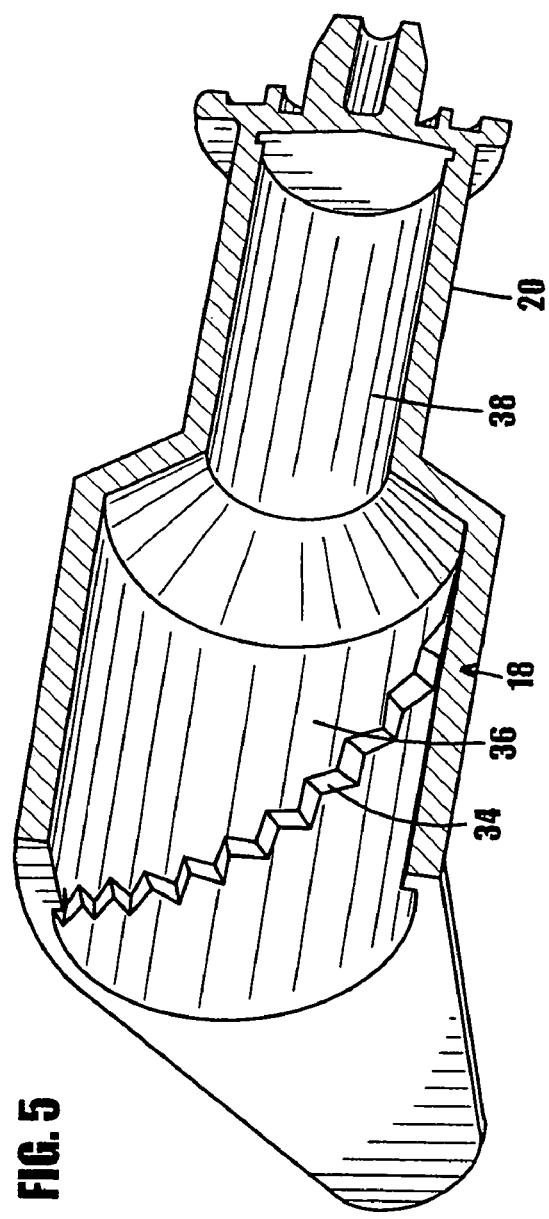
FIG. 5 is a cross-sectional view of a second half of the body taken through section A-A of FIG. 2 and showing the inner walls of the body.

As shown in FIGS. 3-5, the inner walls of the upper portion 18 and the lower portion 20 define cylindrical cavities. The inner wall of the upper portion 18 of the syringe body includes a plurality of steps 34 defining an approximately helical path. As shown in FIGS. 4 and 5, which show opposing halves of the inside of the body of the syringe through section A-A of FIG. 2, the inner wall of the upper portion 18 of the syringe body 12 defines two helical sets of steps 34 formed on opposite sides of the inner wall 36 of the upper portion 18 of the syringe body relative to each other. Each set of steps 34 define an approximately helical path. As shown in FIG. 4, one set of steps 34 is oriented to allow travel along the steps in the direction from the top of the upper portion 18 toward the tapered portion 22 of the syringe body. As shown in FIG. 5, the second set of steps 34 is oriented in the opposite direction relative to the other set of steps to prevent rearward movement of the plunger 14, as described further below.

As shown in FIGS. 7a-7c, the inner wall 38 of the lower portion 20 of the syringe body 12 defines a smooth cylindrical cavity and has an approximately constant inner diameter over the axial length of the lower portion 20. The lower portion 20 of the syringe defines a storage chamber for storing the substance to be dispensed, and is dimensioned to frictionally engage the base of the plunger, as described further below. The inner diameter of the lower portion 20 is preferably constant to ensure that a specific quantity of the medicament or other substance contained therein is dispensed from the syringe for a pre-determined distance of travel by the plunger 14.

At the end of the lower portion of the syringe body, a dispensing tip indicated generally by the reference number 16 is provided to allow the medicament to flow from the syringe as the plunger is inserted into the lower portion. As shown in FIG. 2, in one embodiment of the present invention, the dispensing tip 16 includes a flange 28 that defines an annular U-shaped channel 30. The dispensing tip defines a valve seat in the form of an elongated center shaft or post 32. A plurality of openings (not shown) are provided around the base of the center shaft 32. Each of the plurality of openings communicates with the chamber in the lower portion 20 of the syringe to provide a path to dispense the substance contained in the syringe. A one-way valve 54, such as the one-way valve described below, is included at the dispensing tip to allow controlled delivery of the substance and to hermetically seal the dispensing tip and thereby prevent exposure of the substance in the syringe to air or contaminants. In an alternative embodiment, the center shaft 32 may be provided with a central cylindrical channel that communicates with the chamber in the lower portion of the syringe to provide a path for dispensing the substance contained in the syringe. In other embodiments, other dispensing tip mechanisms that are currently or later become known to those skilled in the art can be fixedly attached to the syringe body. For example, the conventional connection device marketed under the trade name LUER-LOK can be used at the dispensing tip of the syringe to allow attachment of disposable needles. Other needle connection means, such as threaded fittings, elastomeric plugs, or fitted end caps equally may be used to attach a needle to the end of the syringe. The lower end of the syringe body may be shaped or threaded as required to accommodate the selected needle connection means. A cap or other means (not shown) to hermetically seal the dispensing end of the syringe may be used until the needle is connected to the syringe to dispense the medicament or other substance therein.

Referring now to FIGS. 6a and 6b, the plunger 14 comprises a base or tip 40, a lower drive portion 42, and an upper guide portion 44. The front surface 46 of the tip 40 contacts the substance in the storage chamber in the lower portion 20 of the syringe during use. The tip 40 is shaped and dimensioned to fit frictionally into the chamber in the lower portion 20 of the syringe body such that the substance does not escape between the base and the inner surface of the lower portion 20 of the syringe as the tip 40 is inserted into the lower portion 20. The tip 40 is preferably made from a material that will not react with the substance in the syringe, such as any of numerous different moldable, resilient plastics that are currently or later become known for performing the function of the plunger tip described herein. In addition, the plunger tip 40 is preferably made of a resilient material that will hermetically seal the substance within the chamber formed by the body of the syringe, such as the heat resealable stopper described further below, or any of numerous other plunger tip materials that are currently or later become known for performing the function of the plunger tip as described herein.

The drive portion 42 of the plunger 14 is shaped and dimensioned to fit slidingly within the lower portion 20 of the syringe body. The outside diameter of the drive portion 42 is preferably at least slightly less than the inside diameter of the lower portion 20 of the syringe body to reduce the frictional force generated by movement of the plunger within the syringe body. The lower drive portion 42 should be sufficiently long to be fully inserted into the chamber in the lower portion 20 of the syringe body.

The upper guide portion 44 of the plunger 14 defines two diametrically-opposed, cam-like members 48 that extend perpendicularly from the outside surface of the upper guide portion of the plunger. The cam-like members 48 cooperate with the steps 34 formed on the inner wall 36 of the upper portion 18 of the syringe body to provide means for controlling the travel of the plunger into the syringe in a stepwise manner. As shown in FIG. 7a, the cam-like members 48 are preferably located on the upper guide portion 44 such that the base 40 of the plunger is in contact with the medicament or other substance contained in the cavity in the lower portion 20 of the syringe body when the cam-like members 48 engage the steps 34 formed on the inner wall of the upper portion 18 of the syringe body 12. As shown in FIGS. 6a and 7a, the outside surface of the upper guide portion 44 of the plunger 14 preferably includes a plurality of vanes 50 or other support means to provide additional rigidity and/or strength to the plunger during use. The upper guide portion 44 should be sized and dimensioned to fit slidingly within the upper portion 18 of the syringe body. A knob or other griping portion 52 is formed at the upper end of the plunger 14 to provide means for the user to grip the plunger during use.

The syringe 10 preferably includes a one-way valve mechanism at the dispensing tip of the syringe to prevent air or other contaminants from entering the substance contained in the syringe through the dispensing end. Referring to FIGS. 1a, 2 and 7a, the one-way valve is formed by fixing a flexible cover 54 on the dispensing tip 16 of the syringe body. The flexible cover 54 is preferably made of an elastomeric material. The interior surface of the flexible cover 54 is shaped to fit over the flange 28 on the dispensing tip 16 and to fit integrally within the annular U-channel 30 which extends around the dispensing tip. The flexible cover 54 forms an interference fit with the center shaft or valve seat 32 on the dispensing tip. The flexible cover 54 extends from the outer surface of the lower portion 20 of the syringe body 12 to approximately the end of the center shaft 32 of the dispensing tip 16.

At the base of the center shaft, and as shown typically in FIGS. 7a-7c, a plurality of cylindrical openings 56 extend through the dispensing tip. The cylindrical openings 56 communicate with the storage cavity in the lower portion 20 of the syringe and provide a path through which the medicament or other substance in the cavity in the lower portion 20 flows as the plunger 14 is advanced into the lower portion 20 of the syringe. The interference fit between the flexible cover 54 and the center shaft 32 forms a normally-closed valve to hermetically seal the cylindrical openings 56 until a dose of the substance contained in the syringe is delivered. As shown, the portion of the flexible cover 54 that interfaces with the valve seat 32 is preferably tapered such that the thickness is greater near the base of the valve seat and gradually reduces to a lesser thickness near the end of the valve seat to facilitate opening of the valve and the flow of substance therethrough. In addition, the axial length of each of the valve seat 32, valve cover 54 and annular valve opening formed therebetween is sufficiently long to always maintain an annular segment of the valve cover in contact with the valve seat when dispensing substance through valve opening. As can be seen, the valve cover 54 defines an aperture therethrough, the valve seat 32 is received within the aperture to form the normally-closed annular valve opening at the interface between the valve seat and valve cover, and the diameter (or width) of the valve seat is greater than the diameter (or width) of the aperture in the cover to thereby form an interference fit and normally-closed valve opening therebetween. Preferably, the degree of interference between the valve cover aperture and valve seat decreases in the axial direction of the valve seat from the interior toward the exterior of the dispenser to facilitate the flow of substance therethrough.

As may be recognized by those of ordinary skill in the pertinent art based on the teachings herein, the one-way valve of the dispensers may take any of numerous different configurations that are currently or later become known for performing the function of the valve described herein, including any of the one-way valve configurations disclosed in the above-mentioned co-pending patent application Ser. No. 60/403,484.

Referring again to FIGS. 7a, 7b and 7c, to dispense the substance contained in the syringe, the plunger 14 is rotated and depressed until the cam-like members 48 on the upper guide portion each travel down one step 34 along the inner wall of the upper portion of the syringe. As shown in FIG. 7b, as the plunger assembly is rotated, the base 40 of the plunger travels into the lower chamber 20 of the syringe. The base 40 exerts pressure on the substance in the lower chamber of the syringe, which causes the substance to flow into the cylindrical openings 56 at the base of the center shaft 32 in the dispensing tip of the syringe. The pressurized substance, in turn, exerts force on the interior surface of the flexible valve cover 54, causing the flexible cover 54 to be moved away from the center shaft 32, thereby allowing the substance to flow between the interior surface of the flexible cover 54 and the center shaft 32. When the plunger has advanced a pre-determined distance to deliver the desired quantity of the substance contained in the syringe, the force exerted on the substance is released and the flexible cover returns to its normally closed position with the center shaft 32 interfacing the interior surface of the flexible cover 54 to form a hermetic seal. As shown in FIG. 7c, the plunger 14 can be inserted into the syringe in a step-wise manner until the tip 40 of the plunger has traveled completely through the chamber in the lower portion 20 of the syringe and thereby dispensed all of the contained substance therefrom.

The cam-like members 48 cooperate with the steps 34 on the inner surface of the upper portion 18 of the syringe to limit the travel of the plunger. The distance that the base of the plunger travels is thereby precisely controlled, and a precise volume of the medicament or other substance contained in the syringe can be delivered. The volume of medicament delivered is a function of the height of the step and the inside diameter of the lower chamber 20. By setting these two parameters, the volume of substance delivered as a result of travel by the plunger along a single step is precisely controlled and is equal to the cross-sectional area of the inside of the lower chamber of the syringe multiplied by the linear distance traveled by the plunger. For example, if the inside diameter of the lower chamber of the syringe is 6 mm, and it is desired to have movement of the plunger by one step result in delivery of 100 microliters of the substance contained in the syringe, then the step height would be set at approximately 3.54 mm. Where the substance contained in the lower chamber includes an active ingredient and a carrier, the dose of active ingredient delivered may also be a function of the concentration of active ingredient in the carrier. Delivery of a higher dose can be achieved by instructing the user to move the plunger by the number of steps required to deliver the desired amount of the substance. In the example provided above, movement by two steps would result in delivery of 200 microliters, etc.

Stopper to Hermetically Seal Lower Chamber of Syringe-Type Dispenser

In FIGS. 8-10, another syringe-type dispenser embodying the present invention is indicated generally by the reference numeral 110. Many of the components of the syringe 110 are the same as those in the syringe 10 described above with reference to FIGS. 1a-7c, and therefore like reference numerals preceded by the numeral "1" are used to indicate like elements. The primary difference of the syringe 110 in comparison to the syringe 10 is that the syringe 110 includes a fusible stopper 160 at the base of the plunger 114 to hermetically seal the cavity in the lower portion 120 of the syringe 110 and thereby prevent ingress of air or contaminants into the medicament or other substance contained in the syringe.

As shown in FIGS. 8 and 9, the fusible stopper 160 is formed at the end of the plunger 114 and includes a resilient base 162 made of vulcanized rubber or other material which is known to those of ordinary skill in the pertinent art, and acceptable for use in the manufacture of stoppers placed in contact with or otherwise exposed to the substance to be contained within the syringe. The lower portion 164 of the base 162 of the fusible stopper 160 defines a peripheral sealing surface 166 that is shaped and dimensioned to slidably and frictionally engage the inner wall of the lower portion 120 of the syringe body 112. The base 162 of the fusible stopper further defines a peripheral wall 168 extending from the lower portion 164 of the base 162. The peripheral wall 168 defines an outer diameter slightly less than that of the sealing surface 166 and the inner diameter of the syringe body 112 to reduce the friction between the fusible stopper and the body of the syringe upon movement of the plunger therein.

At the upper end of the peripheral wall 168, an annular raised portion or protuberance 170 dimensioned to be frictionally received within the lower portion 120 of the syringe body 112 further seals the plunger assembly 114 and prevents air from contacting the medicament or other substance contained in the syringe. At the top of the peripheral wall 168, a wedge-shaped flexible annular flap 172 is present, which is shaped and dimensioned to be flexible and to contact the inside of the syringe body 112 to form the annular one-way valve. The tip 174 of the flexible flap 172 makes contact with the inside of the syringe body 112 when the plunger is in its fully-retracted position. As shown in FIG. 9, in the illustrated embodiment of the invention, the inside diameter of the syringe body 112 in the area of the flexible flap 172 may be slightly larger than the inside diameter of the syringe at the base 164 of the fusible stopper 160 when the plunger is in the illustrated retracted position. As the plunger is advanced into the syringe body 112, the inside diameter of the body of the syringe body 112 decreases slightly, causing the flexible flap 172 to make increased contact with the syringe body, thereby sealing the lower portion of the syringe from ingress of air.

As shown in FIGS. 9 and 10, the inner wall of the lower portion 120 of the syringe body 112 is provided with a plurality of axially-elongated grooves 176 angularly spaced relative to each other about the axis of the syringe. The grooves 176 are formed in the inner wall of the lower portion 120 and extend in an axial direction from below the base 162 of the fusible stopper 160 when in the fully-retracted position and upwardly beyond the annular protuberance 170. As described below, the grooves 176 allow air contained in the syringe to escape as the syringe is filled with a medicament or other substance.

A resealable member 178 is contained within the upper recess 179 of the base 160 defined by the peripheral wall 168. The resealable member 178 is received within the upper recess 179 formed in the peripheral wall 168 of the base 160, and is secured in place by the end of the drive portion 142 of the plunger. The interior surface of the peripheral wall 168 of the fusible stopper is shaped with an annular groove 180. An annular flange 181 is formed at the end of the drive portion 142 of the plunger 114 and is dimensioned and shaped complementary to the annular groove 180 on the interior surface of the peripheral wall 168. Accordingly, the annular flange 181 is pressed, snapped or otherwise received within the annular groove 180 to fixedly secure the fusible stopper 160 to the drive portion 142. A second annular flange 182 is axially spaced relative to the first annular flange 181 to capture and retain the base 162 and the resealable stopper 160 on the drive portion 142. In the embodiment of the invention shown in FIGS. 8 and 9, the drive portion 142 is in the form of a hollow tube to allow insertion of a filling needle to fill the chamber 120, and allow resealing of the needle hole after filling, as described in commonly assigned U.S. patent application Ser. No. 09/781,846, filed Feb. 12, 2001, entitled "Medicament Vial Having A Heat-Sealable Cap, And Apparatus And Method For Filling The Vial", which is hereby expressly incorporated by reference as part of the present disclosure.

The resealable member 178 is preferably made of a resilient polymeric material, such as a blend of the polymeric material sold by Shell Oil Co. under the registered trademark KRATON® and a low-density polyethylene, such as the polyethylene sold by Dow Chemical Co. under the trademarks ENGAGE™ or EXACT™. However, any other appropriate material known to one skilled in the art may be used. An important feature of the resealable member 178 is that it be resealable to form a gas tight seal after inserting a needle or like injection member through the resealable member. Preferably, the resealable member 178 can be sealed by heating the area punctured by the needle in a manner known to those skilled in the pertinent art, such as, for example, the method described in the above-mentioned co-pending patent application.

To fill the lower portion 120 of the syringe with the desired substance, a hypodermic needle, a double lumen needle, or other type of injection member is inserted through the resealable member 178 and the resilient base 162 of the fusible stopper 160 in order to dispense the desired substance into the lower portion 120 of the syringe. As the medicament is injected into the lower portion of the syringe, the air within the lower portion is displaced by the substance and forced out. The air escapes through the plurality of grooves 176 formed in the inner wall of the syringe body 112. At the top of the peripheral wall 168, the force of the escaping air causes the flexible flap 172 of the one-way valve to move away from the inner wall of the syringe body, allowing the air to pass out of the syringe body. When the syringe has been filled with medicament or other substance, the flexible flap 172 returns to its normal position in contact with the syringe body 112, thereby forming a hermetic seal to prevent air from entering the syringe and contacting the medicament or other substance therein. As the plunger is inserted into the lower portion 120 of the syringe, the grooves 140 terminate, and the lower portion is further sealed by the peripheral sealing surface 166 and the annular protuberance 170 on the resealable stopper 160.

Figure 41:
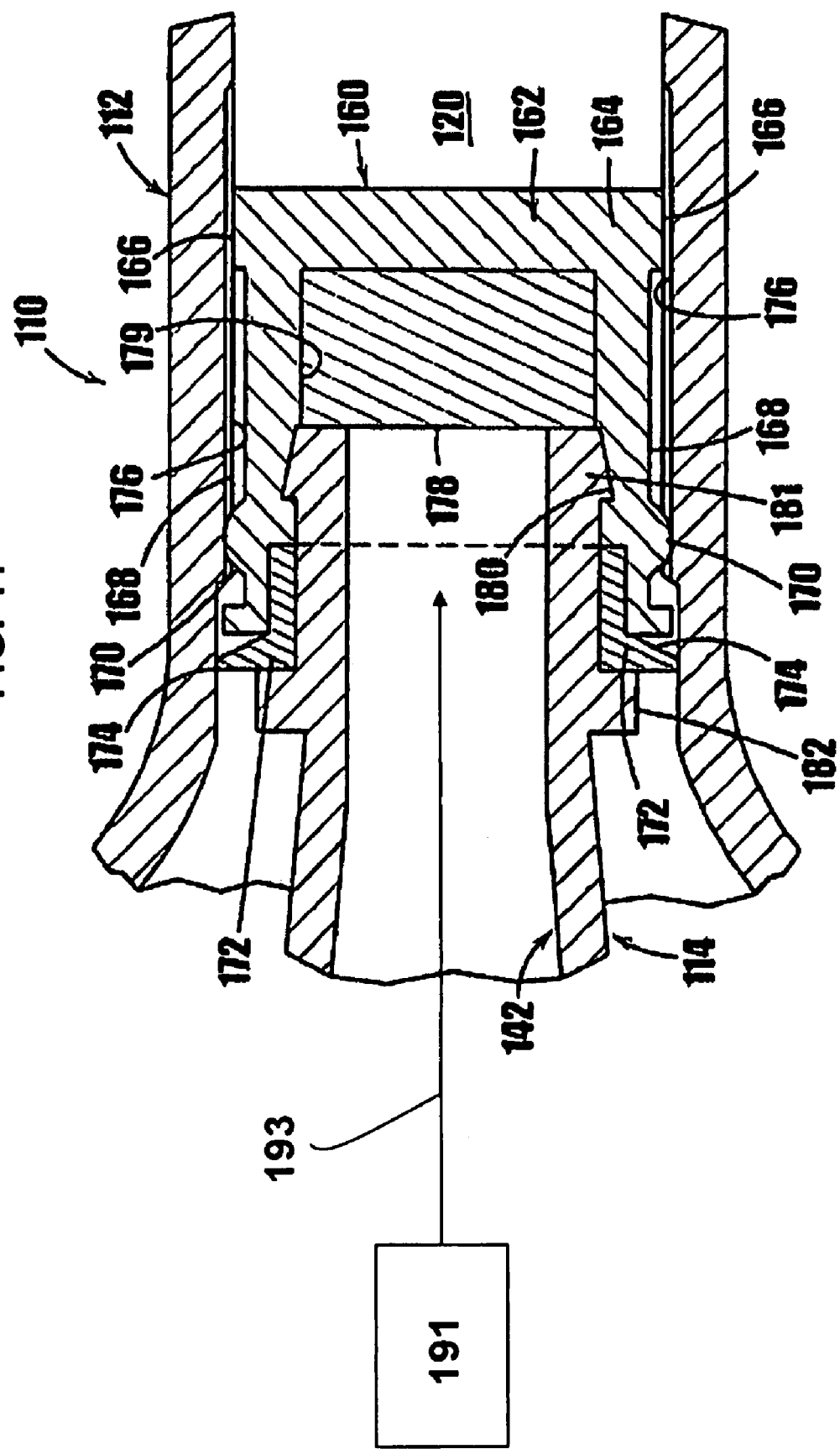
FIG. 41 is a partial cross sectional view of the fusible stopper of the syringe shown in FIG. 8, and an energy source for sealing a resealable member.

After the syringe 110 is filled with the medicament or other substance, the resealable member 178 is heated to fuse the hole formed by the needle or other filling member. In a currently preferred embodiment of the present invention, a laser 191 (shown for example in FIG. 41) or other radiation source is used to sterilize the surface of the resealable member prior to filling, and to seal the hole remaining after filling. Preferably, the syringe is filled in a sterile filling machine, and in accordance with the method disclosed in the co-pending patent application incorporated by reference above. The laser allows sufficient energy 193 to be directed to the resealable member in the fusible stopper while avoiding heating of the medicament or other substance in the syringe. Other methods of heating the resealable member that are currently or later become known to those skilled in the art may be used depending on the heat sensitivity of the substance contained in the syringe and/or other factors. Because the syringe is hermetically sealed after it is filled with medicament or other substance, the syringe may be stored for extended periods of time without spoilage due to ingress of air and without the addition of preservatives to prevent such spoilage.

In certain embodiments of the present invention, at least a portion of the resealable stopper is formed of a thermoplastic material defining a needle penetration region that is pierceable with a needle to form a needle aperture therethrough, and is heat resealable to hermetically seal the needle aperture by applying laser radiation at a predetermined wavelength and power thereto. In an alternative embodiment of the present invention, the entire body of the stopper is formed of the thermoplastic material. In another embodiment of the invention as described above, an overlying portion of the stopper if formed of the fusible thermoplastic material, and an underlying portion of the stopper is formed of an infusible material, such as vulcanized rubber. Preferably, each thermoplastic portion or body defines (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region (i.e., without creating an irreversible change in molecular structure or chemical properties of the material). In one embodiment, the predetermined time period is approximately 2 seconds, is preferably less than or equal to about 1.5 seconds, and most preferably is less than or equal to about 1 second. Also in this embodiment, the predetermined wavelength of the laser radiation is about 980 nm, and the predetermined power of each laser is preferably less than about 30 Watts, and most preferably less than or equal to about 10 Watts, or within the range of about 8 to about 10 Watts. Also in this embodiment, the predetermined color of the material is gray, and the predetermined opacity is defined by a dark gray colorant added to the stopper material in an amount within the range of about 0.3% to about 0.6% by weight.

In addition, the thermoplastic material may be a blend of a first material that is preferably a styrene block copolymer, such as the materials sold under either the trademarks KRATON or DYNAFLEX, and a second material that is preferably an olefin, such as the materials sold under either the trademarks ENGAGE or EXACT. In one embodiment of the present invention, the first and second materials are blended within the range of about 50:50 by weight to about 95:5 by weight (i.e., first material : second material). In one such exemplary embodiment, the blend of first and second materials is about 50:50 by weight. The benefits of such blends over the first material by itself are improved water or vapor barrier properties, and thus improved product shelf life; improved heat sealability; a reduced coefficient of friction; improved moldability or mold flow rates; and a reduction in hystereses losses. As may be recognized by those skilled in the pertinent art based on the teachings herein, these numbers and materials are only exemplary, however, and may be changed if desired or otherwise required in a particular system.

Threaded Syringe-Type Dispenser to Control Movement of Plunger

In FIGS. 11-17, another syringe-type dispenser embodying the present invention is indicated generally by the reference numeral 210. Many components of the syringe 210 are the same as those in the syringes 10 and 110 described above, and therefore like reference numerals preceded by the numeral "2", or preceded by the numeral "2" instead of the numeral "1", are used to indicate like elements. The primary difference of the syringe 210 in comparison to the syringes 10 and 110 is that the syringe 210 includes a threaded plunger and partially threaded upper syringe portion as the means for controlling the movement of the plunger in the syringe.

Figure 11:
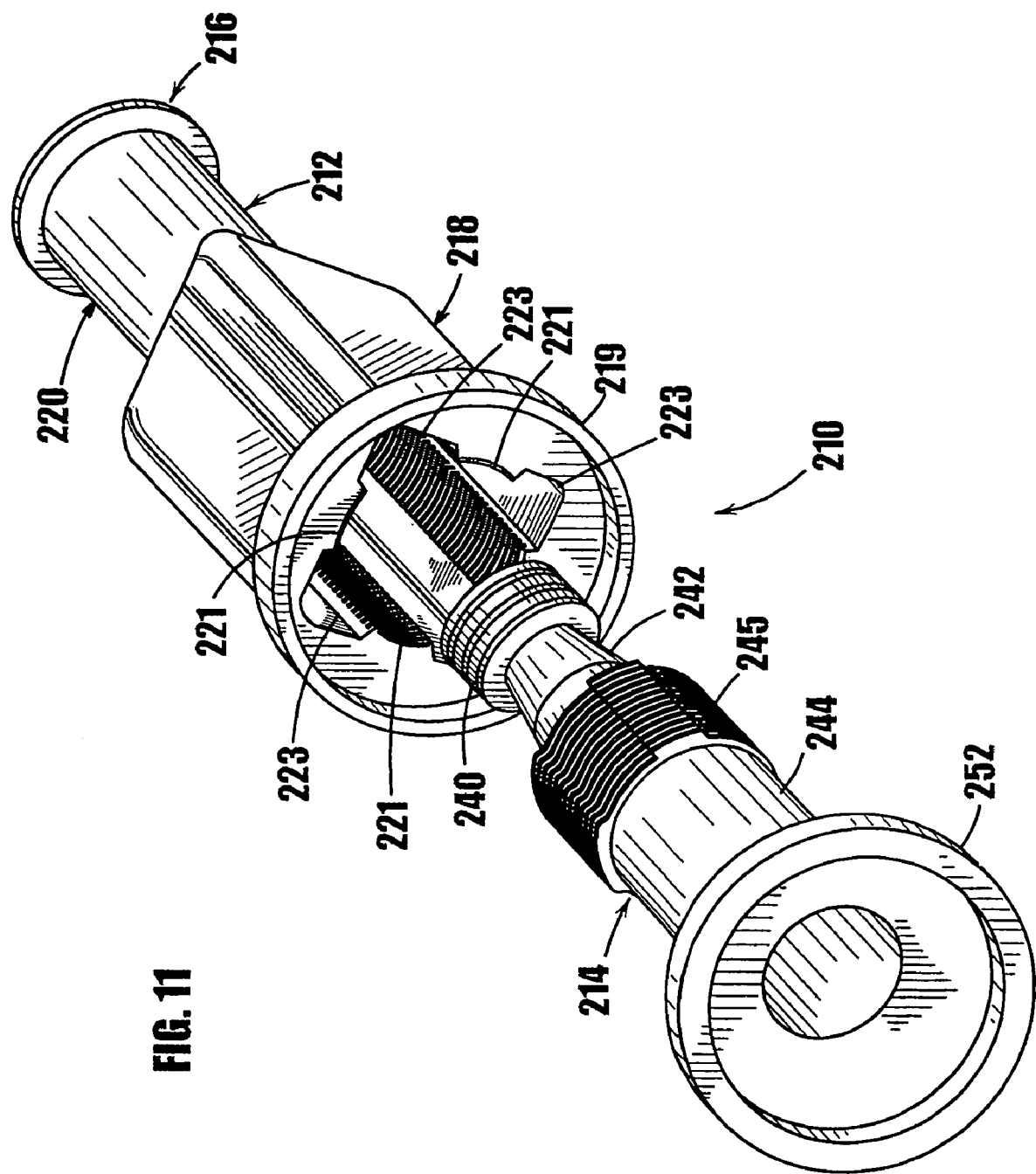
FIG. 11 is a perspective view of a second embodiment of a syringe-type dispenser of the present invention illustrating the body including partially threaded portions and a plunger with a threaded upper guide portion for controlling travel of the plunger.
Figure 12:
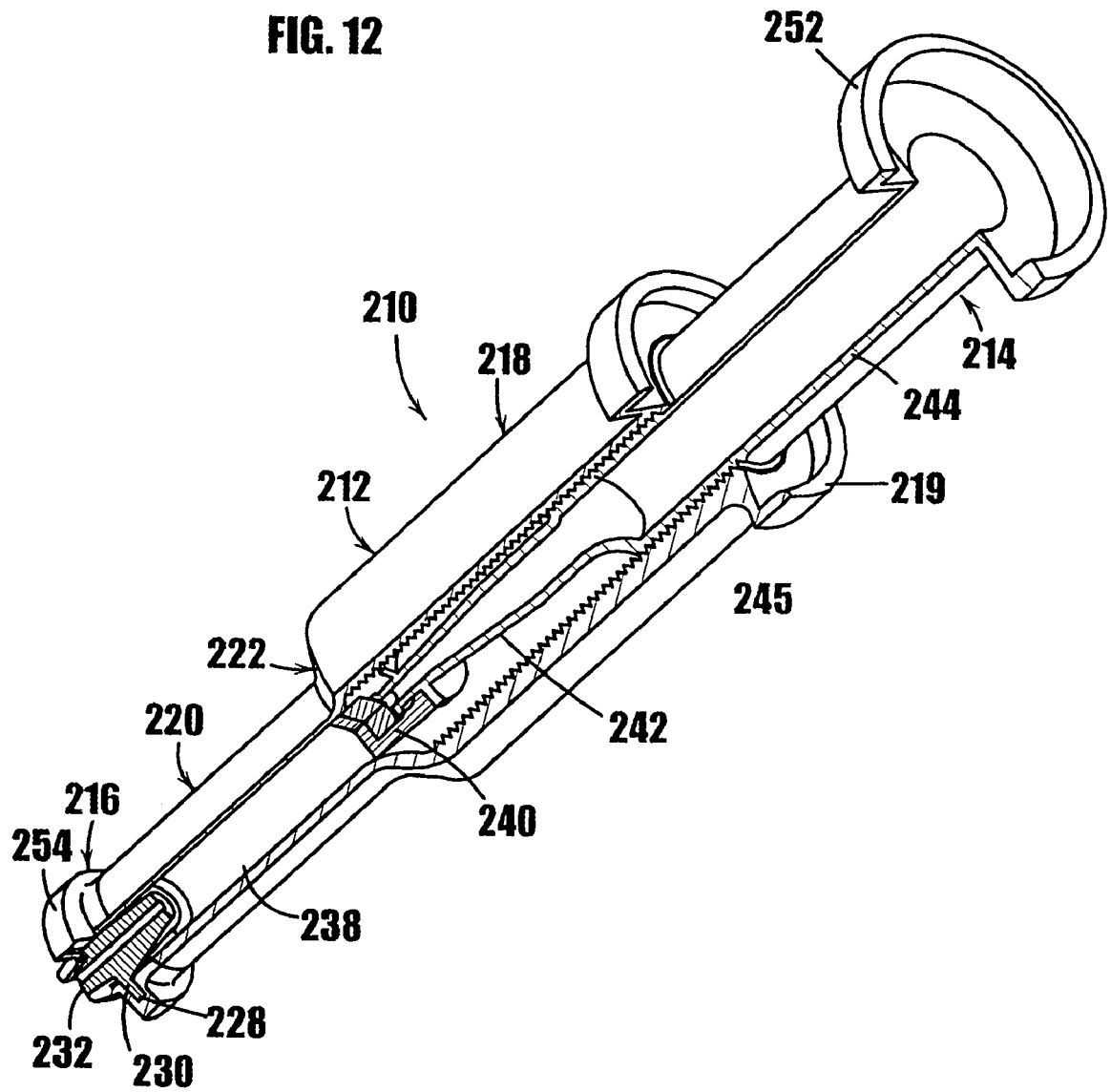
FIG. 12 is a partially broken away, perspective view of the syringe of FIG. 11.

As shown in FIGS. 11-14, the syringe 210 includes a syringe body 212, a plunger 214 which fits within the syringe body, and a dispensing tip 216 with a one-way valve. As shown in FIGS. 11 and 12, the body 212 of the syringe has an upper portion 218 and a lower portion 220. The outside of the upper portion 218 is square shaped to permit the syringe to be easily gripped and allow lateral movement of the body walls upon rotating the plunger, as described further below. The invention is not limited in this regard, however, and the outside of the upper portion of the body may be any desired shape. The lower portion 220 of the syringe is generally cylindrical. As shown in FIGS. 13 and 14, the upper portion 218 is connected to the lower portion 220 by a tapered portion 222. At the outer end of the upper portion 218, means may be provided to grip the syringe, such as a flange 219 or other gripping means.

Figure 15:
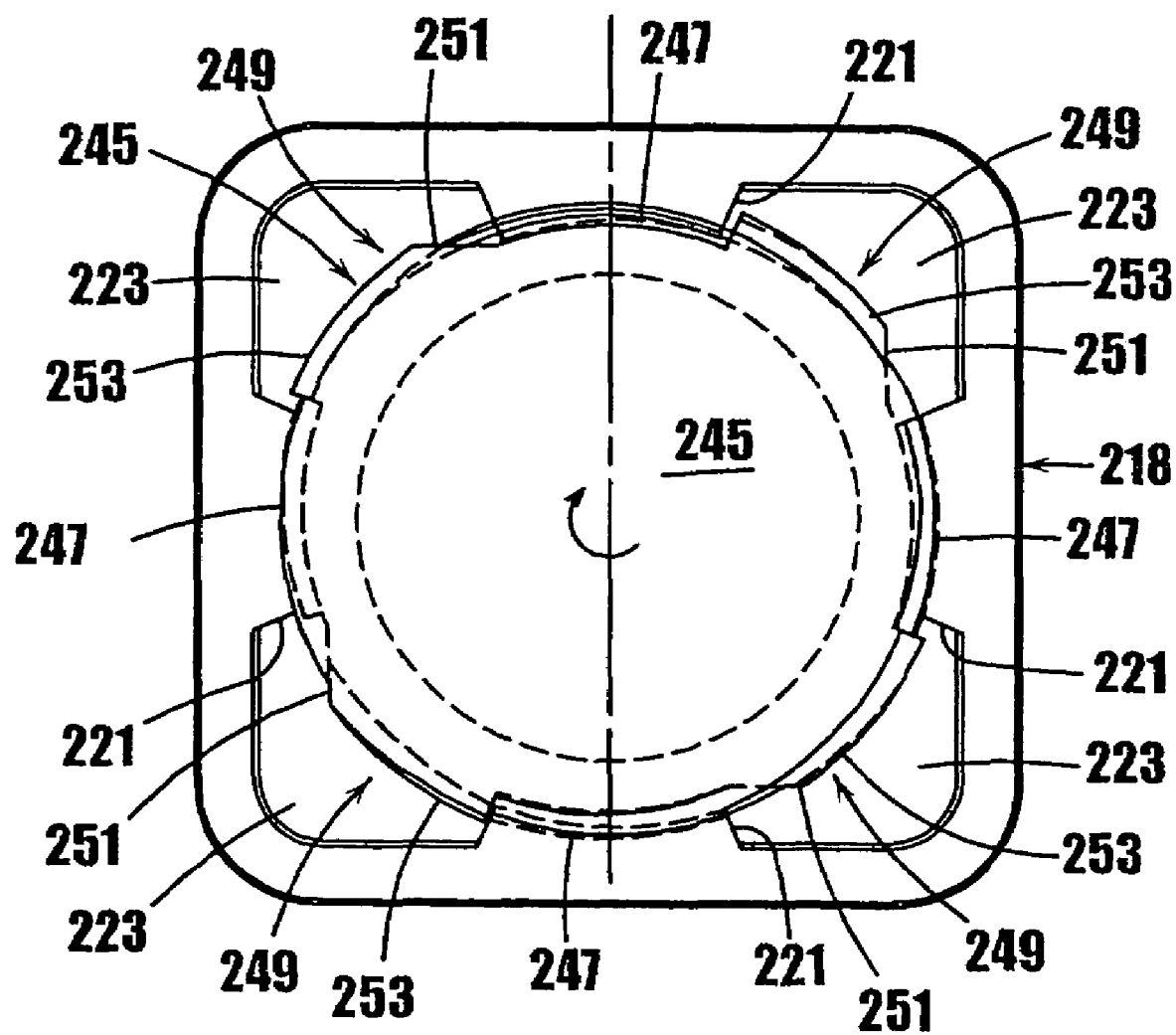
FIG. 15 is a cross-sectional view of the body and the upper guide portion of the plunger of FIG. 11.

Referring to FIGS. 11 and 15, the inner wall of the upper portion 218 of the syringe 210 includes a plurality of partial threads 221. As shown in FIG. 15, each of the partial threads 221 is generally defined by an arc of the circle representing the thread diameter of a fully threaded inner cylinder. The partial threads 221 are equally spaced relative to each other, and each of the partial threads 221 has the same inner and outer thread diameter. In the preferred embodiment shown in FIGS. 11 and 15, each of the partial threads occupies approximately ⅛ of the circumference of a fully threaded inner cylinder. The invention is not limited in this regard, however, and each of the partial threads can occupy any desired portion of the full circumference of a fully threaded inner cylinder in accordance with the teachings herein. Also, any number of partial threads can be used, provided there are at least two opposing partial thread portions for threadedly engaging the plunger, as described further below.

As shown in FIGS. 11 and 15, a plurality of unthreaded sections 223 are located in the upper portion 218 of the syringe between the partial threads 221. The unthreaded sections 223 have a larger diameter (or lateral or radial extent) than the outside diameter of the partial threads 221, and preferably have a larger diameter (or lateral or radial extent) than the largest diameter thread on the plunger 214, as described further below. In the embodiment shown in FIGS. 11 and 15, the upper portion 218 of the syringe 210 has a square shape with the partial threads 221 centered on each of the four inner faces of the upper portion 218 of the syringe, and the unthreaded sections 223 are generally located in the corners of the square-shaped body section. As may be recognized by those of ordinary skill in the pertinent art based on the teachings herein, the inner surface of the upper portion 218 of the syringe 210 may have any desired shape provided that the partial threads on the inner surface define arcs of a circle of the desired diameter.

Referring to FIGS. 12-14, the inner wall 238 of the lower portion 220 of the syringe body 212 defines a smooth cylindrical cavity and has an approximately constant inner diameter over the axial length of the lower portion 220. The lower portion 220 of the syringe is used to contain the substance to be dispensed, and is dimensioned to frictionally engage the tip of the plunger described further below. The inner diameter of the lower portion 220 is preferably constant to ensure that a specific quantity of the medicament or other substance contained therein is dispensed from the syringe for a pre-determined distance of travel by the plunger 214.

At the end of the lower portion of the syringe body, a dispensing tip indicated generally by the reference number 216 is provided to allow the substance contained in the lower portion 220 of the syringe to flow from the syringe as the plunger 214 is inserted into the lower portion. In a currently preferred embodiment, the dispensing tip 216 includes a flange 228 that defines an annular U-shaped channel 230. The dispensing tip 216 includes an elongated center shaft or post 232. A plurality of cylindrical openings 256 each communicates with the chamber in the lower portion 220 of the syringe to provide a path to dispense the substance contained in the syringe.

The syringe preferably includes a one-way valve mechanism at the dispensing tip of the syringe to prevent air or other contaminants from entering the substance contained in the syringe through the dispensing tip. Referring to FIGS. 12 and 13, the one-way valve is formed by fixing a flexible cover 254 on the dispensing tip 216 of the syringe body. The flexible cover is preferably made of an elastomeric material. The interior surface of the flexible cover is shaped to fit over the flange 228 on the dispensing tip 216 and to fit integrally within the annular U-channel 230 which extends around the dispensing tip. The flexible cover 254 forms an interference fit with the center shaft 232 on the dispensing tip. The flexible cover 254 extends from the outer surface of the lower portion 220 of the syringe body 212 to approximately the end of the center shaft 232 of the dispensing tip 216.

At the base of the center shaft 232, and as shown best in FIGS. 13 and 14, the plurality of cylindrical openings 256 extend through the dispensing tip. The cylindrical openings 256 communicate with the cavity in the lower portion 220 of the syringe and provide a path through which the substance in the cavity in the lower portion 220 flows as the plunger 214 is advanced into the lower portion 220 of the syringe. The interference fit between the flexible cover 254 and the center shaft 232 forms a normally-closed valve to hermetically seal the cylindrical openings 256 until a dose of the substance contained in the syringe is delivered. The portion of the flexible cover 254 that interfaces with the center shaft 232 may be tapered such that the thickness is greater near the base of the center shaft and gradually reduces to a lesser thickness near the end of the center shaft.

In an alternative embodiment of the invention, the one-way valve may be omitted. The center shaft 232 may be provided with a central cylindrical channel that communicates with the cavity in the lower portion 220 of the syringe to provide a path for dispensing the substance contained in the syringe. In other embodiments of the invention, other appropriate dispensing tip mechanisms known to those skilled in the art can be fixedly attached to the syringe body. For example, the conventional connection device marketed under the trade name LUER-LOK can be used at the dispensing tip of the syringe to allow attachment of disposable needles. Other needle connection means, such as threaded fittings, elastomeric plugs, or fitted end caps equally may be used to attach a needle to the end of the syringe. The lower end of the syringe body may be shaped or threaded as required to accommodate the selected needle connection means. A cap or other means (not shown) to hermetically seal the dispensing end of the syringe may be used until the needle is connected to the syringe to dispense the medicament or other substance therein.

Figure 16:
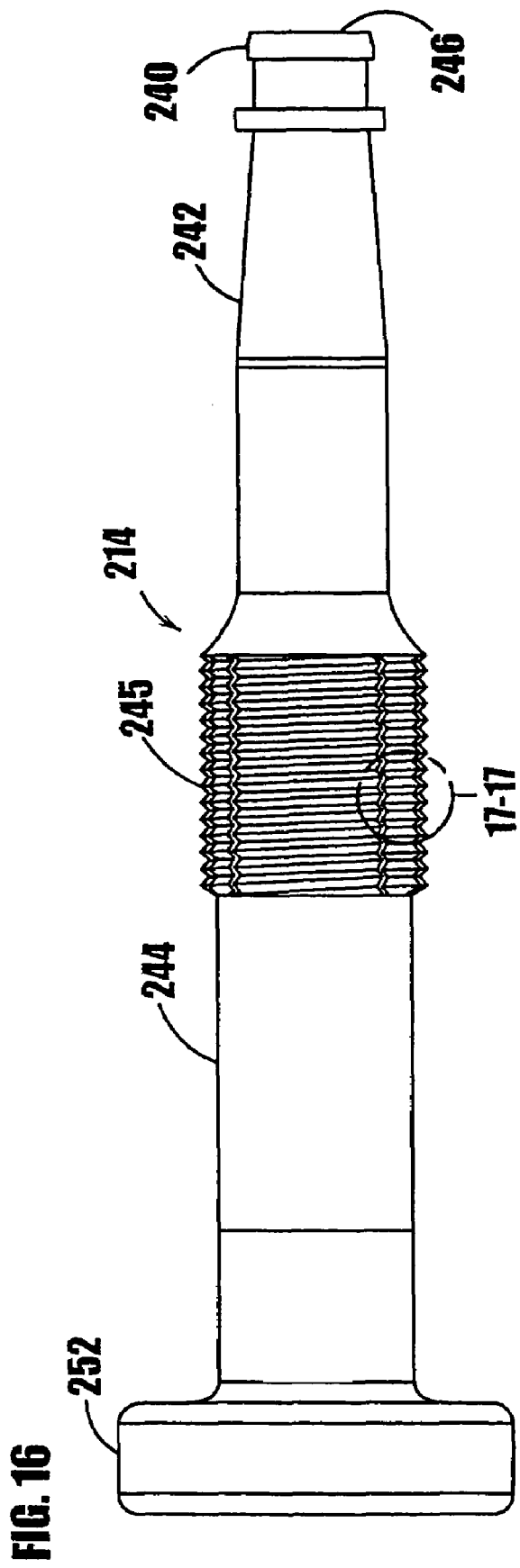
FIG. 16 is a side elevational view of the plunger of the syringe of FIG. 11.

Referring now to FIGS. 11 and 16, the plunger 214 comprises a tip 240, a lower drive portion 242 and an upper guide portion 244. The face surface 246 of the tip 240 contacts the medicament or other substance in the cavity in the lower portion 220 of the syringe during use. The tip 240 is shaped and dimensioned to fit frictionally into the cavity in the lower portion 220 of the syringe body such that the medicament or other substance dose not escape between the tip 240 and the inner surface of the lower portion 220 of the syringe as the tip 240 is inserted into the lower portion 220. The tip 240 may be made of any suitable material that is currently or later becomes known to those skilled in the art that will not react with the medicament or other substance contained in the syringe. If desired, a fusible stopper, such as the fusible stopper described in detail above, can be fixedly attached to the plunger to hermetically seal the cavity in the lower portion.

The drive portion 242 of the plunger 214 is shaped and dimensioned to fit slidingly within the lower portion 220 of the syringe body. The outside diameter of the drive portion 242 is preferably at least slightly less than the inside diameter of the lower portion 220 of the syringe body to reduce the frictional force generated by movement of the plunger within the syringe body. The drive portion 242 should be sufficiently long to be fully inserted into the cavity in the lower portion 220 of the syringe body when the plunger is in its fully inserted position.

Figure 17:
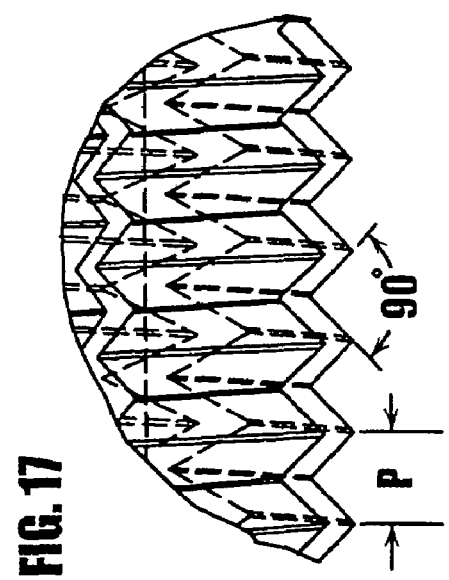
FIG. 17 is a partially enlarged elevational view of FIG. 16 showing a portion of the threads on the upper guide portion of the plunger.

Referring to FIGS. 11, 12 and 16, the upper guide portion 244 of the plunger has a threaded section 245 with a thread pitch complementary to the pitch of the partial threads 221 on the inner wall of the upper portion 218 of the syringe. As shown in FIG. 17, in a preferred embodiment wherein the syringe body and plunger are made of a moldable plastic, the thread pitch, P, is approximately 0.8 mm and the thread angle is approximately 90°. When the syringe body and the plunger are made of molded plastic, a thread angle of approximately 90° permits easier removal of the molded parts from the molds.

As shown in FIG. 15, the threads 245 on the upper guide structure have a variable thread diameter. The threads on the upper guide structure are divided generally into eight sections. In four of the eight sections, indicated generally by the reference number 247, the threads have a thread diameter and pitch approximately equal and complementary to the thread diameter and pitch of the partial threads 221 on the inner wall of the upper portion 218 of the syringe. These four sections each occupy approximately ⅛ of the circumference of the upper guide portion of the plunger, and are spaced equally apart relative to each other.

In the remaining four sections of threads on the plunger, indicated generally by the reference number 249, each of the sections of threads have two regions defined by the thread diameter in each region. In the first region, indicated generally by the reference number 251, the plunger threads have a gradually increasing thread diameter, beginning with a thread diameter equal to the thread diameter of the partial threads in the upper portion 218 of the syringe, and ending at a point where the thread diameter on the plunger first reaches its maximum diameter. In the second region 253, the plunger threads have a constant diameter that is larger than the diameter of partial threads 221 in the upper portion 218 of the syringe. Each of the four sections of varying diameter threads occupies approximately ⅛ of the circumference of the upper guide portion of the plunger. A knob or other gripping portion 252 is formed at the upper end of the plunger 214 to provide means for the user to grip the plunger during use.

The threads 247, 249 on the upper guide portion of the plunger cooperate with the partial threads 221 formed on the inner wall of the upper portion 218 of the syringe body to provide means for controlling the travel of the plunger into the syringe in a stepwise manner. As shown in FIG. 13, after the syringe has been filled with the substance to be dispensed, the plunger is positioned such that the tip 240 of the plunger is in contact with the medicament or other substance contained in the chamber in the lower portion 220 of the syringe body with the threads 247 fully engaged in the partial threads 221 in the upper portion 218 of the syringe. The plunger 214 is positioned such that the partial threads 221 in the syringe body are engaged only by the four sections of threads 247 on the upper guide portion 244 that have a thread diameter equal to the thread diameter of the partial threads 221 in the upper guide portion. As shown in FIG. 15, in this position, the largest diameter threads 249 on the upper guide portion 244 of the plunger are located in the unthreaded sections 223 of the upper portion 218 of the syringe body between the partial threads 221.

To deliver a metered dose of the substance from the syringe, and as indicated by the arrow in FIG. 15, the plunger 214 is rotated in the clockwise direction causing the plunger to travel into the syringe body. As the plunger 214 is rotated, the partial threads 221 in the upper portion 218 of the syringe are each progressively engaged by the larger diameter threads 251, 253 on the upper guide portion 244 of the plunger 214. Because the threads on the plunger 214 progressively increase in diameter as the plunger is rotated in the clockwise direction, the upper portion 218 of the syringe body 212 is forced to expand, and progressively greater force must be applied to the plunger to cause it to rotate.

In the embodiment shown in FIGS. 11-17, when the plunger 214 completes rotation through ¼ of a full revolution, the largest diameter threads 253 on the upper guide portion 244 of the plunger disengage from the partial threads 221 in the upper portion 218 of the syringe body, and the smaller diameter threads 247 on the upper guide portion 244 of the plunger are completely engaged in the partial threads 221 in the syringe body. The upper portion 218 of the syringe body rapidly returns to its original dimension, and the plunger is locked in position until sufficient force is applied to the plunger to cause the larger diameter threads on the plunger to engage and move through the partial threads on the syringe body. In addition, the plunger cannot be rotated in the opposite direction (i.e., counter-clockwise) because the trailing edge of each large diameter threaded portion 253 will engage the adjacent edge of each threaded portion 221 of the body and thereby prevent such movement.

By controlling the pitch of the partial threads in the syringe body and the pitch of the complementary threads on the plunger, the amount of medicament or other substance delivered for each ¼ turn of the plunger can be precisely controlled. For example, in a preferred embodiment, the lower chamber 220 of the syringe has an approximately 6.18 mm inside diameter, and the threaded portions have a thread pitch of approximately 0.8 mm. Rotation of the plunger by ¼ turn causes the plunger to displace a volume of approximately 6 microliters from the lower portion of the syringe. Accordingly, approximately 6 microliters of the substance contained in the syringe is delivered through the dispensing tip when the plunger is rotated ¼ turn. Greater doses of the substance can be delivered by increasing the number of ¼ rotations of the plunger, i.e. ½ rotation will deliver 12 microliters, ¾ rotations will deliver 18 microliters, one full rotation will deliver 24 microliters, etc.

Syringe-Type Dispenser With Elastomeric Outer Body

In FIGS. 18-21, another syringe-type dispenser is indicated generally by the reference numeral 310. Many of the components of the syringe 310 are the same as those in the syringes 10, 110 and 210 described above, and therefore like reference numerals preceded by the numeral "3", or preceded by the numeral "3" instead of the numerals "1" or "2", are used to indicate like elements. The primary differences in the syringe 310 in comparison to the syringes 10, 110 and 210 is that the syringe 310 includes a threaded plunger and threaded elements in the upper syringe portion as the means for controlling the movement of the plunger, and the syringe 310 includes an outer elastomeric cover.

Figure 18:
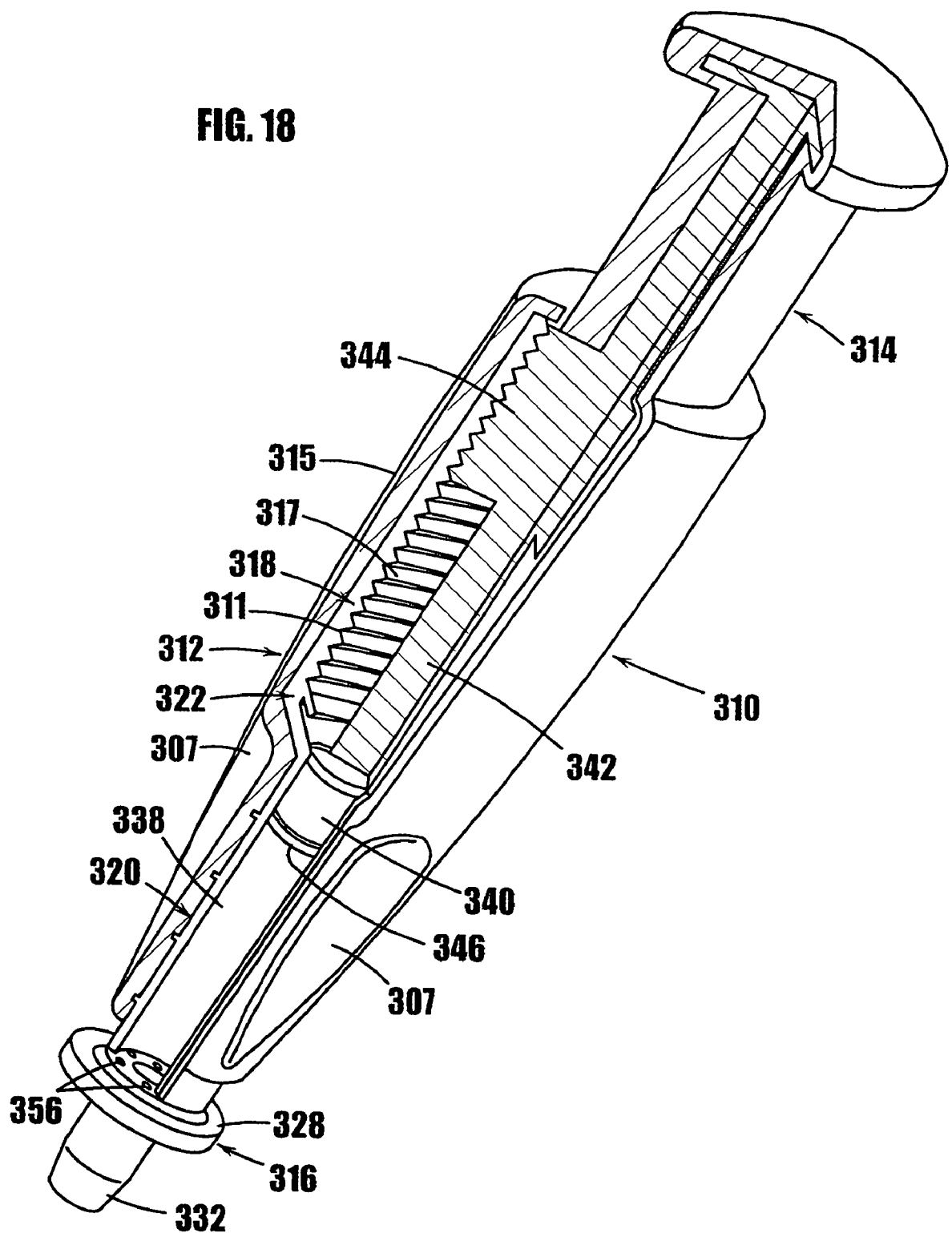
FIG. 18 is a partially broken away, perspective view of a third embodiment of a syringe-type dispenser of the present invention having an elastomeric outer cover.
Figure 19:
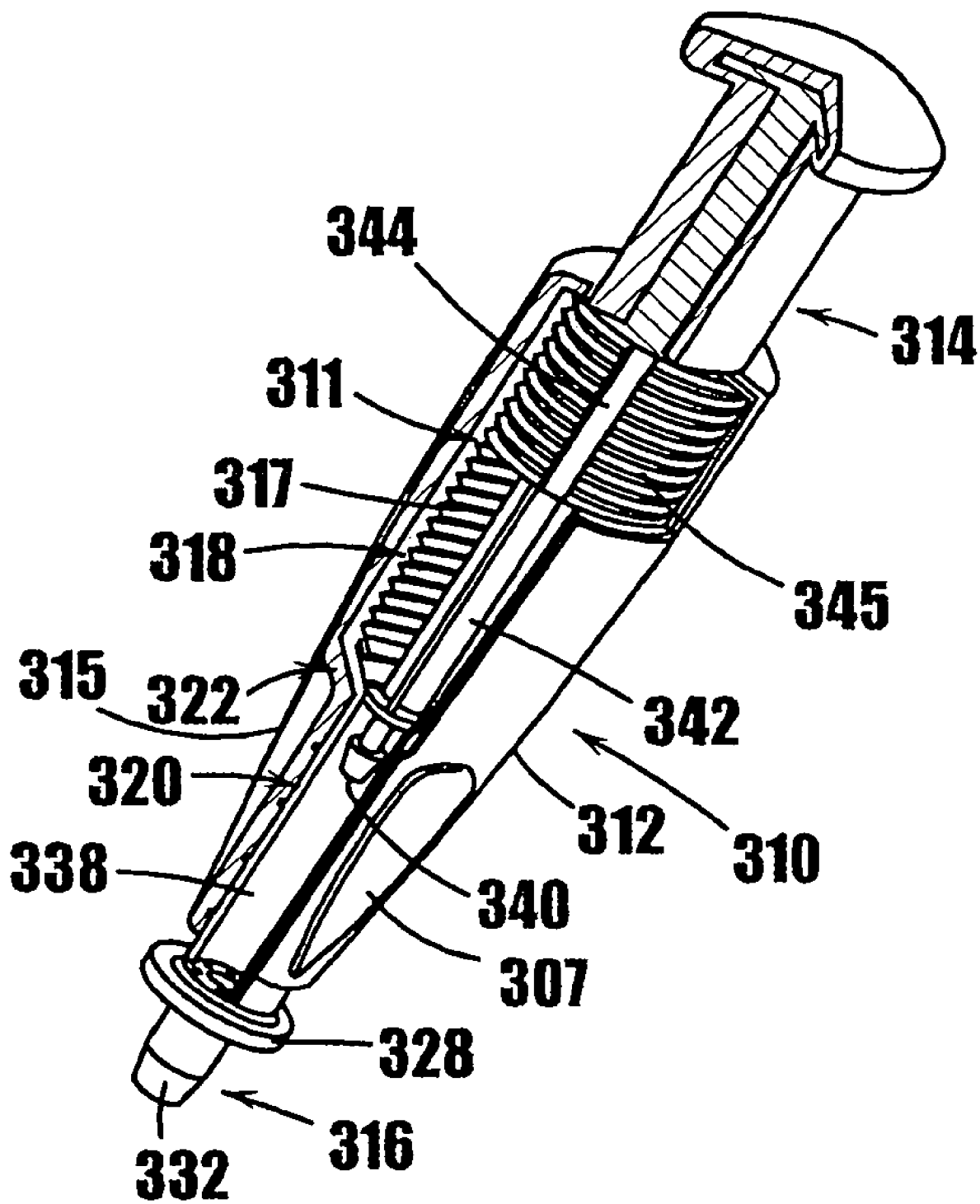
FIG. 19 is a perspective view of the syringe of FIG. 18, with a portion partially broken away to show the elastomeric outer cover, threaded elements and upper guide portion of the plunger.

As shown in FIGS. 18-19, the syringe 310 comprises a syringe body 312, a plunger 314 which fits within the syringe body, and a dispensing tip 316. The syringe body 312 includes an inner portion 311 and an elastomeric outer cover 315 which encases the outer surface of the inner portion 311. The inner portion 311 is preferably made from molded plastic. The inner portion 311 of the syringe body 312 includes an upper portion 318 and a lower portion 320, wherein the upper portion has a larger diameter than the lower portion. The upper portion 318 is connected to the lower portion 320 by a tapered portion 322. The dispenser is not limited in this regard, however, and the upper portion and the lower portion may be any desired shape or diameter. Where the diameters of the upper portion and the lower portion are the same, the tapered portion may be eliminated.

Figure 20:
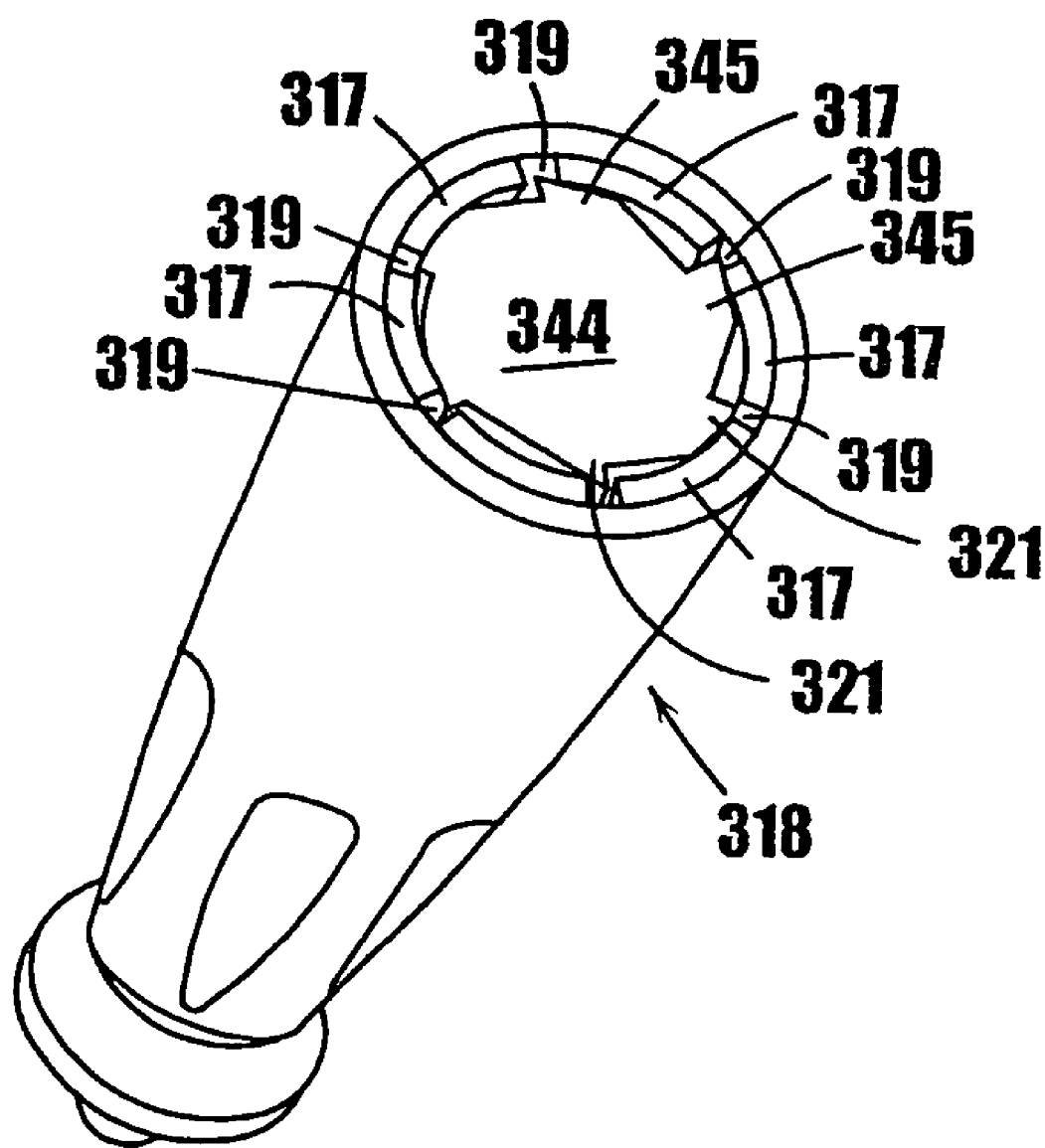
FIG. 20 is a partial cross-sectional view of the body and upper guide portion of the syringe of FIG. 18.
Figure 21:
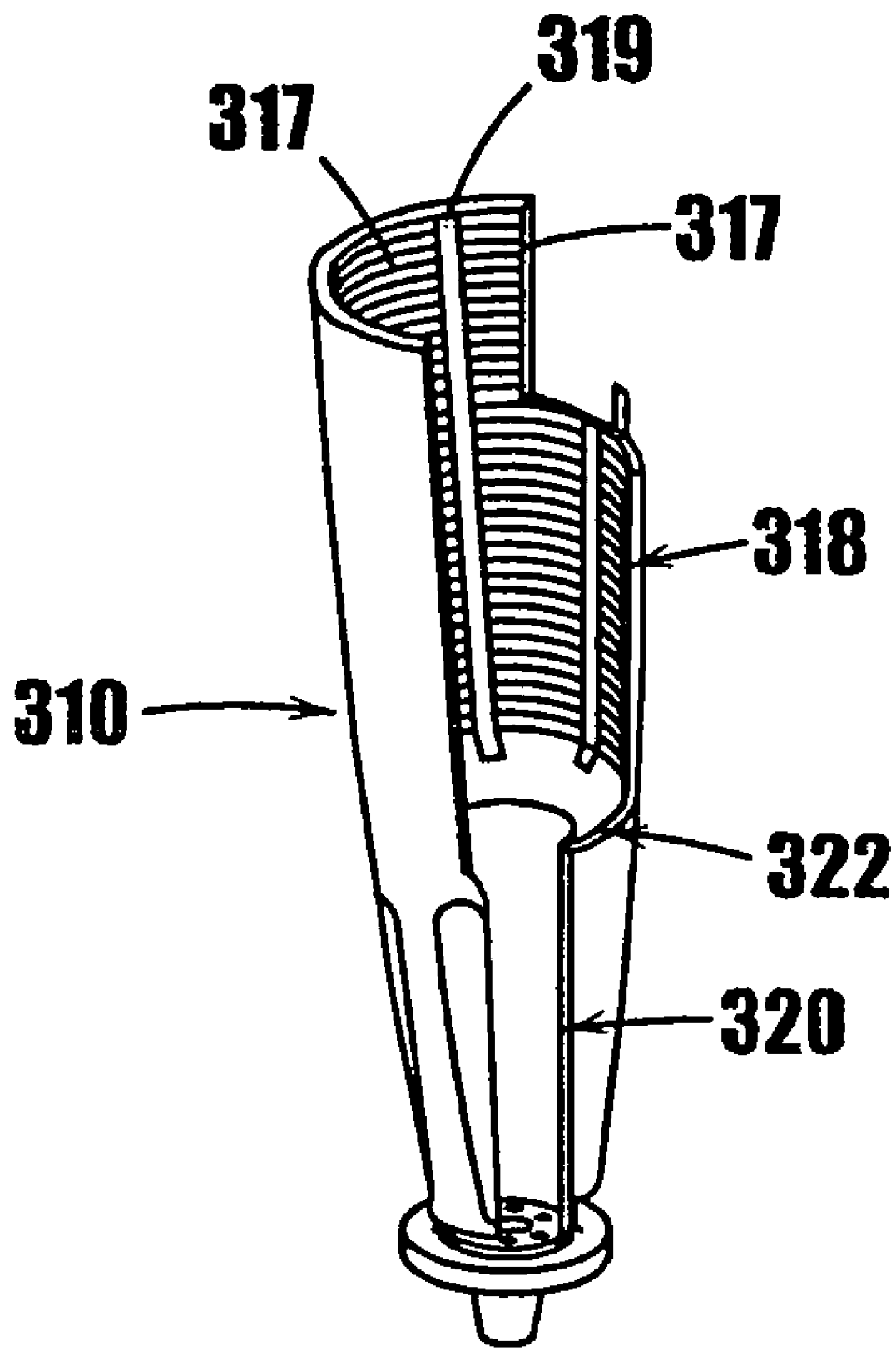
FIG. 21 is a partial, perspective view of the body of FIG. 18 with a portion broken away to show the threaded elements in the upper portion of the body.

As shown in FIGS. 20 and 21, the inner walls of the upper portion 318 and the lower portion 320 define cylindrical cavities. The upper portion 318 of the syringe comprises a plurality of axially-elongated threaded elements 317 extending from the tapered portion 322 of the syringe body 312 to the top of the syringe. Each of the threaded elements 317 is generally defined by an arc of the circle representing the thread diameter of a fully threaded inner cylinder. The sides of the threaded elements 317 define a plurality of axially-elongated slots 319 in the upper portion 318 which likewise extend from the tapered portion 322 to the top of the syringe. The depth of the slots 319 may extend completely through the syringe body 312, or may extend only partially through the syringe body.

Referring again to FIGS. 18 and 19, the inner wall 338 of the lower portion 320 of the syringe body 312 defines a smooth cylindrical cavity and has an approximately constant inner diameter over the axial length of the lower portion 320. The lower portion 320 of the syringe is used to contain the substance to be dispensed, and is dimensioned to frictionally engage the base of the plunger, as described further below. The inner diameter of the lower portion 320 is preferably constant to ensure that a specific quantity of the medicament or other substance contained therein is dispensed from the syringe for a pre-determined distance of travel by the plunger 314.

At the end of the lower portion of the syringe body, a dispensing tip indicated generally by the reference number 316 is provided to allow the substance contained in the lower portion 320 of the syringe to flow from the syringe as the plunger 314 is inserted into the lower portion. In a preferred embodiment shown in FIG. 18, the dispensing tip 316 includes a flange 328 that defines an annular U-shaped channel (not shown) similar to the U-shaped channel 30 of the syringe 10 described above. The dispensing tip 316 includes an elongated center shaft or post 332.

The syringe preferably includes a one-way valve mechanism at the dispensing tip of the syringe to prevent air or other contaminants from entering the substance contained in the syringe through the dispensing tip. The one-way valve is formed by fixing a flexible cover (not shown) on the dispensing tip 316 of the syringe body. The flexible cover is preferably made of an elastomeric material. The interior surface of the flexible cover is shaped to fit over the flange 328 on the dispensing tip 316 and to fit integrally within the annular U-channel which extends around the dispensing tip. The flexible cover forms an interference fit with the center shaft 332 on the dispensing tip. The flexible cover extends from the outer surface of the lower portion 320 of the syringe 312 to approximately the end of the center shaft 332 of the dispensing tip 316.

At the base of the center shaft 332, a plurality of cylindrical openings 356 extend through the dispensing tip. The cylindrical openings 356 communicate with the chamber in the lower portion 320 of the syringe and provide a path through which the substance in the cavity in the lower portion 320 flows as the plunger 314 is advanced into the lower portion 320 of the syringe. The interference fit between the flexible cover and the center shaft 332 forms a normally-closed valve to hermetically seal the cylindrical openings 356 until a dose of the substance contained in the syringe is delivered. The portion of the flexible cover that interfaces with the center shaft 332 may be tapered such that the thickness is greater near the base of the center shaft and gradually reduces to a lesser thickness near the end of the center shaft.

In an alternative embodiment, the one-way valve may be omitted. The center shaft 332 may be provided with a central cylindrical channel that communicates with the cavity in the lower portion 320 of the syringe to provide a path for dispensing the substance contained in the syringe. In other embodiments, other appropriate dispensing tip mechanisms that are currently or later become known to those skilled in the art can be fixedly attached to the syringe body. For example, the conventional connection device marketed under the trade name LUER-LOK can be used at the dispensing tip of the syringe to allow attachment of disposable needles. Other needle connection means, such as threaded fittings, elastomeric plugs, or fitted end caps equally may be used to attach a needle to the end of the syringe. The lower end of the syringe body may be shaped or threaded as required to accommodate the selected needle connection means. A cap or other means (not shown) to hermetically seal the dispensing end of the syringe may be used until the needle is connected to the syringe to dispense the medicament or other substance therein.

The elastomeric outer cover 315 is comprised of a flexible material that is capable of being expanded by the application of force to the inner wall of the cover and returning substantially to its original shape when the applied force is removed. The elastomeric outer cover is preferably formed by over molding an elastomeric material around the inner syringe body. The elastomeric outer cover may be any desired thickness and may include features that allow ease of use, such as, for example, the gripping indentations 307 in the outer cover shown in FIG. 18.

Referring to FIGS. 18-20, the plunger 320 comprises a base 340, a lower drive portion 342, and an upper guide portion 344. The face surface 346 of the base 340 contacts the medicament or other substance in the cavity in the lower portion 320 of the syringe during use. The base 340 is shaped and dimensioned to fit frictionally into the cavity in the lower portion 340 of the syringe body such that the medicament or other substance dose not escape between the base and the inner surface of the lower portion 320 of the syringe as the base 340 is inserted into the lower portion 320. The base 340 may be made of any suitable material known to those skilled in the art that will not react with the medicament or other substance contained in the syringe. If desired, as shown in FIG. 18, a fusible stopper, such as the fusible stopper described in detail above, can be fixedly attached to the plunger to hermetically seal the cavity in the lower portion.

The drive portion 342 of the plunger 314 is shaped and dimensioned to fit slidingly within the lower portion 320 of the syringe body. The outside diameter of the drive portion 342 is preferably at least slightly less than the inside diameter of the lower portion 320 of the syringe body to reduce the frictional force generated by movement of the plunger within the syringe body. The drive portion 342 should be sufficiently long to be fully inserted into the cavity in the lower portion 320 of the syringe body when the plunger is in its fully inserted position.

As shown in FIG. 19, the upper guide portion 344 of the plunger 314 has a plurality of threaded sections 345 with a thread pitch complementary to the pitch of the threaded elements 317 on the inner wall of the upper portion 318 of the syringe. In a preferred embodiment wherein the syringe body and plunger are made of a moldable plastic, the thread pitch is approximately 0.8 mm and the thread angle is approximately 90°. When the syringe body and the plunger are made of molded plastic, a thread angle of approximately 90° permits easier removal of the molded parts from the molds.

As shown in FIG. 20, each of the threaded sections 345 on the upper guide portion 344 of the plunger 314 have a variable thread diameter. Each of the threaded sections on the plunger has a first region wherein the thread diameter is approximately equal and complementary to the thread diameter of the threaded elements 317, a second region wherein the plunger threads have a gradually increasing thread diameter, and a the third region wherein the plunger threads have a constant diameter that is larger than the diameter of the threaded elements 317 in the upper portion 318 of the syringe. The second region and third region of the threads on the plunger together will generally extend over an area that is equal to the area occupied by the slots 319 between the threaded elements 317 in the upper portion 318 of the syringe to allow the second and third threaded regions to be received within the slots. As shown in FIG. 20, this can be accomplished by using a plurality of tine-like threaded members 321 on the upper guide portion 344 of the plunger 314. The tine-like threaded members 321 are sized to fit into the slots between the threaded elements 317 in the upper portion 318 of the syringe. A knob or other gripping portion 352 is formed at the upper end of the plunger 314 to provide means for the user to grip the plunger during use.

To deliver a metered dose of the substance from the syringe, the plunger 314 is rotated in the direction, normally clockwise, causing the plunger to travel into the syringe body. As the plunger 314 is rotated, the threaded elements 317 in the upper portion 318 of the syringe are each progressively engaged by the larger diameter threads on the second and third threaded regions on the upper guide portion 344 of the plunger 314. Because the threads on the plunger progressively increase in diameter as the plunger is rotated in the clockwise direction, the upper portion 318 of the syringe and the elastomeric outer cover 311 expand, and progressively greater force must be applied to the plunger to cause it to rotate. As the larger diameter threads on the upper guide structure 344 rotate through the threaded elements 317 of the upper portion 318 and into the slots 319 between the threaded elements, the upper portion of the syringe and elastomeric outer cover rapidly return to their original diameter.

As described above, the dose of substance delivered can be precisely controlled by establishing the thread pitch and the distance between threaded portions such that the plunger assembly travels the desired distance into the lower chamber for each turn of the plunger. A larger dose may be delivered by increasing the number of turns of the plunger for each dose delivered.

Syringe-Type Dispensers With Means for Preventing Residual Seepage of Substance Through The Dispensing Tip In FIGS. 22 through 30 another embodiment of the syringe-type dispenser is indicated generally by the reference numeral 410. The syringe 410 is the same or similar in many respects to each of the syringe-type dispensers described above with reference to FIGS. 1-21, and therefore like reference numbers preceded by the numeral "4", or preceded by the numeral "4" instead of the numerals "1" through "3", are used to indicate like elements.

Figure 22:
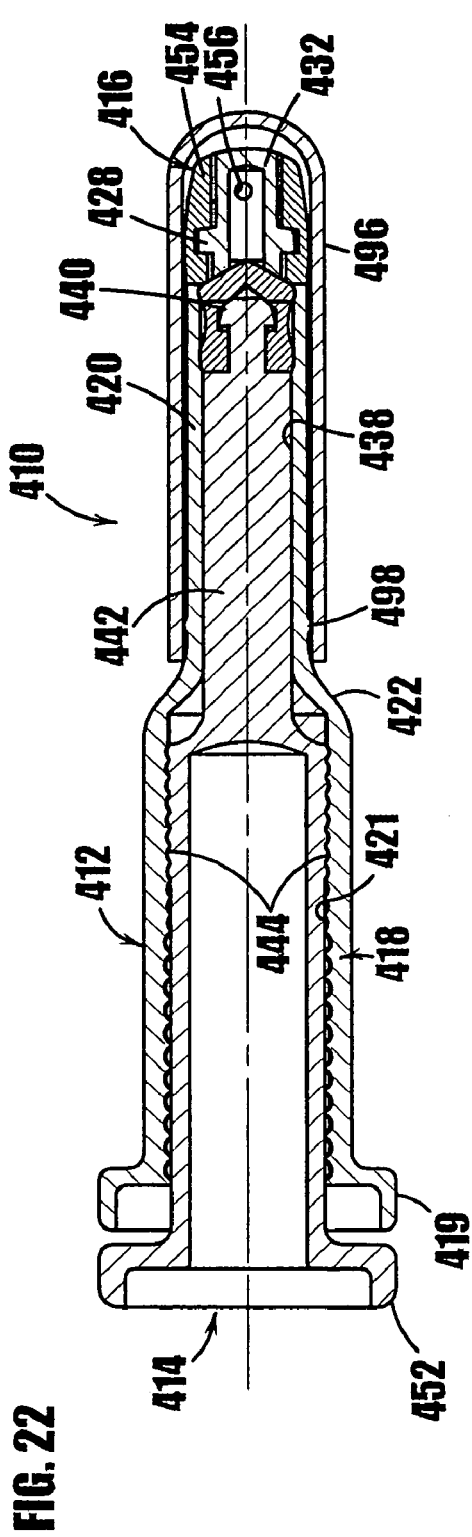
FIG. 22 is a cross-sectional view of another embodiment of a syringe-type dispenser including means for preventing residual seepage of the hermetically sealed substance through the dispensing tip and showing the plunger in the fully-extended position.
Figure 23:
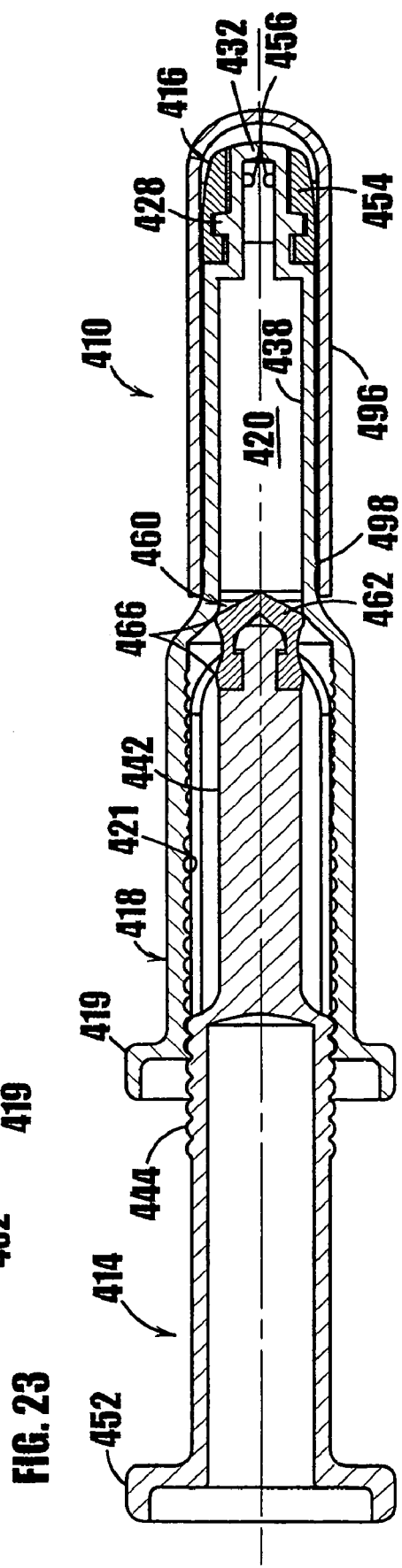
FIG. 23 is a cross-sectional view of the syringe-type dispenser of FIG. 22 showing the plunger in the retracted position.

The syringe 410 differs from the syringes described above in that the syringe 410 includes a different one-way valve on the dispensing tip 416 and includes means for preventing residual seepage of the substance contained in the sealed chamber 420 through the dispensing tip. As shown in FIGS. 22 and 23, the dispensing tip 416 of the syringe body 412 defines two flow openings 456 that are located on diametrically opposite sides of the dispensing tip relative to each other, and are oriented approximately perpendicular to the axis of the tip. The valve cover 454 forms an interference fit with the valve seat defined by the central post 432 of the dispensing tip in the same manner as the valves described above. In addition, as with the one-way valves described above, the valve cover 454 defines a gradually decreasing wall thickness in the axial direction from the interior to the exterior end of the cover to facilitate opening and closing of the valve upon movement of the plunger. All other factors being equal, the one-way valve of FIGS. 22 and 23 typically requires a higher valve opening pressure than the valves described above in connection with FIGS. 1-21. In the valves described above and shown, for example, in FIGS. 13 and 14, the flow openings 256 extend in approximately the axial direction of the dispensing tip and therefore the substance flows axially out of the dispensing tip. The laterally-extending flow openings 456 of FIGS. 22 and 23, on the other hand, require the substance to flow through an approximately 90° turn, thus requiring higher valve opening pressures (all other factors being equal) in order to move the substance through the valve.

The syringe 410 further includes means for effecting step-wise movement of the plunger within the syringe body and dispensing a predetermined amount of substance from the chamber of the syringe body. In the illustrated embodiment, the means for effecting step-wise movement includes a plurality of discrete thread portions 421 formed on an interior wall of the upper portion 418 of the syringe body, and a plurality of corresponding thread portions formed on the upper guide portion 444 of the plunger. As described in further detail below, and in a manner similar to the other embodiments of the dispenser described above, the discrete thread portions on the syringe body and plunger cooperate to provide a "click-action" type actuating mechanism that allows for incremental or step-wise movement of the plunger within the syringe body, and that preferably further provides a "click" (that may be discernable to the user by sound and/or feel) upon movement of the plunger through each incremental or step-wise movement. In addition, the discrete thread portions further provide means for preventing residual seepage of the substance contained within the chamber 420 through the one-way valve of the dispensing tip 416 upon terminating each discrete incremental or step-wise movement of the plunger.

Figure 24:
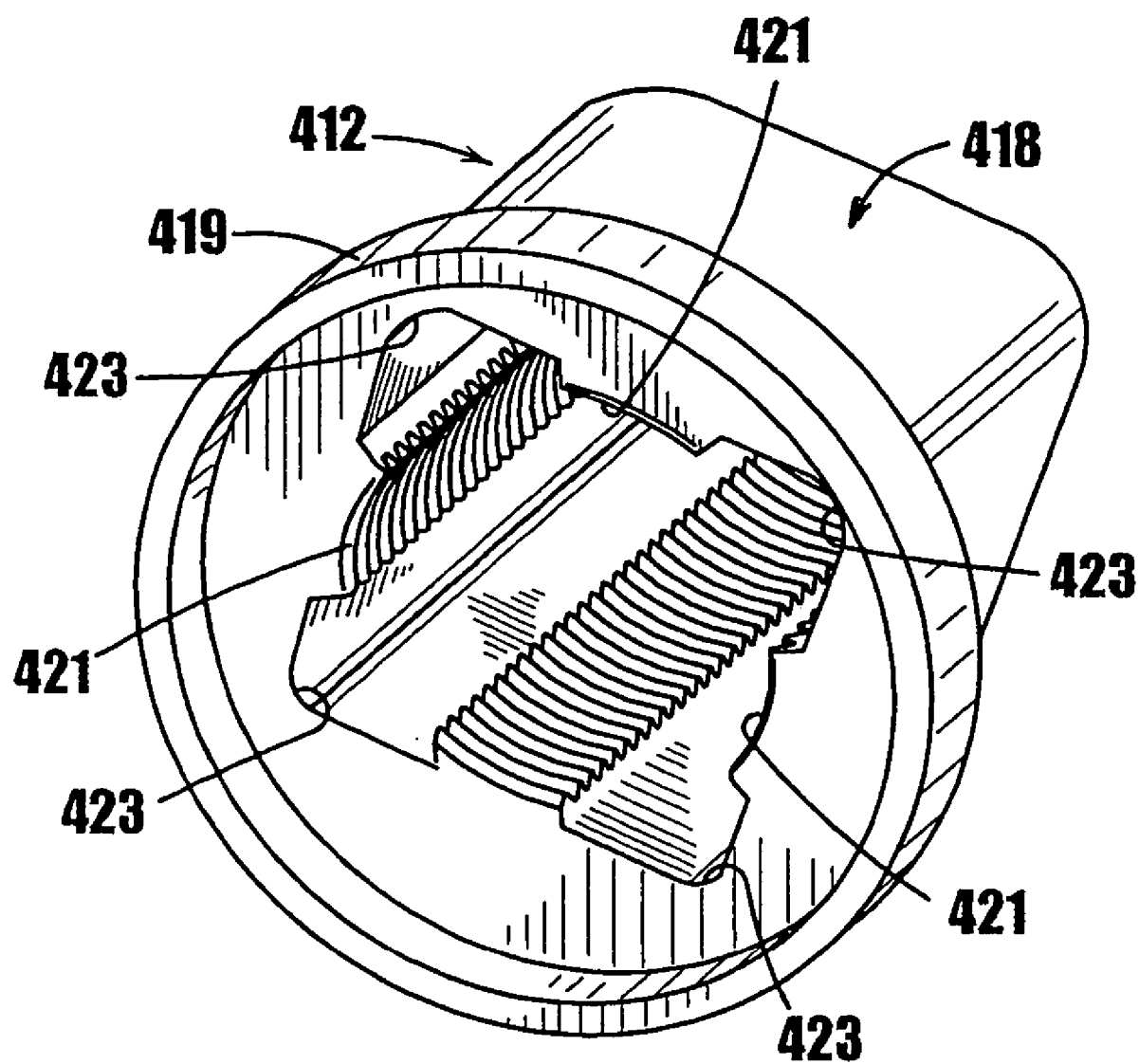
FIG. 24 is a partial, perspective view of the body of FIGS. 22 and 23 showing the discrete, axially-extending thread segments formed on the inner wall of the body.

As shown typically in FIG. 24, the upper guide portion 418 of the syringe body 412 defines four discrete thread portions 421 equally spaced approximately 90° relative to each other about the axis of the syringe body. As can be seen, each thread portion 421 extends along approximately the full axial extent of the upper guide portion 418. The thread portions 421 are substantially the same as the thread portions 221 described above in connection with FIG. 11, and therefore each thread portion 421 defines the same thread diameter and pitch as the other thread portions 421. In addition, the corners 423 of the upper guide portion 418 define laterally extending voids between adjacent thread portions 421.

Figure 25:
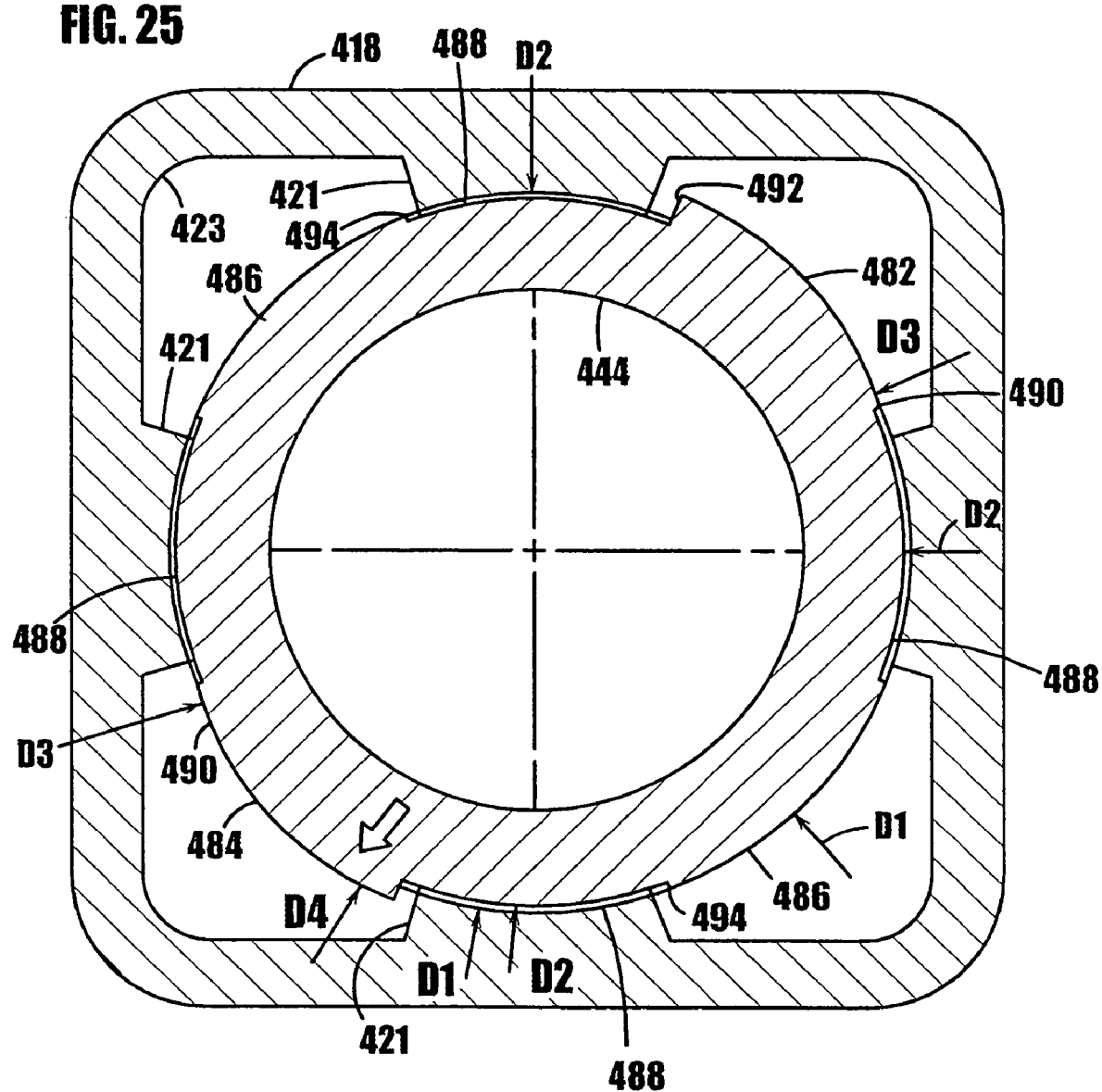
FIGS. 25 through 27 are somewhat schematic, cross-sectional views of the syringe-type dispenser of FIGS. 22 and 23 showing the progression of rotatable movement of the threaded plunger within the threaded body through ¼ turn.

As shown typically in FIG. 25, the upper guide portion 444 of the plunger 414 defines a plurality of pairs of first discrete thread segments 484, 484 located on diametrically opposite sides of the upper guide portion relative to each other; a plurality of pairs of second discrete thread segments 486, 486 located on diametrically opposite sides of the upper guide portion relative to each other and angularly spaced relative to the first discrete thread segments 484, 484; and a plurality of third discrete thread segments 488, 488, wherein each pair of diametrically opposed third thread segments 488, 488 are located between a respective pair of first diametrically opposed first thread segments 484, 484, and a respective pair of second diametrically opposed second thread segments 486, 486. As shown typically in FIG. 25, each 360° section of thread of the upper guide portion 444 of the plunger defines, when moving clockwise away from the arrow in FIG. 25, a first thread segment 484, a third thread segment 488, a second thread segment 486, a third thread segment 488, a first thread segment 484, a third thread segment 488, a second thread segment 486, and a third thread segment 488.

As shown typically in FIG. 25, each discrete thread section 421 of the upper guide portion 418 of the syringe body defines an outer diameter "D1", and each second thread section 486 defines approximately the same thread diameter "D1". Each third thread section 488 defines a second thread diameter D2 that is less than the first thread diameter D1 of the syringe body threads 421. Each first thread segment 484 defines a varying thread diameter that gradually increases from a third thread diameter D3 at the leading edge 490 of the respective first thread segment 484, to a fourth thread diameter D4 at the trailing edge 492 of the respective first thread segment 484. The third thread diameter D3 at the leading edge of each first thread segment 484 is slightly greater than the first thread diameter D1 of the syringe body threads 421, and the fourth thread diameter D4 is greater than both the first and third thread diameters D1 and D3, respectively. In the illustrated embodiment, the first thread diameter D1 is approximately 10 mm, the second thread diameter D2 is approximately 9.8 mm, the third thread diameter D3 is approximately 10.3 mm, and the fourth diameter D4 is approximately 10.6 mm. As may be recognized by those of ordinary skill in the pertinent art based on the teachings herein, these dimensions are only exemplary, and may be changed as desired depending upon the other dimensions of the dispenser or otherwise as required or might be desired for any particular application of the dispenser.

As also shown typically in FIG. 25, the leading edge 490 of each first thread segment 484 defines an approximately 45° chamfer extending between the respective first and third thread segments 484 and 488, respectively, to facilitate slidable engagement of the first thread segments 484 of the plunger with the corresponding thread segments 421 of the syringe body. Similarly, the leading edge 494 of each second thread segment 486 of the plunger defines an approximately 45° chamfer extending between the respective second and third thread segments 486 and 488, respectively, to facilitate slidable engagement of the second thread segments 484 of the plunger with the corresponding thread segments 421 of the syringe body. As may be recognized by those of ordinary skill in the pertinent art based on the teachings herein, the degree and/or shape of the leading edge of the thread segments described herein are only exemplary, and may be changed as desired depending upon the requirements of a particular dispenser or otherwise to facilitate the operation of the dispenser.

Figure 26:
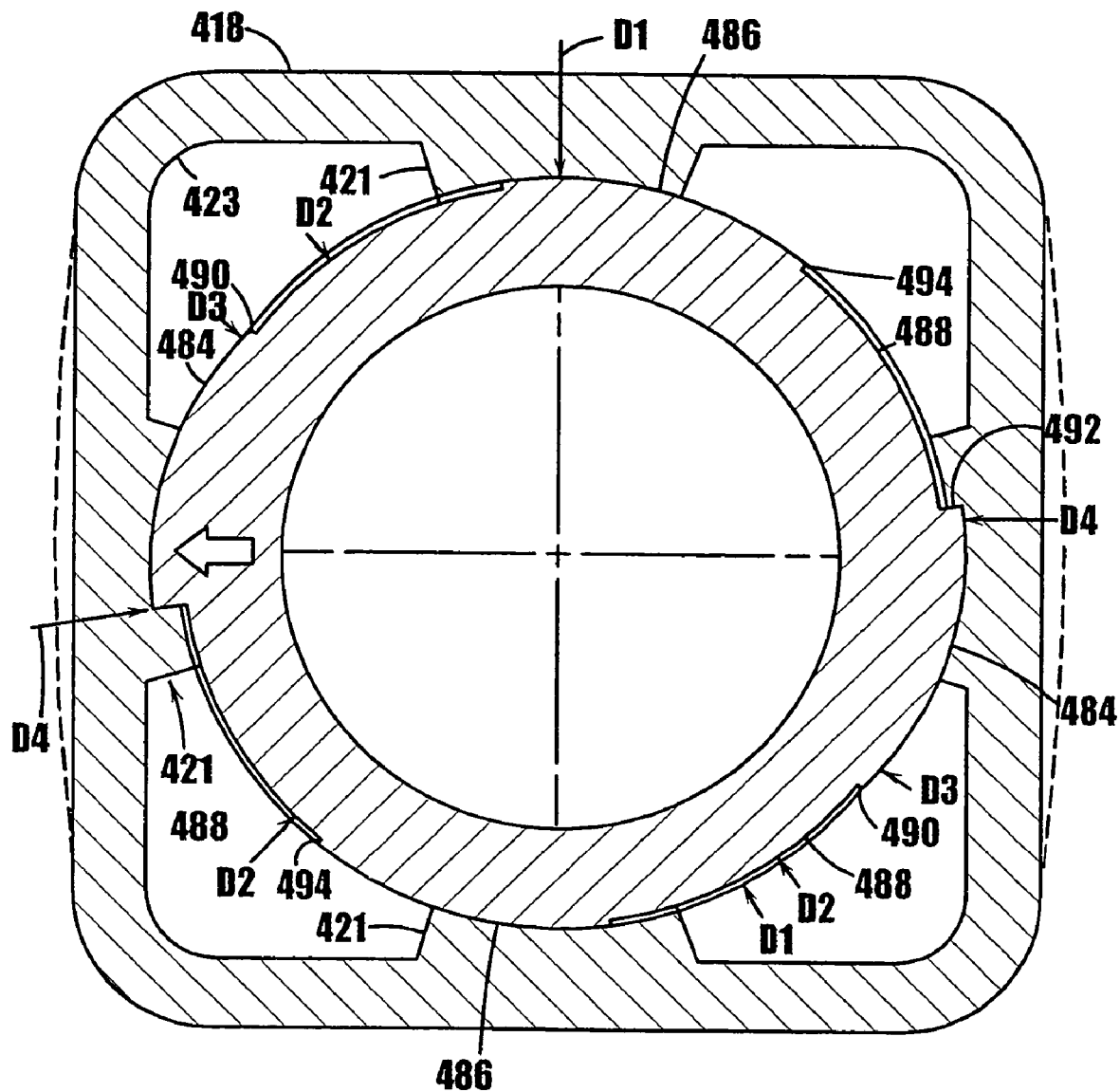
Figure 27:
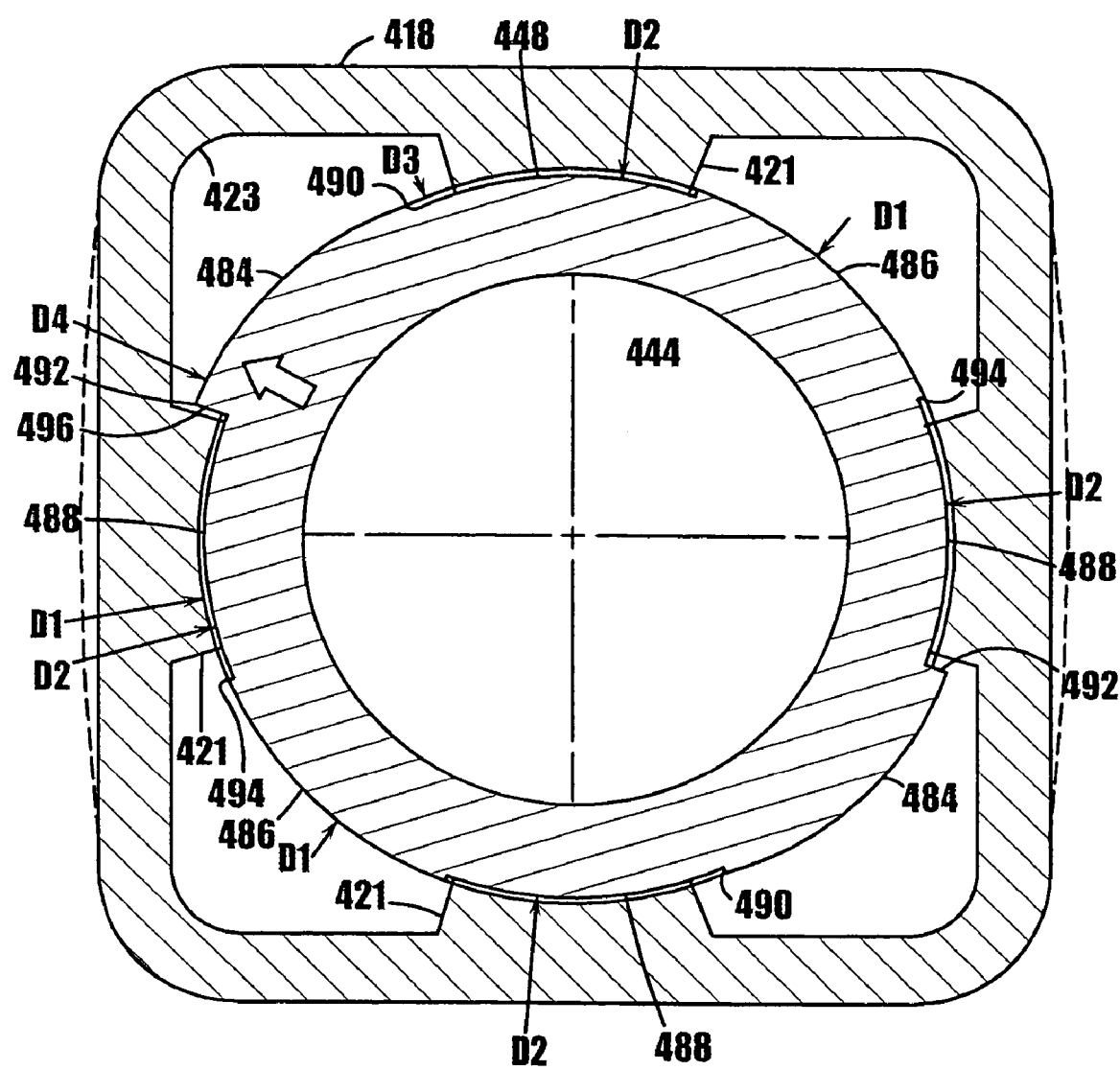

With reference to FIGS. 25 through 27, in order to dispense the hermetically sealed substance from the chamber 420 through the dispensing tip 416, the plunger is rotating in a clockwise manner. As shown in the progressive views of FIGS. 25 through 27, rotation of the plunger ¼ turn (or about 90°) in the clockwise direction causes the first thread segments 484 to slidingly engage the respective syringe body threads 421 and, in turn, laterally expand the respective side walls of the syringe body outward, as indicated in the exemplary broken lines in FIG. 26. More specifically, as the leading edge 490 of each first thread segment threadedly engages the corresponding thread segment 421 of the syringe body, the respective portion of the side wall of the syringe body is flexed outwardly to locally match the leading edge diameter D3 of the first thread segments 484 of the plunger. As the plunger is further rotated in the clockwise direction, the side wall of the syringe body is flexed further outwardly by the gradually increasing diameters of the first thread segments 484 (i.e., as the first thread segment surface engaging the syringe body increases in diameter from D3 to D4). Then, as shown typically in FIG. 27, upon rotating a full ¼ turn in the clockwise direction, the trailing edge 492 of each first thread segment 484 of the plunger passes through the respective thread segment 421 of the syringe body, and only the small diameter (D2) thread segments 488 of the plunger are located in contact with the syringe body thread segments 421. Upon passage of the first thread segments 484 of the plunger through the syringe body thread segments 421, the opposing lateral walls of the syringe body snap back or laterally inwardly, thus creating a click-action sensation for the user and thereby signaling to the user that the plunger has completed ¼ turn and dispensed the predetermined dosage of substance through the dispensing tip. As shown typically in FIG. 27, the difference in diameter between the trailing edge of each first thread segment 484 and the leading edge of the adjacent third thread segment 488 creates a stop surface 496 preventing reverse (or counterclockwise) movement of the plunger. As can be seen, counterclockwise movement of the plunger causes the stop surfaces 496 of the plunger to engage the adjacent side walls of the thread segments 421 of the syringe body to thereby prevent further reverse (or counterclockwise) movement of the plunger.

Figure 28:
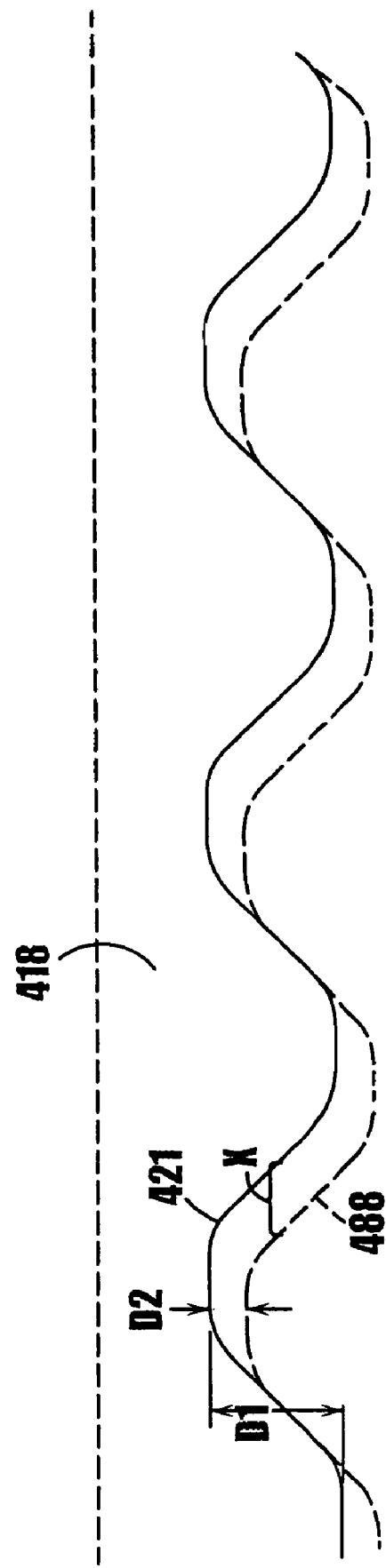
FIG. 28 is a partial, somewhat schematic view of the syringe body threads and plunger threads, and illustrating the axial play of the plunger when located in the rest position in order to prevent residual seepage of the sealed substance through the dispensing tip.
Figure 29:
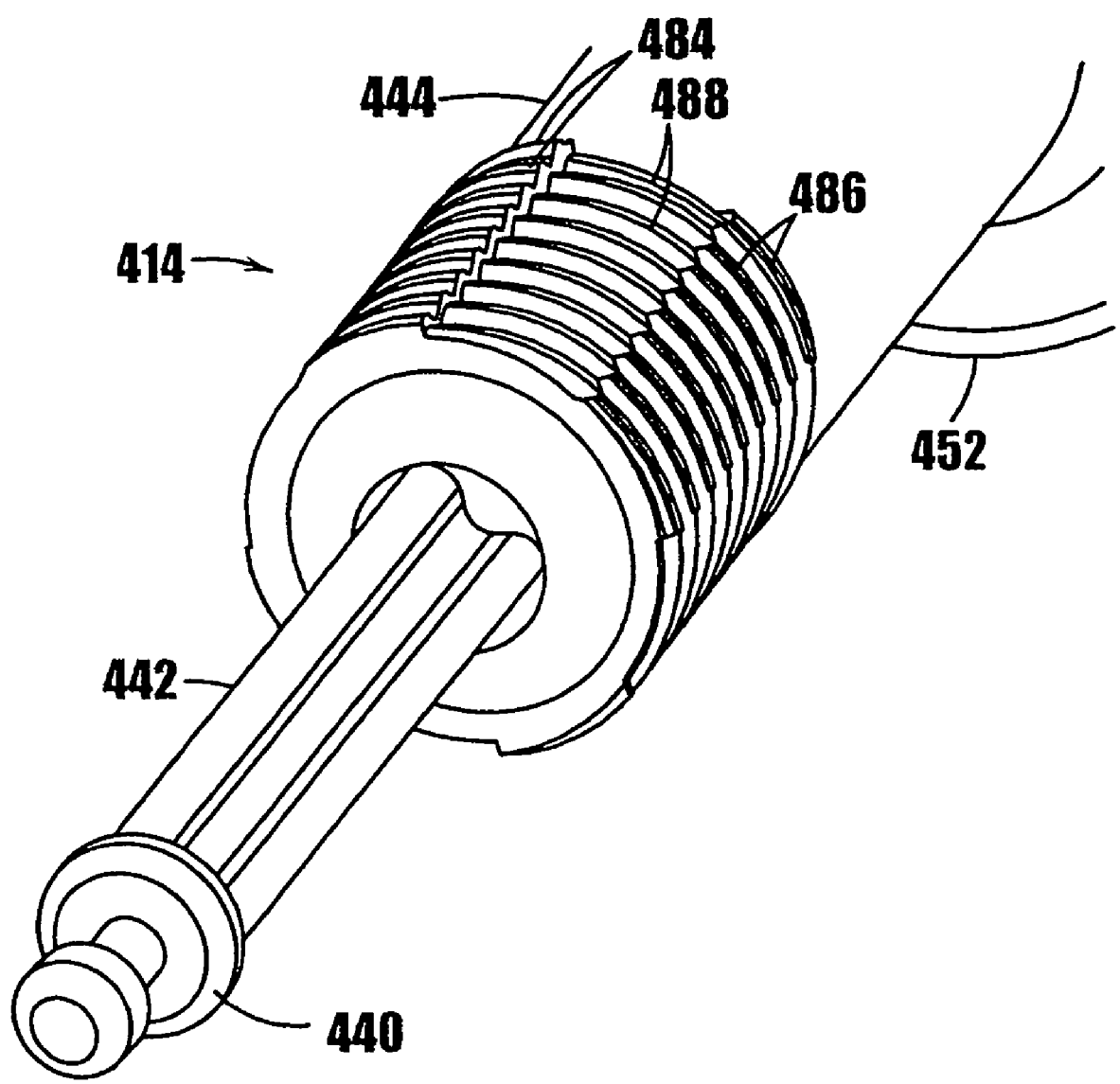
FIG. 29 is a partial, perspective view of the plunger of FIGS. 22 and 23, with parts removed for clarity, and illustrating the different thread segments of the plunger.
Figure 30:
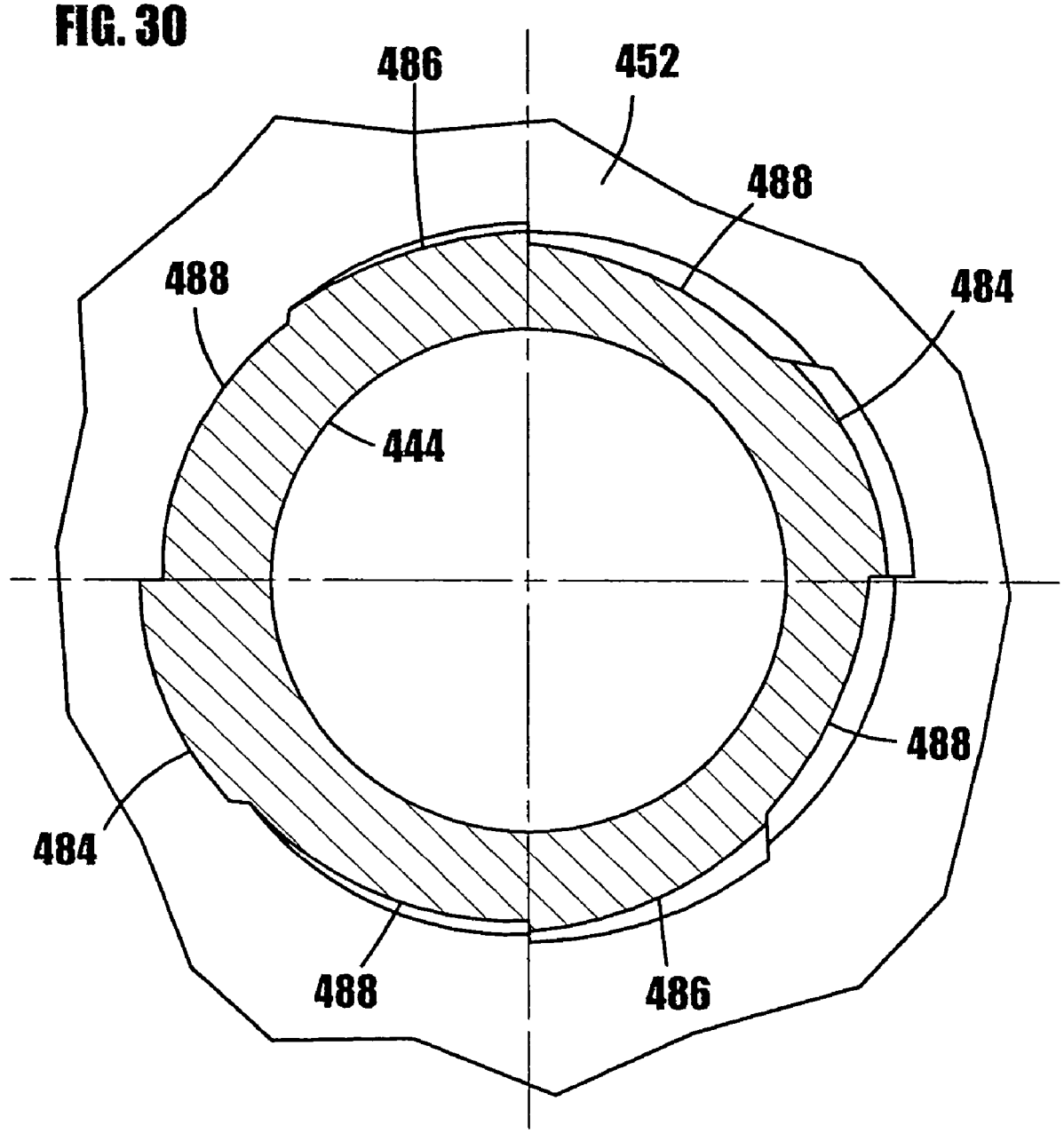
FIG. 30 is a cross-sectional view of the plunger of FIG. 29 further illustrating the different thread segments of the plunger.

With reference to FIGS. 27 and 28, when located in the rest position (i.e., with the third thread segments 488 of the plunger engaging the syringe body threads 421, and the first and second thread segments 484 and 486, respectively, of the plunger located within the voids 423 of the syringe body), the plunger is allowed limited axial movement in order to relieve any residual pressure within the hermetically sealed chamber 420 of the syringe body (FIG. 23), and thereby substantially prevent any such pressure from causing any residual seepage of the substance through the dispensing tip. As shown typically in FIG. 28, because the diameter (D2) of the third thread segments 488 of the plunger is less than the diameter (D1) of the syringe body threads 421, the plunger is permitted to move axially a distance "X". Accordingly, if after dispensing the pre-metered dose of substance through the dispensing tip there is residual pressure within the hermetically sealed chamber 420, or if any such pressure develops due, for example, to differential thermal expansion or otherwise because of changing environmental conditions, the plunger is permitted to move axially inwardly (i.e., away from the dispensing tip) by the distance "X" in order to relieve such pressure. As a result, any such residual pressure is substantially prevented from forcing any of the substance through the dispensing tip and thus creating a messy or otherwise undesirable residue on the surface of the dispensing tip.

In the illustrated embodiment, the distance "X" is approximately 0.2 mm. In addition, the threads on the plunger and on the syringe body are approximately 90° threads. However, as may be recognized by those of ordinary skill in the pertinent art based on the teachings herein, these dimensions and thread angles are only exemplary, and may be changed as desired depending upon the application and/or other requirements of the syringe or other dispenser of the present invention.

As shown typically in FIGS. 22 and 23, the syringe 410 preferably includes a cover 496 for protecting the dispensing tip 416 when not in use. In the illustrated embodiment, the cover extends axially over the lower portion of the syringe body. As shown typically in FIGS. 22 and 23, the lower portion of the syringe body 412 may include an annular rib 498 or other structural feature to facilitate releasably securing the cover to the syringe body.

Syringe-Type Dispensers With Concealed, Movable Plungers

Figure 31:
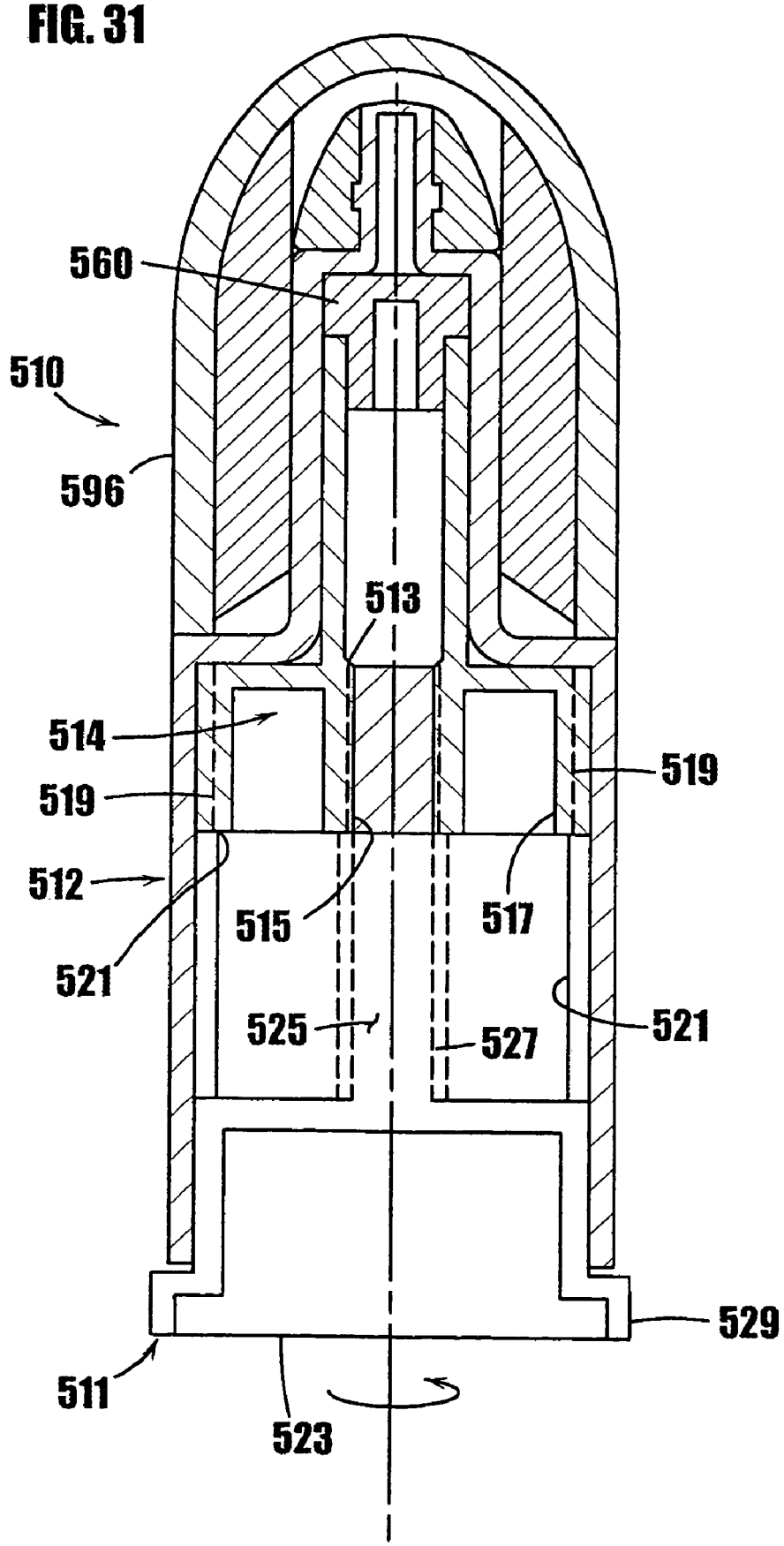
FIG. 31 is a cross-sectional view of another embodiment of a syringe-type dispenser including a concealed plunger and a drive mechanism for rotatably moving the plunger through the syringe body, and illustrating the plunger in the fully-extended position.
Figure 32:
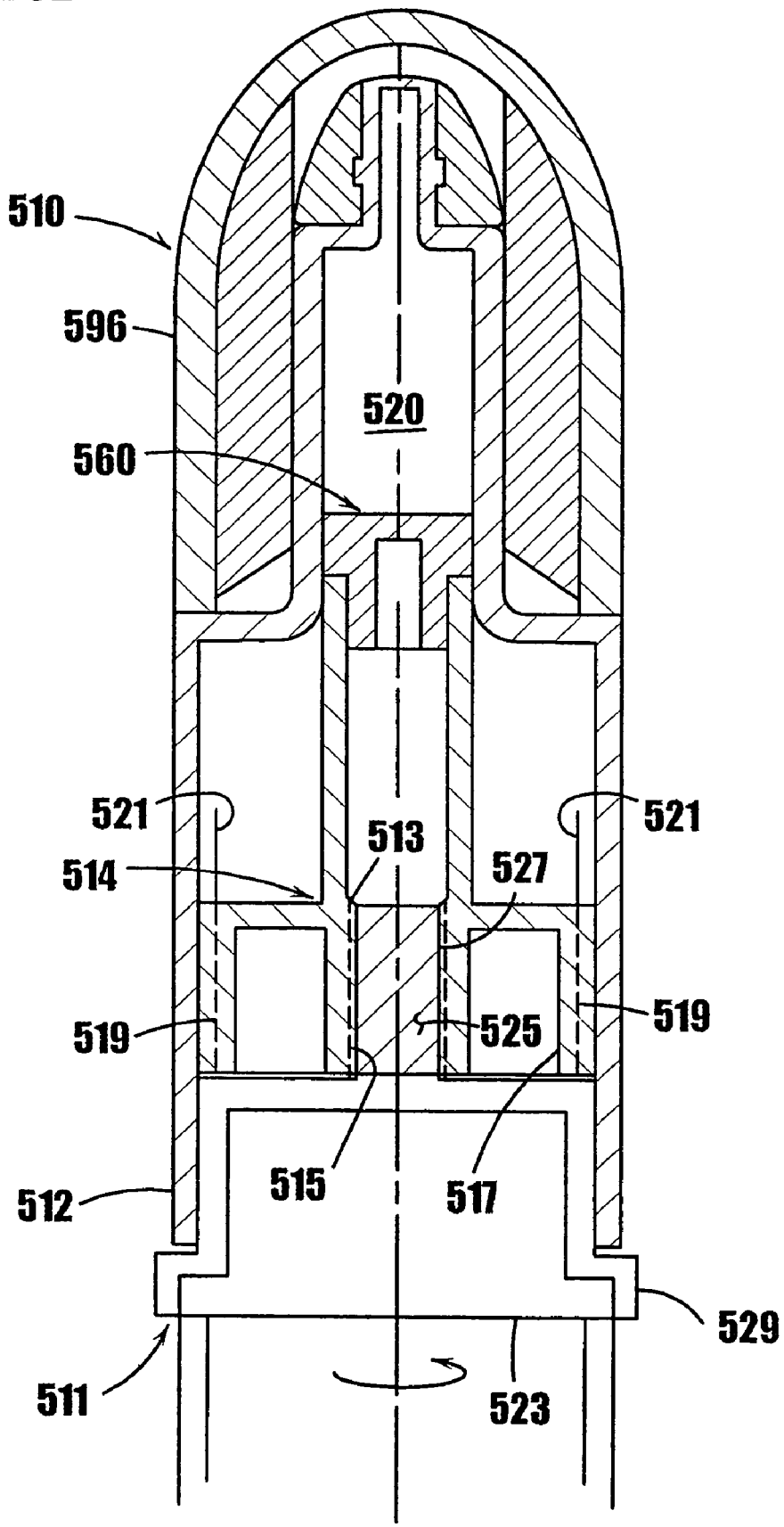
FIG. 32 is a cross-sectional view of the syringe-type dispenser of FIG. 31 illustrating the plunger in a retracted position.

In FIGS. 31 and 32, another syringe-type dispenser is indicated generally by the reference numeral 510. The syringe-type dispenser 510 is the same as or similar in many respects to each of the syringe-type dispensers described above with reference to FIGS. 1-30, and therefore like reference numbers preceded by the numeral "5", or preceded by the numeral "5" instead of the numerals "1" through "4", are used to indicate like elements.

The syringe-type dispenser 510 differs from the syringe-type dispensers described above in connection with FIGS. 1-30 in that the plunger 514 is fully concealed within the syringe body 512, and the syringe further includes a mechanism 511 for driving the plunger within the syringe body. The base or inner end of the plunger 514 defines an axial bore 513 including a first or inner set of threads 515 formed therein, and an annular flange 517 defining two diametrically opposed, axially-extending slots 519 formed thereon. The syringe body 512 defines a pair of diametrically opposed, axially-extending ribs 521 formed on an inner wall thereof and slidably received within the slots 519 formed on the peripheral flange 517 of the plunger. A drive wheel 523 is rotatably mounted in the open end of the syringe body 512, and includes an axially-extending drive shaft 525 defining a second set of threads 527 formed on the outer surface thereof. As shown in FIGS. 31 and 32, the second set of threads 527 on the drive shaft 525 threadedly engage the first set of threads 515 formed at the base of the plunger to axially move the plunger upon rotating the drive wheel 523. The drive wheel 523 further includes an annular, exposed gripping surface 529 formed at the base of the syringe body for gripping and rotation by the user. Upon rotating the gripping surface 529, the drive shaft 527 rotatably drives the plunger 514 and, in turn, moves the plunger tip 560 through the sealed chamber 520 to dispense the substance from the chamber through the dispensing tip.

As may be recognized by those skilled in the pertinent art based on the teachings herein, the syringe body 512 may take the same shape as the syringe body 412 described above, and threads may be formed on the syringe body and plunger in the same manner as described above to create a click-action type actuating mechanism for effecting step-wise or incremental movement of the plunger, and/or to prevent any pressure within the hermetically sealed chamber from causing residual seepage of any substance through the dispensing tip.

Figure 33:
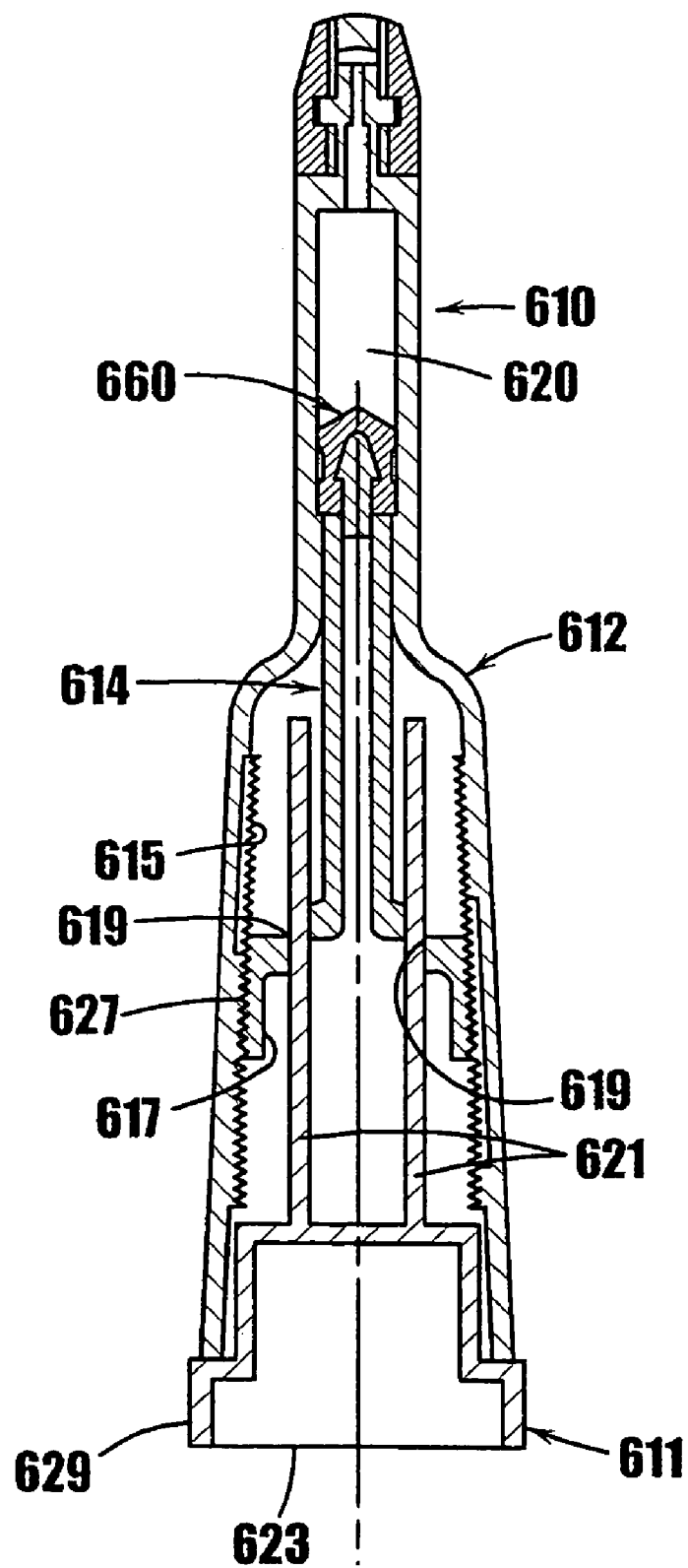
FIG. 33 is a cross-sectional view of another embodiment of a syringe-type dispenser including a concealed plunger and a drive mechanism for rotatably moving the plunger through the syringe body, and illustrating the plunger in a retracted position.
Figure 34:
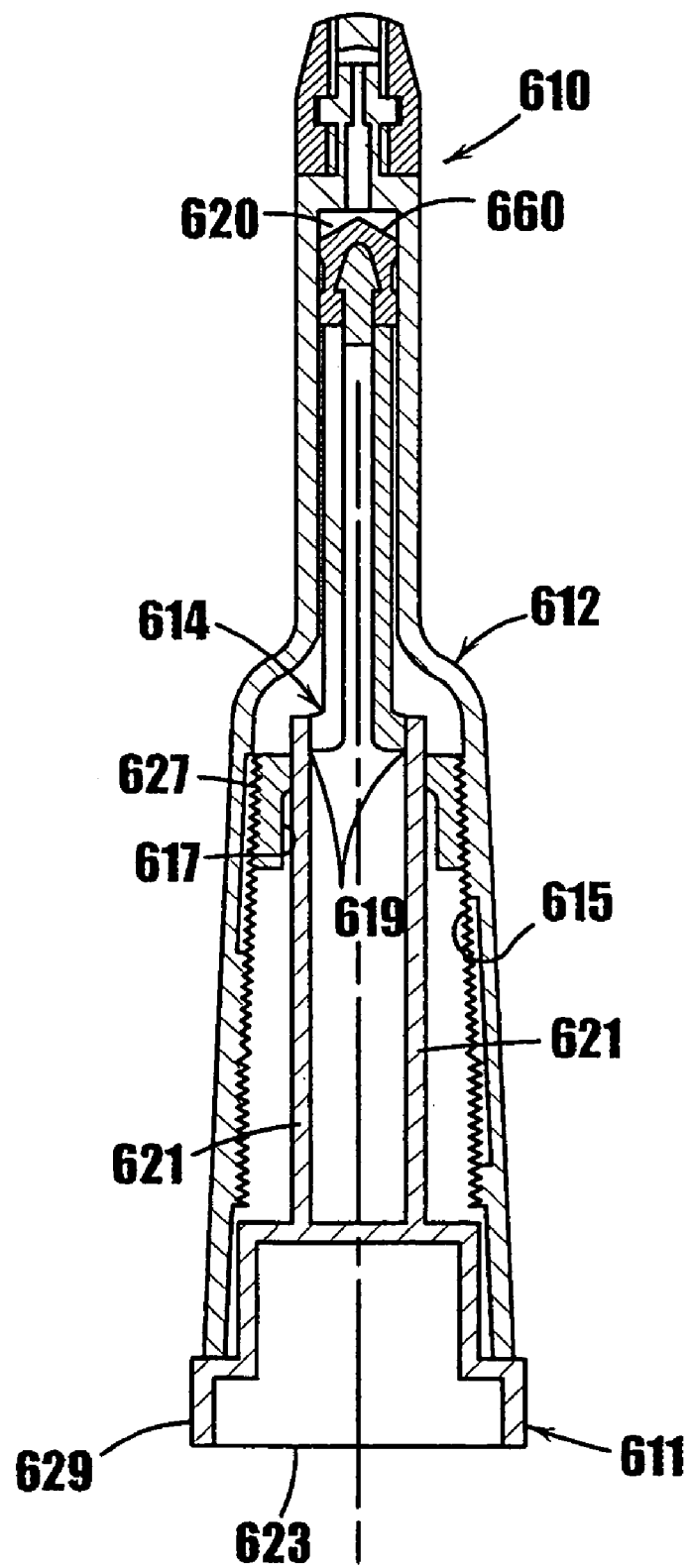
FIG. 34 is a cross-sectional view of the syringe-type dispenser of FIG. 33 illustrating the plunger in an extended position.

In FIGS. 33 and 34, another syringe-type dispenser is indicated generally by the reference numeral 610. The syringe-type dispenser 610 is the same as or similar in many respects to each of the syringe-type dispensers described above with reference to FIGS. 1-32, and therefore like reference numbers preceded by the numeral "6", or preceded by the numeral "6" instead of the numerals "1" through "5", are used to indicate like elements.

The syringe-type dispenser 610 differs from the syringe-type dispensers described above in connection with FIGS. 1-30 in that the plunger 614 is fully concealed within the syringe body 612, and the syringe further includes a mechanism 611 for driving the plunger within the syringe body. The base or inner end of the plunger 614 defines an annular flange 617 including a first set of threads 627 formed thereon, and a pair of diametrically opposed slots 619 formed through the base adjacent to the plunger shaft. The syringe body 612 defines a second set of threads 615 axially extending along the inner wall of the syringe body for threadedly engaging the corresponding threads 627 of the plunger. A drive wheel 623 is rotatably mounted in the open end of the syringe body 612, and includes a pair of diametrically opposed, axially-extending drive posts 621. As shown in FIGS. 33 and 34, the second set of threads 627 on the plunger threadedly engage the first set of threads 615 formed on the syringe body to axially move the plunger upon rotating the drive wheel 623. In addition, the posts 621 are slidably received through the slots 619 of the plunger to cause rotation and, in turn, axial movement of the plunger upon rotating the drive wheel. The drive wheel 623 further includes an annular, exposed gripping surface 629 formed at the base of the syringe body for gripping and rotation by the user. Upon rotating the gripping surface 629, the axially-extending posts 621 rotatably drive the plunger 614 and, in turn, move the plunger tip 660 through the sealed chamber 620 to dispense the substance from the chamber through the dispensing tip.

Figure 38:
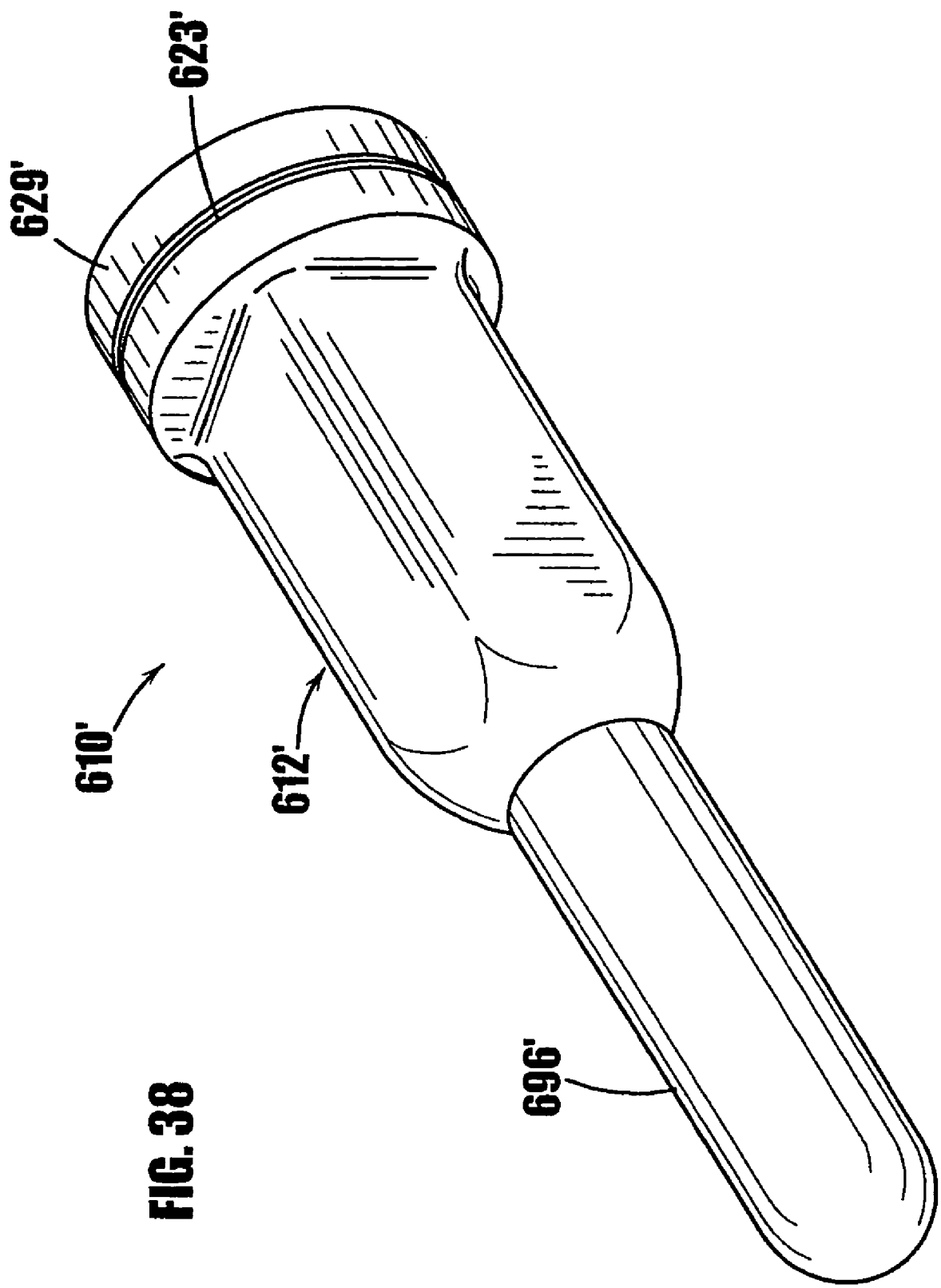
FIG. 38 is a perspective view of another syringe-type dispenser including a concealed plunger and a drive mechanism for rotatably moving the plunger in a step-wise manner through the syringe body.
Figure 39:
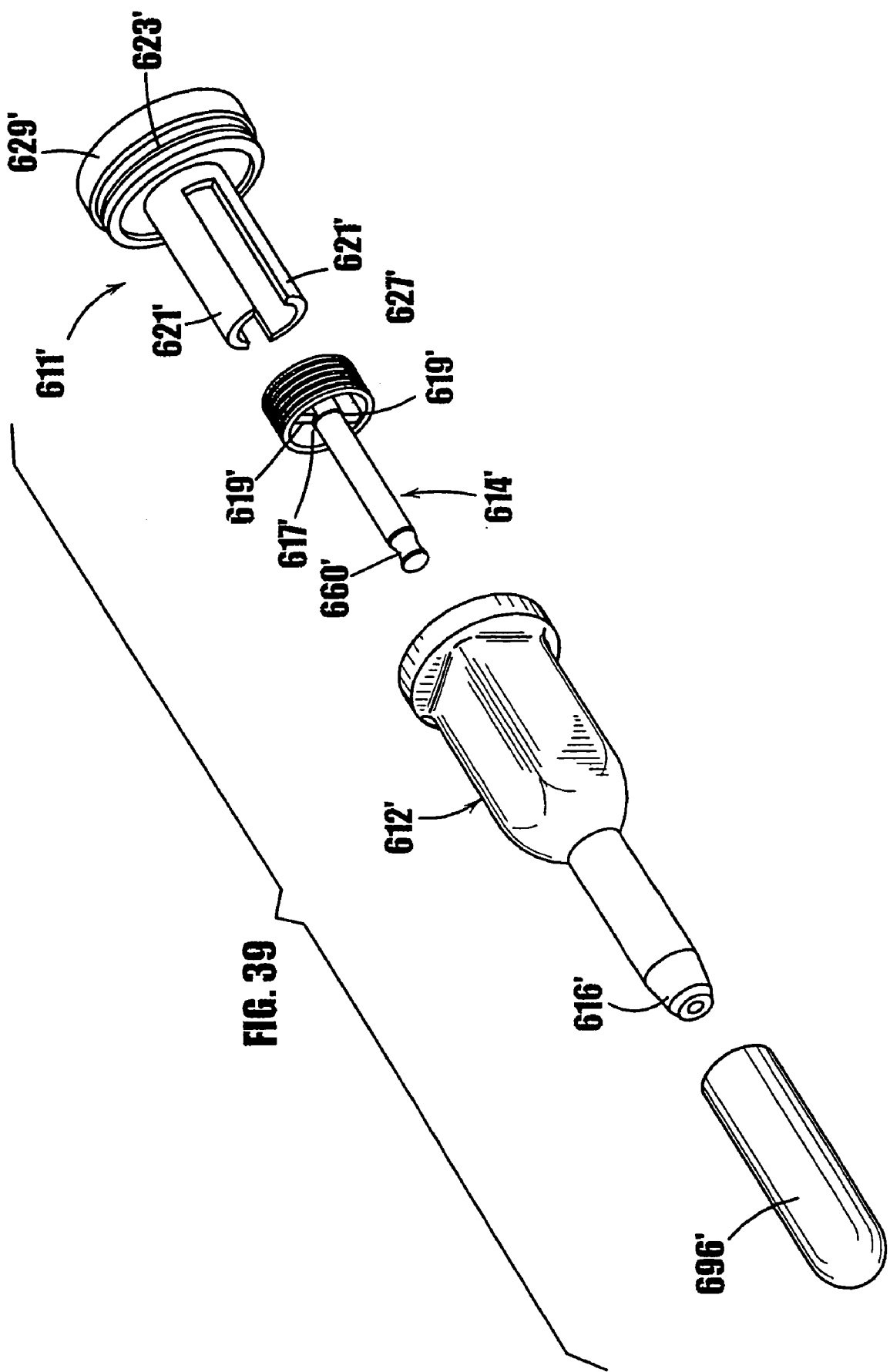
FIG. 39 is a perspective, exploded view of the syringe-type dispenser of FIG. 38.
Figure 40:
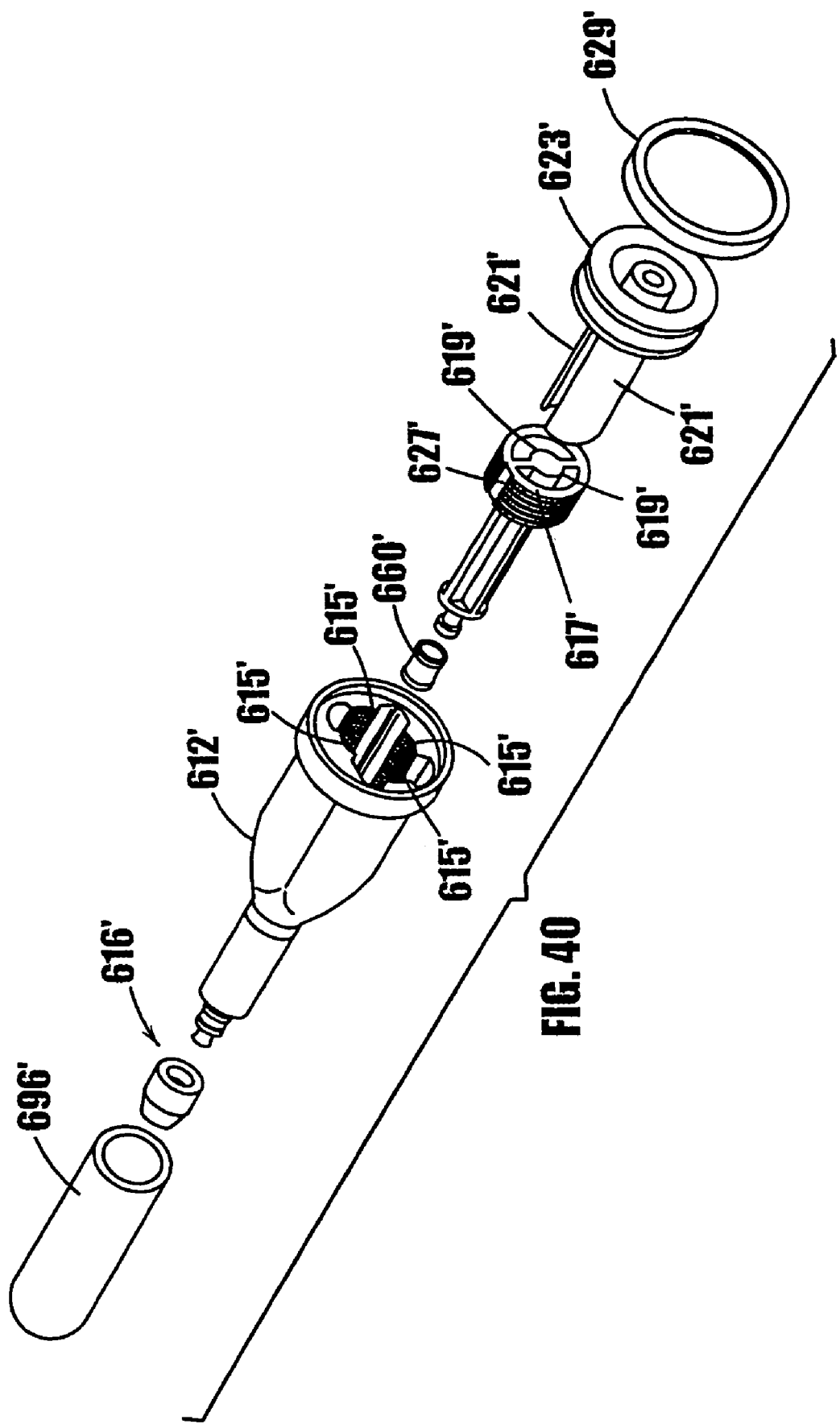
FIG. 40 is another perspective, exploded view of the syringe-type dispenser of FIG. 38.

Turning to FIGS. 38-40, In FIGS. 33 and 34, another syringe-type dispenser is indicated generally by the reference numeral 610'. The dispenser 610' is the same in many respects as the dispenser 610 described above in connection with FIGS. 33 and 34, and therefore like reference numerals including the prime symbol ("'") are used to indicate like elements. The primary difference of the dispenser 610' in comparison to the dispenser 610 is that the dispenser 610' includes a syringe body 612' that defines the same shape as the syringe body 412 described above, and the threads 615' on the syringe body and the threads 627' on the plunger 614' are formed in the same manner as described above to create a click-action type actuating mechanism for effecting step-wise or incremental movement of the plunger and to prevent any pressure within the hermetically sealed chamber from causing residual seepage of any substance through the dispensing tip.

Figure 35:
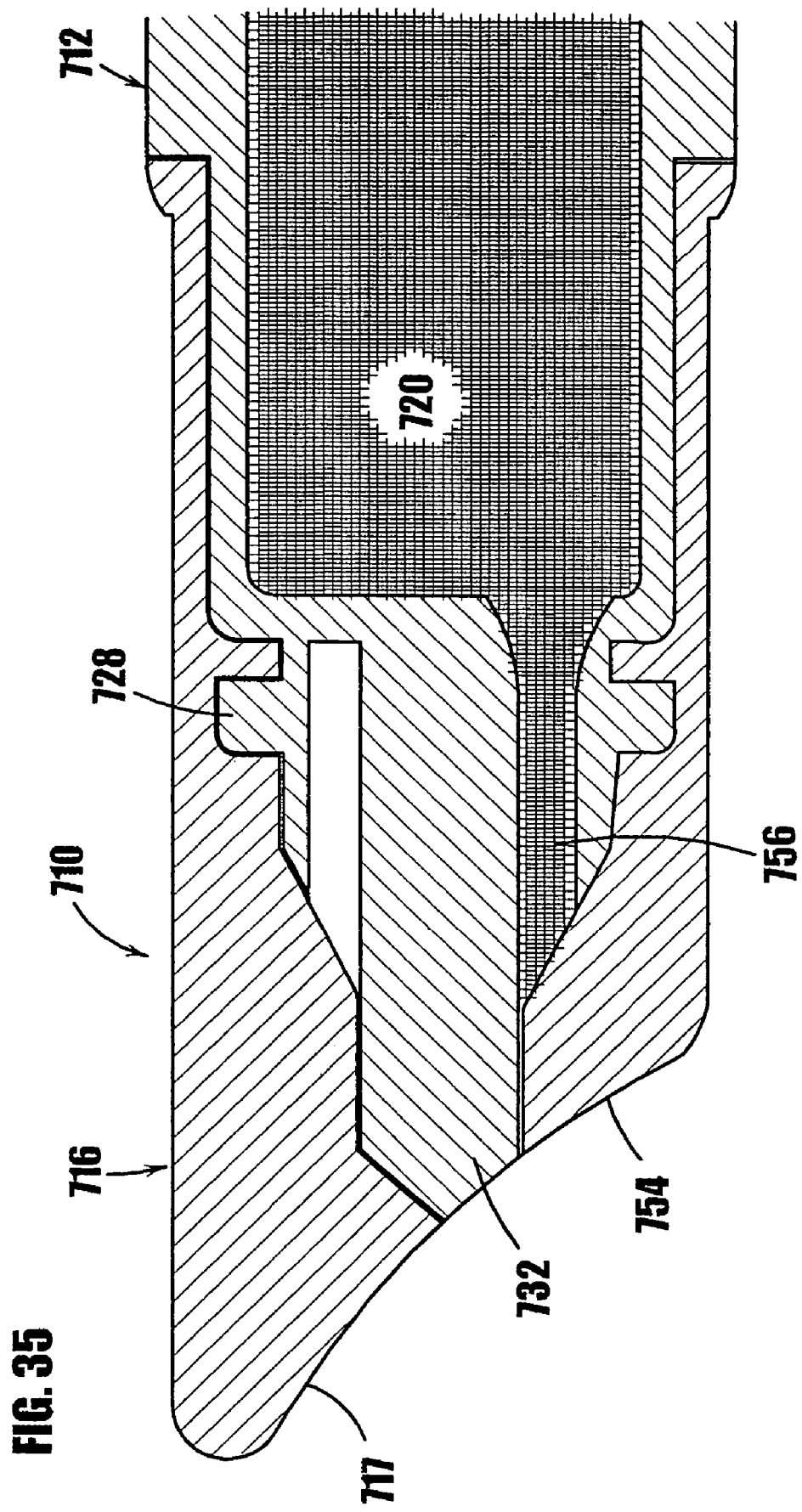
FIG. 35 is a partial, cross-sectional view of another embodiment of a syringe-type dispenser of the present invention including a dispensing tip shaped to conformably contact a user's lips or other surface contour for cosmetic applications.
Figure 36:
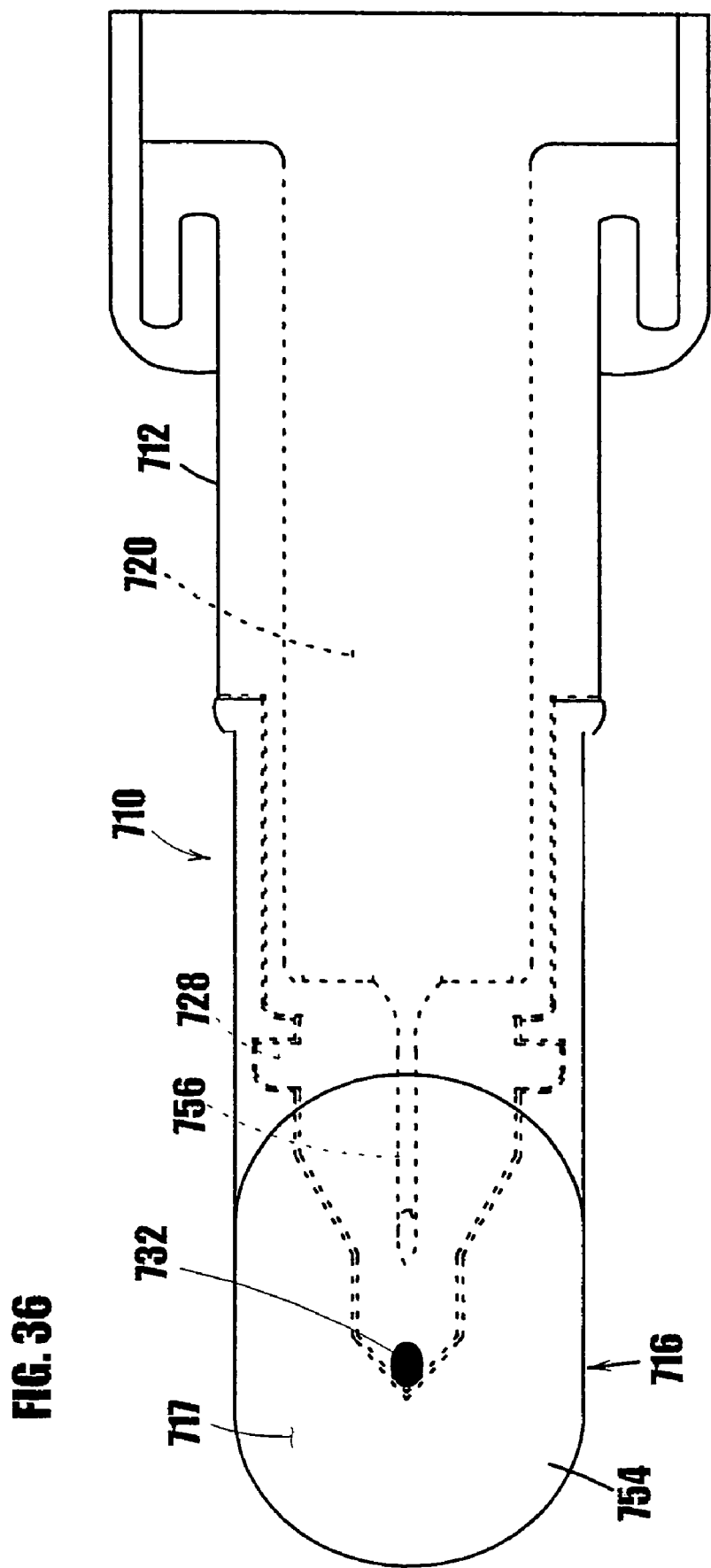
FIG. 36 is a side elevational view of the syringe-type dispenser of FIG. 35.

Syringe-Type Dispensers With Uniquely-Shaped Dispensing Tips For Cosmetic Applications In FIGS. 35 and 36, another syringe-type dispenser embodying the present invention is indicated generally by the reference numeral 710. The syringe-type dispenser 710 is the same as or similar in many respects to each of the syringe-type dispensers described above with reference to FIGS. 1-34, and therefore like reference numbers preceded by the numeral "7", or preceded by the numeral "7" instead of the numerals "1" through "6", are used to indicate like elements.

As can be seen, the dispensing tip 716 of the syringe-type dispenser 710 defines an approximately concave dispensing surface 717 shaped to conformably contact a user's lips or other surface contour. In the illustrated embodiment, the dispensing tip 716 defines a single opening 756 for the flow of the substance contained within the sealed chamber 720 therethrough. However, as may be recognized by those skilled in the pertinent art based on the teachings herein, the dispensing tip may include any desired number of such openings in any desired configuration depending upon the requirements or needs of a particular application. The valve cover 754 may be made of any of the types of flexible, polymeric materials described above in connection with the previous embodiments. For example, the valve cover 754 may be molded of the relatively elastic polymeric material sold under the trademark KRATON 20A, and the valve seat 732 may be molded of the relatively harder polymeric material sold under the trademark KRATON 65A. These materials are only exemplary, however, and may be any of numerous different materials that are currently or later become known for performing the functions of the valve cover and valve seat as described herein.

Although not shown, the syringe-type dispenser 710 preferably includes a plunger and syringe body as described above in connection with any of the previous embodiments, and preferably further includes a click-action type actuating mechanism for effecting step-wise or incremental movement of the plunger, and/or to prevent any pressure within the hermetically sealed chamber from causing residual seepage of any substance through the dispensing tip.

Figure 37:
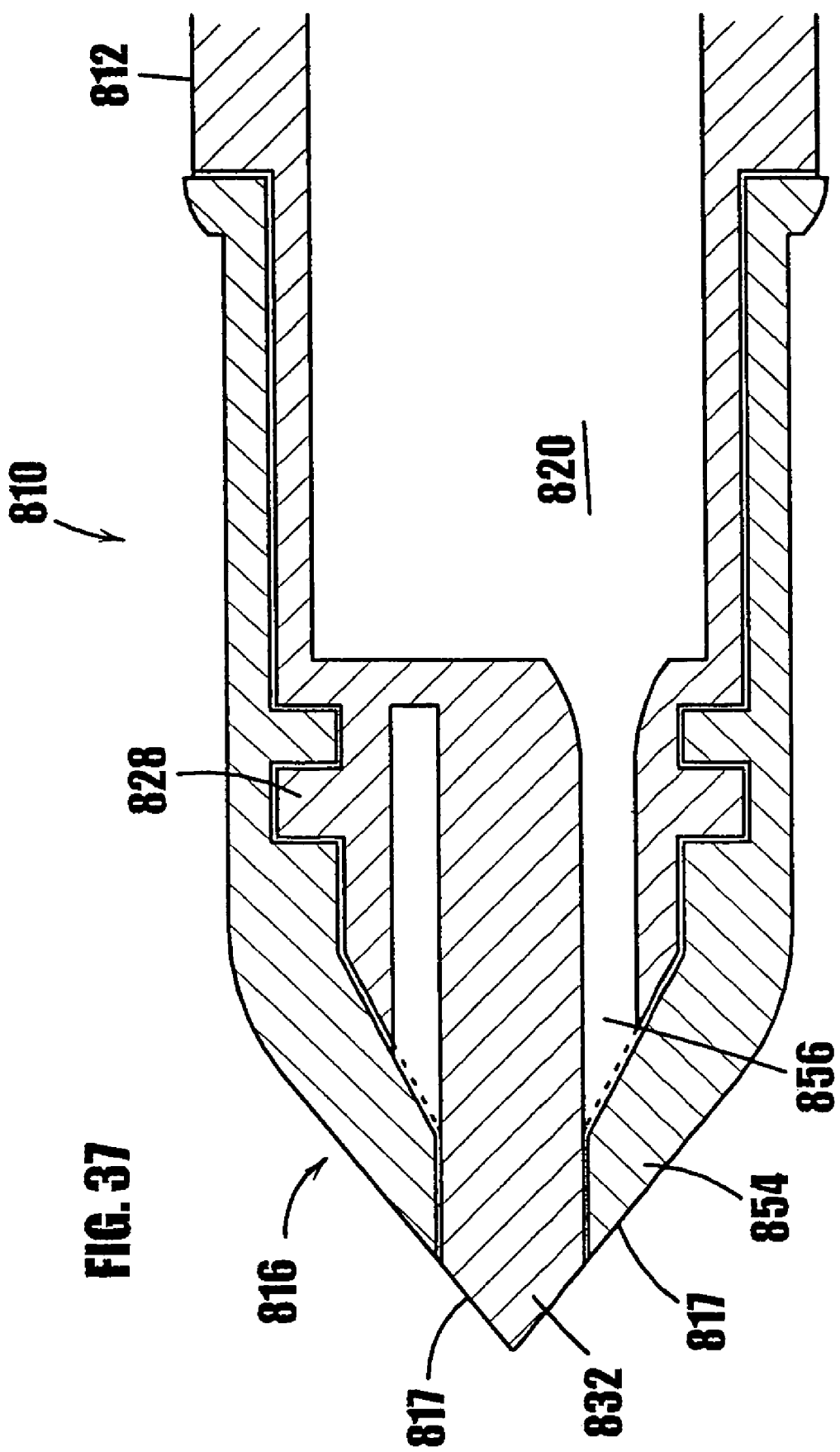
FIG. 37 is a partial, cross-sectional view of another embodiment of a syringe-type dispenser of the present invention including another uniquely-shaped dispensing tip for cosmetic applications.

In FIG. 37, another syringe-type dispenser embodying the present invention is indicated generally by the reference numeral 810. The syringe-type dispenser 810 is the same as or similar in many respects to each of the syringe-type dispensers described above with reference to FIGS. 1-36, and therefore like reference numbers preceded by the numeral "8", or preceded by the numeral "8" instead of the numerals "1" through "7", are used to indicate like elements.

The primary difference of the syringe-type dispenser 810 in comparison to the syringe type dispenser 710 described above, is that the syringe-type dispenser 810 includes a substantially frusto-conical shaped dispensing surface 817 that tapers inwardly toward a rounded dispensing tip. This type of uniquely-shaped tip is particularly suited for the application of cosmetics, such as lip gloss, eye color, concealer or cover-up, shine control, mattifying make-up, eye shadow, eye glaze, line minimizing make-up, or other make-ups or cosmetics.

One advantage of the syringe-type dispensers of FIGS. 35-37 is that they are particularly well suited for cosmetic applications, such as the dispensing of lipsticks, lip gloss, eye color cremes or liquids, and cover-ups and concealers to cover, for example, wrinkles, blemishes etc. The contoured dispensing tips provide a dispensing surface that conformably contacts the skin, such as the user's lips, eyelids or other facial surfaces, and comfortably applies a metered dose of the cosmetic substance to the spot or area of interest. In addition, the conforming surface formed by the elastic valve covers comfortably contacts the user's skin and, if desired, may be made of a material substantially matching or emulating the softness of a user's finger to thereby comfortably apply the cosmetic substance to the skin.

Yet another advantage of the syringe-type dispensers of the present invention is that they will retain the cosmetic or other substance in a sealed, airless condition within the sealed chamber of the syringe body, thereby allowing the dispenser to contain and dispense multiple doses over any desired period of time while continuously maintaining the substance in a sealed, sterile condition throughout such virtually unlimited period of use.

Yet another advantage of the syringe-type dispensers of the present disclosure is that they dispense precisely metered dosages of substances therefrom, and furthermore, may include the anti-seepage feature described above, to thereby prevent the collection of a messy or otherwise unwanted substance residue on the dispensing tip, even after multiple applications or usages of the same dispenser.

As may be recognized by those of ordinary skill in the pertinent art based on the teachings herein, numerous changes and modifications may be made to the above-described and other embodiments of the present invention without departing from its spirit or scope as defined in the appended claims. For example, the dispensers of the present invention may be made of any of numerous different materials that are currently known or later become available for dispensers of this type. Similarly, the dispensers of the present invention can take any of numerous different shapes and/or configurations that might be desired or otherwise required for particular applications. The means for controlling relative movement of the plunger and housing likewise may take any of numerous different configurations that are currently known, or are later developed for achieving incremental and/or step-wise movement to, in turn, dispense metered doses of substances. Similarly, the structure for preventing residual seepage of substance from the dispenser, such as by relieving internal pressure within the substance-containing chamber, may take the form of any of numerous different structures that are currently known, or are later developed for performing this function. Likewise, the structure for creating a "click-action" in order to signal to the user the discharge of a metered dose of substance may take any of numerous different structures or configurations that are currently known, or are later developed for performing this function. In addition, the one-way valves and/or dispensing tips of the dispensers of the present invention may take any of numerous different shapes and/or configurations. For example, as described above, the dispensing tips may define any of numerous different shapes to facilitate, for example, application of the substance to a person's skin. Accordingly, this detailed description of preferred embodiments is to be taken in an illustrative rather than a limiting sense.

What is claimed is:

1. A dispenser adapted to be filled with a substance by an apparatus including at least (i) a needle for piercing the dispenser and introducing the substance through the needle and into the dispenser, and (ii) an energy source for thermally resealing an aperture in the dispenser after withdrawal of the needle therefrom, the dispenser comprising:
    a body defining a chamber for receiving the substance;
    a one-way valve mounted on the body and including an axially-elongated valve seat, and an axially-elongated flexible valve member secured to the valve seat and defining a normally-closed valve opening at the interface of the valve member and valve seat that is connectable in fluid communication with the chamber;
    a piston mounted within the body and movable axially therethrough for varying the volume of the chamber upon dispensing substance from the chamber through the one-way valve; and
    a resealable stopper in fluid communication with the chamber and penetrable by the needle for introducing the substance through the stopper and into the chamber, and including a penetrable region that is fusible in response to the application of thermal energy from the energy source thereto to hermetically seal an aperture in the penetrable region after removing the needle therefrom.

2. A dispenser as defined in claim 1, wherein at least one of the piston and body is rotatable relative to the other to move the piston axially within the body and, in turn, dispense substance from the chamber through the one-way valve.

3. A dispenser as defined in claim 1, wherein the penetrable region of the stopper is formed of at least one of a thermoplastic and elastomeric material.

4. A dispenser as defined as defined in claim 3, wherein a base portion of the stopper is formed of vulcanized rubber.

5. A dispenser as defined in claim 1, wherein the resealable stopper is located on the piston.

6. A dispenser as defined in claim 1, wherein the piston defines a one-way valve extending adjacent to the periphery thereof for allowing gas to escape out of the chamber and through the valve and for preventing gas from passing in the other direction through the valve and into the chamber.

7. A dispenser as defined in claim 6, wherein the one-way valve is defined by a flexible member extending outwardly from the piston and engageable with the body for forming a seal between the flexible member and body.

8. A dispenser as defined in claim 1, wherein the body defines at least one axially elongated fluid-passageway extending between the body and the piston for allowing fluid to pass therethrough upon filling the chamber with the substance.

9. A dispenser as defined in claim 1, wherein the energy source is a laser that transmits laser radiation at a predetermined wavelength and power, the penetrable region of the resealable stopper is heat resealable to hermetically seal the needle aperture by applying laser radiation from the laser at the predetermined wavelength and power thereto, and the stopper comprises a thermoplastic body defining (i) a predetermined wall thickness in an axial direction thereof, (ii) a predetermined color and opacity that substantially absorbs laser radiation at the predetermined wavelength and substantially prevents the passage of radiation through the predetermined wall thickness thereof, and (iii) a predetermined color and opacity that causes the laser radiation at the predetermined wavelength and power to hermetically seal a needle aperture formed in the needle penetration region thereof in a predetermined time period of less than approximately 2 seconds and substantially without burning the needle penetration region.

10. A dispenser as defined in claim 9, wherein the needle penetration region is formed of a thermoplastic blend of a first material consisting essentially of a styrene block copolymer and a second material consisting essentially of an olefin.

11. A dispenser as defined in claim 10, wherein the first and second materials are blended within a range of about 50:50 to about 95:5 by weight.

12. A dispenser as defined in claim 9, wherein the predetermined wavelength is approximately 980 nm.

13. A dispenser as defined in claim 9, wherein the predetermined power is less than approximately 30 Watts.

14. A dispenser as defined in claim 13, wherein the predetermined power is less than or equal to about 10 Watts.

15. A dispenser as defined in claim 9, wherein the predetermined color is gray.

16. A dispenser as defined in claim 9, wherein the predetermined time period is less than about 1.5 seconds.

17. A dispenser as defined in claim 10, wherein the predetermined wavelength is about 980 nm, the predetermined power is within the range of about 8 to 10 Watts, the predetermined color is gray, and the predetermined opacity is defined by a dark gray colorant additive within the range of about 0.3% to about 0.6% by weight.

18. A dispenser adapted to be filled with a substance by an apparatus including at least (i) a needle for piercing and introducing the substance into the dispenser, and (ii) an energy source for thermally resealing an aperture in the dispenser after removing the needle therefrom, the dispenser comprising:
first means defining a chamber for receiving the substance;
second means defining a normally closed opening for hermetically sealing the substance within the chamber, for allowing substance from the chamber at a pressure that exceeds an opening pressure to be dispensed therethrough, and for retaining a remaining portion of the substance hermetically sealed within the chamber;
third means movable axially through the first means for varying the volume of the chamber upon dispensing substance from the chamber; and
fourth means penetrable by the needle for introducing the substance therethrough and into the chamber, and fusible in response to the application of thermal energy from the energy source thereto for hermetically sealing an aperture in the penetrable region after removing the needle therefrom.

19. A dispenser as defined in claim 18, wherein the energy source is a laser that transmits laser radiation at a predetermined wavelength and power, and a needle penetration region of the fourth means is pierceable with a needle to form a needle aperture therethrough, and is heat resealable to hermetically seal the needle aperture by applying laser radiation from the laser at the predetermined wavelength and power thereto, wherein the fourth means includes (i) a thermoplastic body defining a predetermined wall thickness in an axial direction thereof, (ii) fifth means for substantially absorbing the laser radiation at the predetermined wavelength and substantially preventing the passage of radiation through the predetermined wall thickness thereof, and (ii) sixth means for causing the laser radiation at the predetermined wavelength and power to hermetically seal a needle aperture formed in the needle penetration region thereof in a predetermined time period of less than approximately 2 seconds and substantially without burning the needle penetration region.

20. A dispenser as defined in claim 19, wherein the fourth means and the fifth means each are defined by a predetermined color and opacity that substantially absorbs the laser radiation at the predetermined wavelength and substantially prevents the passage of the radiation through the predetermined wall thickness thereof, and that causes the laser radiation at the predetermined wavelength and power to hermetically seal a needle aperture formed in the needle penetration region thereof in a predetermined time period of less than approximately 2 seconds and substantially without burning the needle penetration region.

21. A dispenser as defined in claim 19, wherein the first means is a body; the second means is a one-way valve mounted on the body and including an axially-elongated valve seat, and an axially-elongated flexible valve member secured to the valve seat and defining a normally-closed valve opening at the interface of the valve member and valve seat that is connectable in fluid communication with the chamber; the third means is a piston mounted within the body and movable axially therethrough for varying the volume of the chamber upon dispensing substance from the chamber and through the one-way valve; and the fourth means is a resealable stopper in fluid communication with the chamber and penetrable by the needle for introducing the substance through the stopper and into the chamber, and including a penetrable region that is fusible in response to the application of thermal energy from the energy source thereto for hermetically sealing an aperture in the penetrable region after removing the needle therefrom.

22. A method of filling a dispenser with a predetermined substance, comprising the following steps:
providing a dispenser including a body defining a chamber, a piston slidably received within the body, a one-way valve mounted on the body and including an axially-elongated valve seat, and an axially-elongated flexible valve member secured to the valve seat and defining a normally-closed valve opening at the interface of the valve member and valve seat that is connectable in fluid communication with the chamber, and a resealable stopper including a resealable portion fusible in response to the application of thermal energy thereto;
sterilizing an exposed surface of the stopper;
penetrating the stopper with a needle coupled in fluid communication with a source of the substance;
introducing the substance through the needle and into the chamber of the body;
withdrawing the needle from the stopper; and
applying sufficient thermal energy to the penetrated region of the resealable portion of the stopper to fuse the penetrated region and form a substantially gas-tight seal between the penetrated region and the chamber of the body.

23. A method as defined in claim 22, wherein the step of applying thermal energy includes applying laser radiation at a predetermined wavelength and power to the penetrated region of the stopper, and further comprising the steps of providing a resealable stopper comprising a thermoplastic body defining a predetermined wall thickness in an axial direction thereof, selecting a predetermined color and opacity of the thermoplastic body that substantially absorbs the laser radiation at the predetermined wavelength and substantially prevents the passage of the radiation through the predetermined wall thickness thereof, and selecting a predetermined color and opacity of the thermoplastic body that causes the laser radiation at the predetermined wavelength and power to hermetically seal a needle aperture formed in the needle penetration region thereof in a predetermined time period of less than approximately 2 seconds and substantially without burning the needle penetration region.

* * * * *